US010597368B2

(12) United States Patent
Sello et al.

(10) Patent No.: US 10,597,368 B2
(45) Date of Patent: *Mar. 24, 2020

(54) SYRINGOLIN ANALOGUES AND METHODS OF MAKING AND USING SAME

(71) Applicant: BROWN UNIVERSITY, Providence, RI (US)

(72) Inventors: Jason K. Sello, Providence, RI (US); Kyle A. Totaro, Raynham, MA (US)

(73) Assignee: BROWN UNIVERSITY, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/570,874

(22) PCT Filed: May 7, 2016

(86) PCT No.: PCT/US2016/031384
§ 371 (c)(1),
(2) Date: Oct. 31, 2017

(87) PCT Pub. No.: WO2016/182968
PCT Pub. Date: Nov. 17, 2016

(65) Prior Publication Data
US 2019/0010133 A1 Jan. 10, 2019

Related U.S. Application Data

(60) Provisional application No. 62/193,471, filed on Jul. 16, 2015, provisional application No. 62/158,997, filed on May 8, 2015.

(51) Int. Cl.
*A61K 31/404* (2006.01)
*A61P 35/00* (2006.01)
*C07D 403/06* (2006.01)
*C07D 245/02* (2006.01)

(52) U.S. Cl.
CPC ............ *C07D 245/02* (2013.01); *A61P 35/00* (2018.01)

(58) Field of Classification Search
CPC ..... A61K 31/404; A61P 35/00; C07D 403/06; C07D 245/02
USPC .................. 514/414, 415, 183; 548/469, 468
See application file for complete search history.

(56) References Cited

U.S. PATENT DOCUMENTS

| 5,007,790 A | 4/1991 | Shell |
| 5,169,645 A | 12/1992 | Shukla et al. |
| 5,582,837 A | 12/1996 | Shell |
| 5,972,389 A | 10/1999 | Shell et al. |
| 6,323,219 B1 | 11/2001 | Costanzo |
| 6,340,475 B2 | 1/2002 | Shell et al. |
| 6,451,808 B1 | 9/2002 | Cowles |
| 6,488,962 B1 | 12/2002 | Berner et al. |
| 8,524,738 B2 | 9/2013 | Kiyoto et al. |
| 2002/0051820 A1 | 5/2002 | Shell et al. |
| 2003/0039688 A1 | 2/2003 | Shell et al. |
| 2003/0044466 A1 | 3/2003 | Markey et al. |
| 2003/0104053 A1 | 6/2003 | Gusler et al. |
| 2003/0104062 A1 | 6/2003 | Berner et al. |
| 2003/0147952 A1 | 8/2003 | Lim |
| 2013/0065872 A1* | 3/2013 | Pirrung ................ C07D 245/02 514/183 |
| 2014/0080770 A1 | 3/2014 | Miyazaki et al. |
| 2014/0147488 A1 | 5/2014 | Elfstrand et al. |
| 2016/0130257 A1* | 5/2016 | Sello .................... C07D 245/02 514/414 |

FOREIGN PATENT DOCUMENTS

| WO | 90/11757 A1 | 10/1990 |
| WO | 93/18755 A1 | 9/1993 |
| WO | 97/47285 A1 | 12/1997 |
| WO | 98/11879 A1 | 3/1998 |
| WO | 98/55107 A1 | 12/1998 |
| WO | 01/32217 A2 | 5/2001 |
| WO | 01/56544 A2 | 8/2001 |
| WO | 01/97783 A1 | 12/2001 |
| WO | 02/32416 A2 | 4/2002 |
| WO | 02/096404 A1 | 12/2002 |
| WO | 03/035029 A1 | 5/2003 |
| WO | 03/035039 A1 | 5/2003 |
| WO | 03/035040 A1 | 5/2003 |
| WO | 03/035041 A1 | 5/2003 |
| WO | 03/035177 A2 | 5/2003 |
| WO | 2014/183015 A1 | 11/2014 |

OTHER PUBLICATIONS

Ibarra-Rivera, T., J. Opoku-Ansah, S. Ambadi, A. Bachmann and M. Pirrung, "Syntheses and cytotoxicity of syringolin B-based proteasome inhibitors", Tetrahed. (2011), 67: pp. 9950-9956. (Year: 2011).*
International Search Report and the Written Opinion dated Aug. 8, 2016 for PCT/US2016/031384.
"Fieser and Fieser's Reagents for Organic Synthesis", John Wiley and Sons, vols. 1-17, 1991.
"March's Advanced Organic Chemistry", Wiley Interscience, 4th Edition, 1992.
"Organic Reactions", John Wiley and Sons, vols. 1-40, 1991.
"Rodd's Chemistry of Carbon Compounds", vol. 1-5.
"Supplementals", Elsevier Science Publishers, 1989.
Chou et al., "Quantitative Analysis of Dose-Effect Relationships: The Combined Effects of Multiple Drugs or Enzyme Inhibitors", Advances in Enzyme Regulation, vol. 22, 1984, pp. 27-55.
Clerc et al., "The Natural Product Hybrid of Syringolin A and Glidobactin A Synergizes Proteasome Inhibition Potency With Subsite Selectivity", Chem Commun (Camb)., vol. 47 No. 1, Jan. 7, 2011, pp. 385-387.

(Continued)

*Primary Examiner* — Matthew P Coughlin
*Assistant Examiner* — Sagar Patel
(74) *Attorney, Agent, or Firm* — Adler Pollock & Sheehan P.C.

(57) ABSTRACT

The present invention provides, in certain aspects, novel syringolin analogues, In certain embodiments, the compounds of the invention are proteasome inhibitors, In other embodiments, the compounds treat or prevent a cancer such as, but not limited to, leukemia in a subject.

20 Claims, 41 Drawing Sheets

(56) References Cited

OTHER PUBLICATIONS

Dudnik et al., "Heterologous Expression of a Photorhabdus Luminescens Syrbactin-Like Gene Cluster Results in Production of the Potent Proteasome Inhibitor Glidobactin A", Microbiol Res., vol. 168 No. 2, Feb. 22, 2013, 21 pages.
Greene et al., "Protective Groups in Organic Synthesis", John Wiley & Sons, Inc., 3rd Edition, 1999.
Hacker et al., "Pharmacology: Principles and Practice", Academic Press, Jun. 19, 2009, pp. 216-217.
Holford et al., "Understanding the Dose-Effect Relationship-Clinical Application of Pharmacokinetic-Pharmacodynamic Models", Clinical Pharmacokinetics, vol. 6, 1981, pp. 429-453.
Kocienski, "Protective Groups", Georg Thieme Verlag, New York, 1994.
Larock, "Comprehensive Organic Transformations", VCh Publishers Inc., 1989.
Lin et al., "N,C-Capped Dipeptides with Selectivity for Mycobacterial Proteasome over Human Proteasomes: Role of S3 and S1 Binding Pockets", J. Am. Chem. Soc., vol. 135, 2013, pp. 9968-9971.
Loewe et al., "Effect of Combinations: Mathematical Basis of Problem", Arch. Exp. Pathol. Pharmacol, vol. 114, 1926, pp. 313-326.
McKennon et al., "A Convenient Reduction of Amino Acids and their Derivatives", J. Org. Chem., vol. 58, 1993, pp. 3568-3571.
Pirrung et al., "Total Synthesis of Syringolin A and B", Org. Lett., vol. 12, 2010, pp. 2402-2405.
Sundberg et al., "Advanced Organic Chemistry", Plenum Publishers, 4th Edition, vols. A and B, 2000, 2001.
Totaro et al., "Substrate-Guided Optimization of the Syringolins Yields Potent Proteasome Inhibitors With Activity Against Leukemia Cell Lines", Bioorganic & Medicinal Chemistry, vol. 23, 2015, pp. 6218-6222.

\* cited by examiner

| Compound | $k_{in}$ | $K_i$ | $k_{in}/K_i$ | Normalized $k_{in}/K_i$ |
|---|---|---|---|---|
| 1 | 0.0005502 | 2.12 | 259.5283019 | 781.4030292 |
| 2 | 0.0006132 | 3.231 | 189.7864438 | 571.4201535 |
| 3 | 0.0004723 | 0.7434 | 635.3241862 | 1912.871313 |
| 4 | 0.000472 | 7.575 | 62.31023102 | 187.6072972 |
| 5 | 0.0004789 | 0.9062 | 528.4705363 | 1591.150078 |
| 6 | 0.0004856 | 0.5916 | 820.8248817 | 2471.387684 |
| 7 | 0.0004995 | 0.9519 | 524.7399937 | 1579.917942 |
| 8 | 0.0005163 | 2.113 | 244.3445338 | 735.68685 |
| 9 | 0.0004887 | 0.9631 | 507.4239435 | 1527.781763 |
| 10 | 0.0004988 | 1.237 | 403.2336267 | 1214.079457 |
| 11 | 0.0004954 | 2.347 | 211.0779719 | 635.5259346 |
| 12 | 0.0005002 | 1.14 | 438.7719298 | 1321.080254 |
| 13 | 0.0005141 | 1.711 | 300.4675628 | 904.6653566 |
| 14 | 0.0005985 | 0.9498 | 630.1326595 | 1897.24036 |
| 15 | 0.0006234 | 0.447 | 1394.630872 | 4199.036407 |
| 16 | 0.0005508 | 0.3852 | 1429.906542 | 4305.246462 |

Fig. 5

SYRINGOLIN ANALOGUES AND METHODS OF MAKING AND USING SAME

RELATED APPLICATIONS

This application is the U.S. national phase, pursuant to 35 U.S.C. § 371, of PCT international application Ser. No. PCT/US2016/031384, filed May 7, 2016, designating the United States and published in English on Nov. 17, 2016 as publication WO 2016/182968A1, which claims priority under 35 U.S.C. § 119(e) to U.S. Provisional Application Ser. No. 62/158,997, filed May 8, 2015, and U.S. Provisional Application No. 62/193,471, filed Jul. 16, 2015, the entire disclosures of which patent applications are incorporated herein by reference.

BACKGROUND OF THE INVENTION

The 26S proteasome is a multi-subunit complex that effects targeted protein degradation in eukaryotic organisms. This proteasome is one of the highest value targets for drug discovery and development programs focused on cancer treatments. Efforts to develop anti-cancer drugs that target the proteasome are motivated by the success of bortezomib (VELCADE®), a frontline drug for the treatment of multiple myeloma and mantle cell lymphoma. Bortezomib is a peptide boronate that reversibly inhibits the proteasome via substrate imitation and labile bonding between its boronic acid moiety and active site threonine residues of the proteasome's proteolytic ☐ subunits. Bortezomib's substrate mimicry and its active site reactive warhead share structural features with most of the naturally occurring and designed proteasome inhibitors that have been reported to date, such as peptidyl aldehydes, peptidyl epoxyketones, and β-lactones. An analogue of a peptidyl epoxyketone natural product, carfilzomib (KYPROLIS®), has been approved for the treatment of multiple myeloma.

Although natural products in the β-lactone and peptidyl epoxyketone classes of proteasome inhibitors have been studied, those in the syringolin family have received much less attention. Syringolins were first isolated in 1998 from *Pseudomonas syringae* pv. *syringae* and display a twelve-membered macrocyclic lactam and an exocyclic dipeptide urea (See, FIG. 1). Irreversible proteasome inhibition by these molecules is due to the reaction of the α,β-unsaturated carbonyl moiety (i.e., the vinylogous amino acid) in their macrolactams with the catalytic threonine residues of the proteolytic subunits. Syringolin congeners mostly differ with respect to the dipeptide peptide urea moiety, but syringolins B and E are distinguished from the others by the absence of a unit of unsaturation in the macrolactam. The presence of the alkene likely strains the macrolactam such that it is more prone to form the inhibitory conjugate, as evidenced by the fact that syringolin A is the most potent congener. Syringolin derivatives have not been extensively studied in the context of anticancer drug development.

There is a need in the art to identify novel compounds that can be used to treat or prevent cancers, such as leukemia, in a subject. The present invention addresses and meets this need.

BRIEF SUMMARY OF THE INVENTION

The invention provides a compound of formula (I), or a salt, racemic mixture, enantiomer, pro-drug, and/or diastereoisomer thereof:

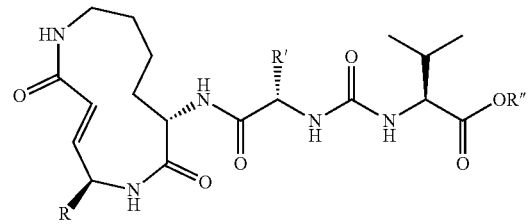

(I)

wherein:
R is $C_1$-$C_6$ alkyl, arylalkyl, or heteroarylalkyl, wherein each of the alkyl, arylakyl or heteroarylalkyl groups is independently optionally substituted with one or more of $C_1$-$C_6$ alkyl, haloalkyl, F, Cl, Br, I, $C_1$-$C_6$ alkoxy, or hydroxy;
R' is $C_1$-$C_6$ alkyl or arylalkyl, wherein each of the alkyl or arylakyl groups is independently optionally substituted with one or more of $C_1$-$C_6$ alkyl, haloalkyl, F, Cl, Br, I, $C_1$-$C_6$ alkoxy, or hydroxy;
R" is H or $C_1$-$C_{16}$ alkyl, wherein each of the alkyl groups is independently optionally substituted with one or more of $C_1$-$C_6$ alkyl, F, Cl, Br, I, $C_1$-$C_6$ alkoxy, or hydroxy; with the proviso that R and R' are not simultaneously isopropyl in (I).

The invention provides a compound of formula (II), or a salt, racemic mixture, enantiomer, pro-drug, and/or diastereoisomer thereof:

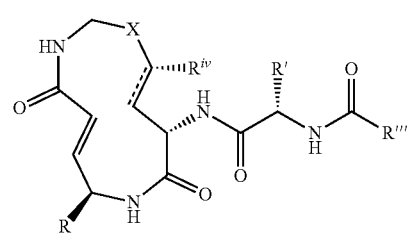

(II)

wherein:
═══ represents a single or double bond;
X is $CH_2$ or O;
R is $C_1$-$C_6$ alkyl, arylalkyl, or heteroarylalkyl, wherein each of the alkyl, arylakyl or heteroarylalkyl groups is independently optionally substituted with one or more of $C_1$-$C_6$ alkyl, haloalkyl, F, Cl, Br, I, $C_1$-$C_6$ alkoxy, or hydroxy;
R' is $C_1$-$C_6$ alkyl or arylalkyl, wherein each of the alkyl or arylakyl groups is independently optionally substituted with one or more of $C_1$-$C_6$ alkyl, haloalkyl, F, Cl, Br, I, $C_1$-$C_6$ alkoxy, or hydroxy;
R''' is alkylamino or alkenyl, wherein each of the alkylamino and alkenyl groups is independently optionally substituted with one or more of $C_1$-$C_{12}$ alkyl, $C_1$-$C_{12}$ alkenyl, and —$CO_2H$; and
$R^{iv}$ is H or OH.

In some embodiments, ═══ is a single bond. In other embodiments, ═══ is a double bond. In some embodiments, X is $CH_2$. In other embodiments, X is O.

In certain embodiments, R is $C_1$-$C_6$ alkyl, aryl($CH_2$)—, or heteroaryl($CH_2$)—, wherein each of the alkyl, aryl($CH_2$)— or heteroaryl($CH_2$)— groups is independently optionally substituted with one or more of $C_1$-$C_6$ alkyl, haloalkyl, F, Cl, Br, I, $C_1$-$C_6$ alkoxy, or hydroxy. In other embodiments, R is methyl, isopropyl, isobutyl, benzyl or 3-indolylmethyl, wherein each of the benzyl or 3-indolylmethyl groups is independently optionally substituted with one or more of $C_1$-$C_6$ alkyl, haloalkyl, F, Cl, Br, I, $C_1$-$C_6$ alkoxy, or hydroxy.

In other embodiments, when R is benzyl, the substituted benzyl is 2-trifluoromethylbenzyl, 3-trifluoromethylbenzyl, 4-trifluoromethylbenzyl, 2-fluorobenzyl, 3-fluorobenzyl, 4-fluorobenzyl, 2-chlorobenzyl, 3-chlorobenzyl, 4-chlorobenzyl, 2-methylbenzyl, 3-methylbenzyl, 4-methylbenzyl, 2,4-difluorobenzyl, 3,5-difluorobenzyl, 2,4-dichlorobenzyl, or 2,4-dimethylbenzyl.

In other embodiments, R' is isopropyl and R is

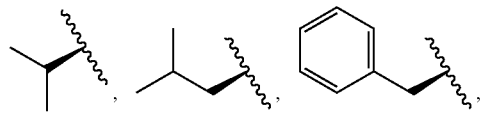,

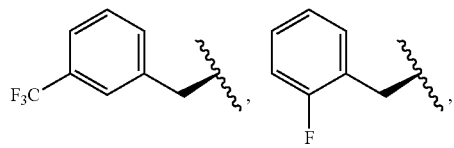,

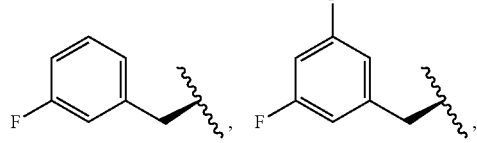,

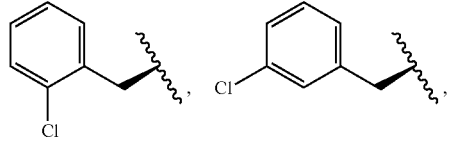,

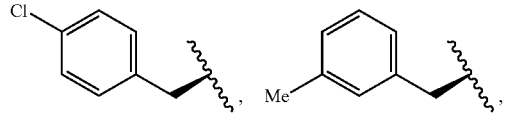,

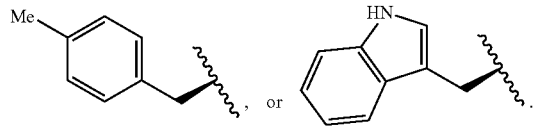.

In yet other embodiments, R' is benzyl or substituted benzyl and R is

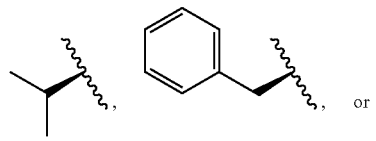, or

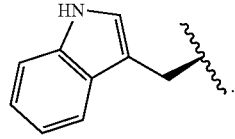.

In some embodiments, R is

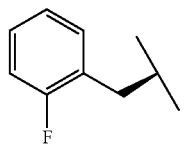

and R' is selected from

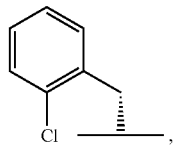,

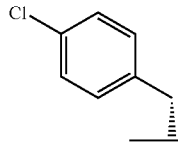,

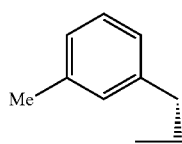,

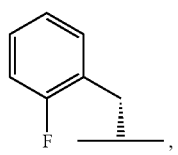,

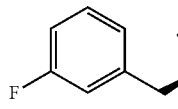, and .

In other embodiments, R is

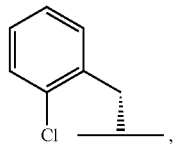, and R' is selected from

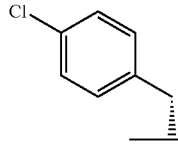,

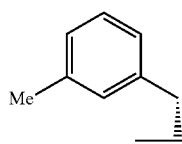,

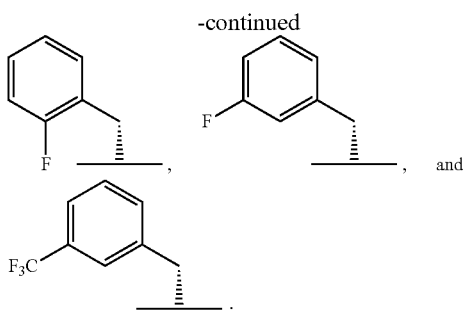

In other embodiments, R is

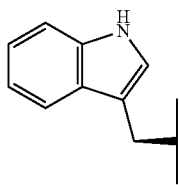

and R' is

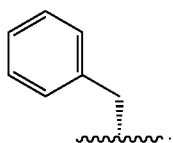

In yet other embodiments, R" is H, methyl, ethyl, propyl, isopropyl or dodecyl.

In some embodiments, R'" is alkylamino where the alkyl is selected from isopropyl, 2-methylbutyl, and 1-hydroxyethyl. In some embodiments, the alkyl is substituted with —$CO_2H$, aminoalkyl, or alkenyl. The aminoalkyl substituent can be, for example, —$NHC_{12}H_{25}$. The alkenyl substituent can be, for example, —CH=CH=CH—$CH_2$—$C_7H_{15}$.

In some embodiments, $R^{iv}$ is H. In other embodiments, $R^{iv}$ is OH.

In yet other embodiments, the salt is an acid addition salt selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid, and any combinations thereof.

In yet other embodiments, the salt is a base addition salt selected from the group consisting of calcium, magnesium, potassium, sodium, ammonium, zinc, a basic amine salt, and any combinations thereof, wherein the basic amine is selected from the group consisting of triethylamine, diisopropylethylamine, trimethylamine, N,N'-dibenzylethylenediamine, chloroprocaine, choline, diethanolamine, ethylenediamine, meglumine, procaine and any combinations thereof.

The invention further provides pharmaceutical compositions comprising at least one compound of the invention and at least one pharmaceutically acceptable carrier. In certain embodiments, the compositions further comprise at least one additional anticancer agent. In other embodiments, the at least one compound and the at least one additional anticancer agent are co-formulated in the pharmaceutical composition.

The invention also provides methods of inhibiting proteasome activity in a cell. The invention further provides methods of inhibiting or preventing protein degradation in a cell. The invention still further provides methods of treating or preventing cancer in a subject in need thereof.

In certain embodiments, the methods comprise contacting the cell with an effective amount of at least one compound of the invention. In some embodiments, the compound is a compound of Formula I. In other embodiments, the compound is a compound of Formula II.

In yet other embodiments, the method comprises administering to the subject a therapeutically effective amount of at least one compound of the invention. In some embodiments, the compound is a compound of Formula I. In other embodiments, the compound is a compound of Formula II.

In yet other embodiments, the at least one compound inhibits the activity of the β2 or β5 subunit of the proteasome. In some embodiments, the compound is a compound of Formula I. In other embodiments, the compound is a compound of Formula II.

In still other embodiments, the cell is in vitro or in vivo.

In yet other embodiments, the cell comprises a cancer cell. In still other embodiments, the cancer cell comprises a leukemia cell, non-small cell lung cancer cell, colon cancer cell, CNS cancer cell, melanoma cell, ovarian cancer cell, or breast cancer cell. In yet other embodiments, the cancer cell comprises a leukemia cell. In still other embodiments, the cancer comprises leukemia, non-small cell lung cancer, colon cancer, CNS cancer, melanoma, ovarian cancer, or breast cancer. In still other embodiments, the cancer comprises leukemia.

In yet other embodiments, administration of the at least one compound inhibits or prevents protein degradation in the subject. In still other embodiments, administration of the at least one compound inhibits proteasome activity in the subject. In some embodiments, the compound is a compound of Formula I. In other embodiments, the compound is a compound of Formula II, In yet other embodiments, the subject is further administered at least one additional anticancer agent. In still other embodiments, the at least one compound and the at least one additional agent are co-administered to the subject. In yet other embodiments, the at least one compound and the at least one agent are co-formulated.

In yet other embodiments, the compound is administered to the subject by at least one route selected from the group consisting of intravenous, oral, inhalational, rectal, vaginal, transdermal, intranasal, buccal, sublingual, parenteral, intrathecal, intragastrical, ophthalmic, pulmonary and topical routes.

In yet other embodiments, the methods further comprise procuring the at least one compound of the invention.

In yet other embodiments, the cell is mammalian. In still other embodiments, the subject is a mammal. In yet other embodiments, the cell is human. In still other embodiments, the subject is human.

The invention still further provides a prepackaged kit comprising a compound of the invention, an instructional material for use thereof, and optionally further an applicator.

The instructional material included in the kit comprises instructions for preventing or treating a cancer in a subject. In certain embodiments, the kit further comprises at least one additional anticancer agent.

Other aspects, embodiments, advantages, and features of the present invention will become apparent from the following specification.

BRIEF DESCRIPTION OF THE DRAWINGS

The following detailed description of various embodiments of the invention will be better understood when read in conjunction with the appended drawings. For the purpose of illustrating the invention, there are shown in the drawings certain specific embodiments. It should be understood, however, that the invention is not limited to the precise arrangements and instrumentalities of the embodiments shown in the drawings.

FIG. 5 is a table illustrating kinetic data used for calculating second-order rate constants.

FIGS. 1A-11B comprise a set of graphs illustrating dose-dependent growth inhibition of leukemia cells by selected syringolin analogues.

DETAILED DESCRIPTION OF THE INVENTION

Figure 1:
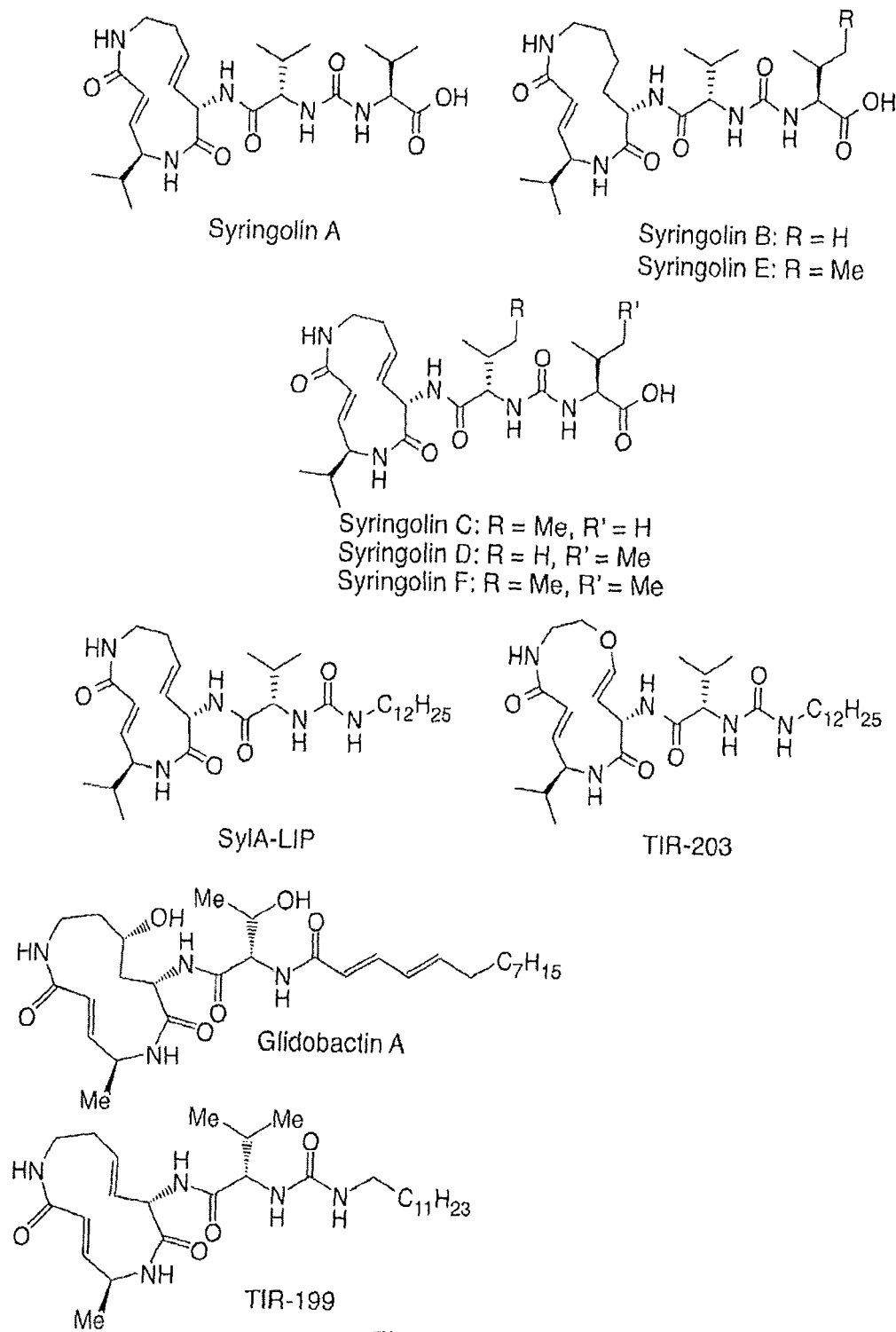
FIG. 1 is a non-limiting illustration of syringolin natural products (syringolins A-F) and synthetic analogues thereof (SylA-Lip, Glidobactin A, TIR-199, and TIR-203).

The invention is based, at least in part, on the unexpected identification of novel syringolin analogues that inhibit the growth and/or kill cancer cells. In certain embodiments, the compounds of the invention inhibit the growth and/or kill leukemia cells.

As demonstrated herein, syringolin analogues were designed, synthesized, and evaluated. In certain embodiments, the compounds of the invention inhibit the activity of the proteasome with second-order rate constants that are five-fold greater than the methyl ester of syringolin B. In other embodiments, the compounds of the invention have good in vitro potency against cancer cell lines. In yet other embodiments, the compounds of the invention have good in vitro potency against leukemia cell lines.

Syringolin analogs that bear resemblance to chymotrypsin substrates can be more potent inhibitors of the □5-subunits of the proteasome than the parent Syringolin, yet their subunit-selectivities for inhibition are comparable. The fact that potency, and not selectivity, has been improved could indicate that inhibition of multiple proteolytic subunits by a compound correlates with significant suppression of protein degradation.

Analysis of the crystal structure of syringolin A bound to the yeast proteasome suggests that the side chains of the macrolactam's vinylogous amino acid and the amino acid residue appended to the macrocycle mimic those of amino acids at the P1 and P3 positions of a proteasome substrate, respectively. Without wishing to be limited by any theory, a substrate's residue at the P1 position has the scissile bond and is separated from the one at the upstream P3 position by a single residue. The syringolins react preferentially (but not exclusively) with the β5 subunit of eukaryotic proteasomes. The β5 subunit has a substrate specificity reminiscent of chymotrypsin, a protease that prefers substrates with aromatic amino acid residues (e.g., phenylalanine, tyrosine, and tryptophan) at the P1 position. In contrast, the β1 and β2 subunits have substrate preferences similar to caspase and trypsin, respectively. Caspase prefers acidic residues at the scissile bond, while trypsin prefers those that are basic. Without wishing to be limited by any theory, the biased reactivity of the syringolins towards the β5 subunit may be a consequence of their macrolactams having a hydrophobic, vinylogous amino acid (derived from valine) rather than one that is polar. In certain embodiments, the potency and selectivity of β5 subunit inhibition by the syringolins is enhanced by replacing this mimic of valine with aromatic moieties, like those at the P1 position of chymotrypsin substrates. As demonstrated herein, syringolin analogues, designed to closely mimic the various substrates of the proteasome subunit having specificity like chymotrypsin, were designed and evaluated.

In certain embodiments, a model for substrate mimicry by the syringolins is illustrated by:

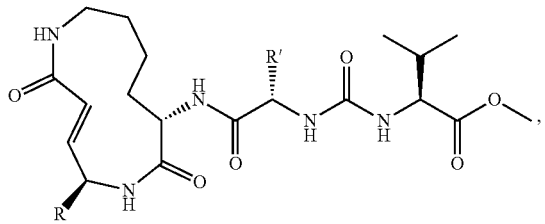

wherein R and R' mimic the side chains of P1 and P3 residues of the proteasome substrate, respectively.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the certain specific methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more advantageously ±5%, even more advantageously ±1%, and still more advantageously ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

The terms "cancer" refers to the physiological condition in a subject typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), vulval cancer, thyroid cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, head and neck cancer, leukemias and lymphomas.

In one aspect, the terms "co-administered" and "co-administration" as relating to a subject refer to administering to the subject a compound of the invention or salt thereof along with a compound that may also treat the disorders or diseases contemplated within the invention. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example, by means of a computer, such as by electronic mail, or download from a website.

The terms "patient," "subject" or "individual" are used interchangeably herein, and refer to any animal, or cells thereof whether in vitro or in situ, amenable to the methods described herein. In non-limiting embodiments, the patient, subject or individual is a human.

As used herein, the term "pharmaceutically acceptable" refers to a material, such as a carrier or diluent, which does not abrogate the biological activity or properties of the compound, and is relatively non-toxic; i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier is "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient, Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "prevent," "preventing" or "prevention," as used herein, means avoiding or delaying the onset of symptoms associated with a disease or condition in a subject that has not developed such symptoms at the time the administering of an agent or compound commences.

As used herein, the term "procure" or "procuring" as relating to a subject in need of being administered a therapeutically active compound refers to the act of synthesizing, packaging, prescribing, purchasing, providing or otherwise acquiring the compound so that the subject may be administered the compound.

By the term "specifically bind" or "specifically binds," as used herein, is meant that a first molecule preferentially binds to a second molecule (e.g., a particular receptor or enzyme), but does not necessarily bind only to that second molecule.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Certain specific examples include ($C_1$-$C_6$)alkyl, such as, but not limited to, ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Certain specific examples include ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, tetrahydro-2-H-pyranyl, —$NH_2$, —$N(CH_3)_2$, (1-methyl-imidazol-2-yl), pyridin-2-yl, pyridin-3-yl, pyridin-4-yl, —C(=O)OH, trifluoromethyl, —C≡N, —C(=O)O($C_1$-$C_4$)alkyl, —C(=O)$NH_2$, —C(=O)NH($C_1$-$C_4$)alkyl, —C(=O)N(($C_1$-$C_4$)alkyl)$_2$, —$SO_2NH_2$, —C(=NH)$NH_2$, and —$NO_2$, advantageously containing one or two substituents selected from halogen, —OH, alkoxy, —$NH_2$, trifluoromethyl, —N($CH_3$)$_2$, and —C(=O)OH, more advantageously selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. In certain embodiments, alkoxy includes ($C_1$-$C_3$)alkoxy, such as, but not limited to, ethoxy and methoxy.

As used herein, the term "halo" or "halogen" alone or as part of another substituent means, unless otherwise stated, a fluorine, chlorine, bromine, or iodine atom, advantageously, fluorine, chlorine, or bromine, more advantageously, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized □ (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. In certain embodiments, aryl includes phenyl and naphthyl, in particular, phenyl.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl (benzyl). Examples included aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Specific examples include substituted aryl($CH_2$)—. Similarly, the term "heteroaryl-($C_1$-$C_3$) alkyl" means a functional group wherein a one to three carbon alkylene chain is attached to a heteroaryl group, e.g., —$CH_2CH_2$-pyridyl. One embodiment is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Specific examples include substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, in particular, straight. In this disclosure, "comprises," "comprising," "containing" and "having" and the like can have the meaning ascribed to them in U.S. Patent law and can mean "includes," "including" and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Compounds and Compositions

The invention provides a compound of formula (I), or a salt, racemic mixture, enantiomer, pro-drug, and/or diastereoisomer thereof:

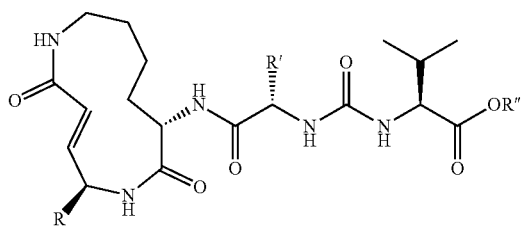

(I)

wherein:
R is $C_1$-$C_6$ alkyl, arylalkyl, or heteroarylalkyl, wherein each of the alkyl, arylakyl or heteroarylalkyl groups is independently optionally substituted with one or more of $C_1$-$C_6$ alkyl, haloalkyl, F, Cl, Br, I, $C_1$-$C_6$ alkoxy, or hydroxy;

R' is $C_1$-$C_6$ alkyl or arylalkyl, wherein each of the alkyl or arylakyl groups is independently optionally substituted with one or more of $C_1$-$C_6$ alkyl, haloalkyl, F, Cl, Br, I, $C_1$-$C_6$ alkoxy, or hydroxy;

R" is H or $C_1$-$C_{16}$ alkyl, wherein each of the alkyl groups is independently optionally substituted with one or more of $C_1$-$C_6$ alkyl, F, Cl, Br, I, $C_1$-$C_6$ alkoxy, or hydroxy; with the proviso that R and R' are not simultaneously isopropyl in (I).

The invention provides a compound of formula (II), or a salt, racemic mixture, enantiomer, pro-drug, and/or diastereoisomer thereof:

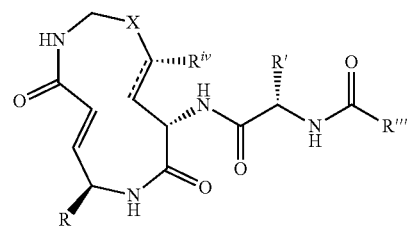

(II)

wherein:
==== represents a single or double bond;
X is $CH_2$ or O;
R is $C_1$-$C_6$ alkyl, arylalkyl, or heteroarylalkyl, wherein each of the alkyl, arylakyl or heteroarylalkyl groups is independently optionally substituted with one or more of $C_1$-$C_6$ alkyl, haloalkyl, F, Cl, Br, I, $C_1$-$C_6$ alkoxy, or hydroxy;
R' is $C_1$-$C_6$ alkyl or arylalkyl, wherein each of the alkyl or arylakyl groups is independently optionally substituted with one or more of $C_1$-$C_6$ alkyl, haloalkyl, F, Cl, Br, I, $C_1$-$C_6$ alkoxy, or hydroxy;
R''' is alkylamino or alkenyl, wherein each of the alkylamino and alkenyl groups is independently optionally substituted with one or more of $C_1$-$C_{12}$ alkyl, $C_1$-$C_{12}$ alkenyl, and —$CO_2H$; and
$R^{iv}$ is H or OH.

In some embodiments, ==== is a single bond. In other embodiments, ==== is a double bond. In some embodiments, X is $CH_2$. In other embodiments, X is O.

In certain embodiments, R is $C_1$-$C_6$ alkyl, aryl($CH_2$)—, or heteroaryl($CH_2$)—, wherein each of the alkyl, aryl($CH_2$)— or heteroaryl($CH_2$)— groups is independently optionally substituted with one or more of $C_1$-$C_6$ alkyl, haloalkyl, F, Cl, Br, I, $C_1$-$C_6$ alkoxy, or hydroxy. In other embodiments, R is methyl, isopropyl, isobutyl, benzyl or 3-indolylmethyl, wherein each of the benzyl or 3-indolylmethyl groups is independently optionally substituted with one or more of $C_1$-$C_6$ alkyl, haloalkyl, F, Cl, Br, I, $C_1$-$C_6$ alkoxy, or hydroxy.

In other embodiments, when R is benzyl, the substituted benzyl is 2-trifluoromethylbenzyl, 3-trifluoromethylbenzyl, 4-trifluoromethylbenzyl, 2-fluorobenzyl, 3-fluorobenzyl, 4-fluorobenzyl, 2-chlorobenzyl, 3-chlorobenzyl, 4-chlorobenzyl, 2-methylbenzyl, 3-methylbenzyl, 4-methylbenzyl, 2,4-difluorobenzyl, 3,5-difluorobenzyl, 2,4-dichlorobenzyl, or 2,4-dimethylbenzyl.

In other embodiments, R' is isopropyl and R is

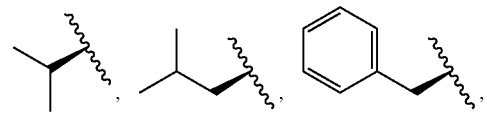

-continued
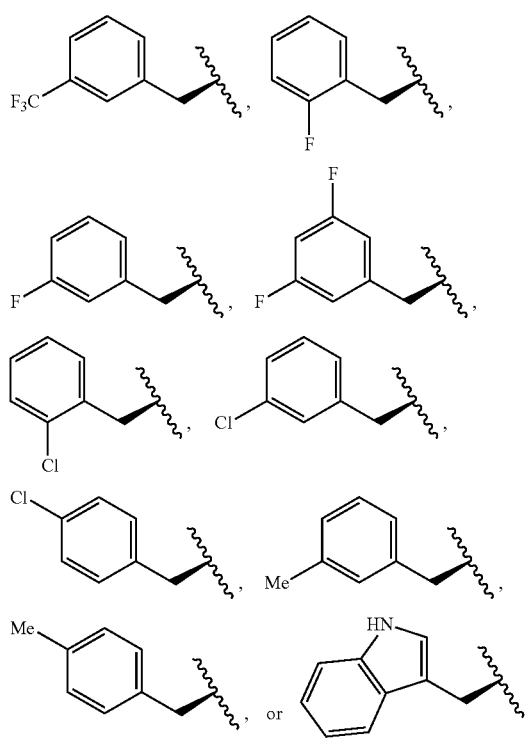
In yet other embodiments, R' is benzyl or substituted benzyl and R is
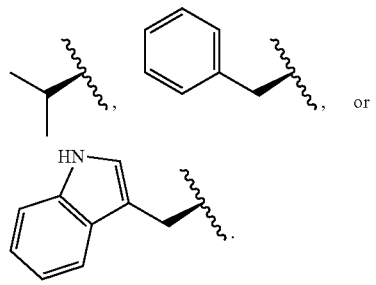
In some embodiments, R is
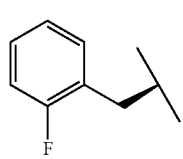
and R' is selected from
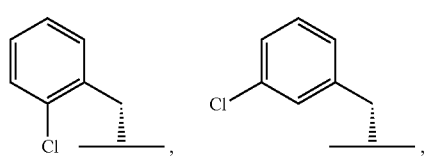
-continued
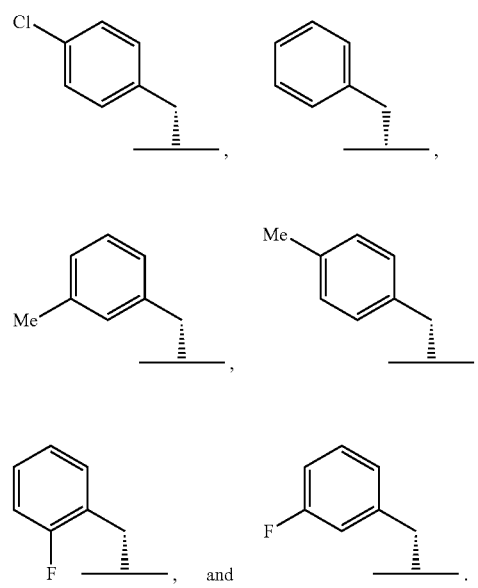
In other embodiments, R is
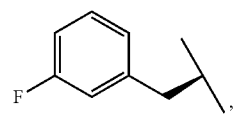
and R' is selected from
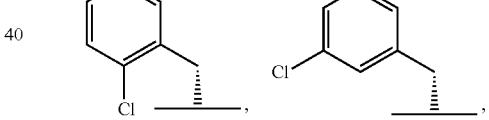
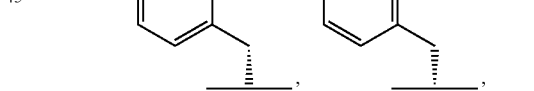
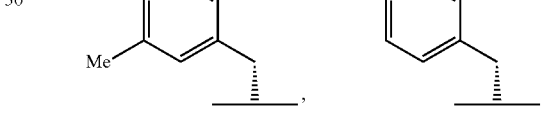

In other embodiments, R is

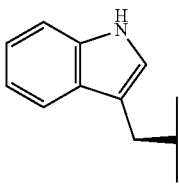

and R' is

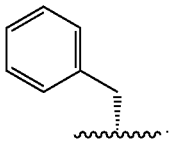

In yet other embodiments, R" is H, methyl, ethyl, propyl, isopropyl or dodecyl.

In some embodiments, R''' is alkylamino where the alkyl is selected from isopropyl, 2-methylbutyl, and 1-hydroxyethyl. In some embodiments, the alkyl is substituted with —CO$_2$H, aminoalkyl, or alkenyl. The aminoalkyl substituent can be, for example, —NHC$_{12}$H$_{25}$. The alkenyl substituent can be, for example, —CH═CH═CH—CH$_2$—C$_7$H$_{15}$.

In some embodiments, R$^{iv}$ is H. In other embodiments, R$^{iv}$ is OH.

In yet other embodiments, the salt is an acid addition salt selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid, and any combinations thereof.

In certain embodiments, the salt is a base addition salt selected from the group consisting of calcium, magnesium, potassium, sodium, ammonium, zinc, a basic amine salt, and any combinations thereof, wherein the basic amine is selected from the group consisting of triethylamine, diisopropylethylamine, trimethylamine, N,N'-dibenzylethylenediamine, chloroprocaine, choline, diethanolamine, ethylenediamine, meglumine, procaine and any combinations thereof.

The invention also provides pharmaceutical compositions comprising at least one compound of the invention and at least one pharmaceutically acceptable carrier. In certain embodiments, the compositions further comprise at least one additional anticancer agent. In other embodiments, the at least one compound and the at least one additional anticancer agent are co-formulated in the pharmaceutical composition.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs (see for example Hacker, et al., Pharmacology: Principles and Practice. Academic Press, Jun. 19, 2009. pp. 216-217). A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. Accordingly, In certain embodiments, a prodrug is created by methods well known in the art, by which the appropriate substituent to decrease or eliminate the susceptibility of the aromatic ring to metabolic reactions is added, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S, In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Synthesis

The compounds described herein, and other related compounds having different substituents, are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means, Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxy benzyl, while coexisting amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from allyl, benzyl, carboxyethoxycarbonyl (Cbz), alloxycarbonyl (alloc), methyl, ethyl, tert-butyl, tert-butyldimethylsilyl (TBDMS), 2-(tert-butylsilyl)ethoxycarbonyl (Teoc), Boc, p-methoxybenzyl (PMB), trityl, acetyl and Fmoc.

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

The compounds of the invention may be prepared according to the general methodology illustrated in the synthetic schemes described below. The reagents and conditions described herein may be modified to allow the preparation of the compounds of the invention, and such modifications are known to those skilled in the art. The scheme included herein are intended to illustrate but not limit the chemistry and methodologies that one skilled in the art may use to make compounds of the invention.

Salts

The compounds described herein may form salts with acids, and such salts are included in the present invention. In certain embodiments, the salts are pharmaceutically acceptable salts. The term "salts" embraces addition salts of free acids that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric or galacturonic acid.

Suitable pharmaceutically acceptable base addition salts of compounds of the invention include, for example, metallic salts including alkali metal, alkaline earth metal or transition metal salts such as, for example, calcium, magnesium, potassium, sodium or zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) or procaine. All of these salts may be prepared from the corresponding compound by reacting, for example, the appropriate acid or base with the compound.

Methods

The invention provides methods of inhibiting proteasome activity in a cell. The invention further provides methods of inhibiting or preventing protein degradation in a cell. The invention still further provides methods of treating or preventing cancer in a subject in need thereof.

In certain embodiments, the methods comprise contacting the cell with an effective amount of at least one compound of the invention.

In other embodiments, the method comprises administering to the subject a therapeutically effective amount of at least one compound of the invention.

In yet other embodiments, the at least one compound inhibits the activity of the β2 or β5 subunit of the proteasome. In still other embodiments, the cell is in vitro or in vivo. In yet other embodiments, the cell comprises a cancer cell. In yet other embodiments, the cancer cell comprise a leukemia cell, non-small cell lung cancer cell, colon cancer cell, CNS cancer cell, melanoma cell, ovarian cancer cell, or breast cancer cell. In still other embodiments, the cancer cell comprises a leukemia cell. In yet other embodiments, the cancer comprises leukemia, non-small cell lung cancer, colon cancer, CNS cancer, melanoma, ovarian cancer, or breast cancer. In still other embodiments, the cancer comprises leukemia. In yet other embodiments, the cancer is leukemia.

In yet other embodiments, administration of the at least one compound inhibits or prevents protein degradation in the subject. In still other embodiments, administration of the at least one compound inhibits proteasome activity in the subject.

In yet other embodiments, the subject is further administered at least one additional anticancer agent. In still other embodiments, the at least one compound and the at least one additional agent are co-administered to the subject. In yet other embodiments, the at least one compound and the at least one agent are co-formulated.

In yet other embodiments, the compound is administered to the subject by an intravenous, oral, inhalational, rectal, vaginal, transdermal, intranasal, buccal, sublingual, parenteral, intrathecal, intragastrical, ophthalmic, pulmonary or topical route.

In yet other embodiments, the methods further comprise procuring the at least one compound of the invention.

In yet other embodiments, the cell is mammalian. In still other embodiments, the subject is a mammal.

In yet other embodiments, the cell is human. In still other embodiments, the subject is a human.

Kits

The invention provides a kit comprising a compound of the invention, an applicator, and an instructional material for use thereof. The instructional material included in the kit comprises instructions for preventing or treating a disorder or disease contemplated within the invention in a subject. The instructional material recites the amount of, and frequency with which, the compound of the invention should be administered to the subject. In certain embodiments, the kit further comprises at least one additional anticancer agent.

Combination Therapies

In certain embodiments, the compounds of the invention are useful in the methods of the invention in combination with at least one additional agent useful for treating or preventing cancer.

This additional agent may comprise compounds identified herein or compounds, e.g., commercially available compounds, known to treat, prevent or reduce the symptoms of cancer.

Non-limiting examples of additional agents contemplated within the invention include one or more of the following therapeutic agents: Erlotinib (TARCEVA®, Genentech/OSI Pharm.), docetaxel (TAXOTERE®, Sanofi-Aventis), 5-FU (fluorouracil, 5-fluorouracil, CAS No, 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), pemetrexed (ALIMTA®, Eli Lilly), trastuzumab (HERCEPTIN®, Genentech), temozolomide (4-methyl-5-oxo-2,3,4,6,8-pentazabicyclo[4.3.0]nona-2,7, 9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, rapamycin, oxaliplatin (ELOXATIN®, Sanofi), bortezomib (VELCADE®, Millennium Pharm.), carfilzomib (KYPROLIS®, Onyx), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, GlaxoSmithKline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®), ALK TKI inhibitors, antibodies such as avastin and cetuximab that target VEGFR and EGFR respectively, other RTK TKIs for PDGFR or RET, immunotherapies such as ipiliumimab and nivolumab, and radiation therapy.

A synergistic effect may be calculated, for example, using suitable methods such as, for example, the Sigmoid-Emax equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, in particular a mammal, more particularly a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is advantageous to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compounds/compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 □g to about 10,000 mg, about 20 □g to about 9,500 mg, about 40 □g to about 9,000 mg, about 75 □g to about 8,500 mg, about 150 □g to about 7,500 mg, about 200 □g to about 7,000 mg, about 3050 □-g to about 6,000 mg, about 500 □g to about 5,000 mg, about 750□g to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients, Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent may then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of a disease or disorder contemplated in the invention. Using a wax/pH-sensitive polymer mix, a gastric insoluble composition may be obtained in which the active ingredient is entrapped, ensuring its delayed release.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer, Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. In particular, it is advantageously present in an amount from about 0.0005% to about 5% of the composition; more particularly, it is advantageously present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject, Enema preparations may further comprise various additional ingredients including, but not limited to, antioxidants, and preservatives.

Additional Administration Forms

Additional dosage forms of this invention include dosage forms as described in U.S. Pat. Nos. 6,340,475; 6,488,962; 6,451,808; 5,972,389; 5,582,837; and 5,007,790, Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies advantageously within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Materials and Methods

All reactions were carried out in oven-dried glassware with dry solvent under an atmosphere of nitrogen unless indicated otherwise. Dry solvents were obtained using a solid-state solvent purification system provided at the Brown University Chemistry Department. Thin-layer chromatography was performed using pre-coated silica gel 60 plates and visualized by UV fluorescence quenching and stained with $KMnO_4$. Flash chromatography was performed using ZEOprep 60 silica gel (pore diameter 6 nm, particle size 40-63 μm). Yields refer to chromatographically pure compounds. $^1H$ and $^{13}C$ NMR spectra were recorded on a Bruker Avance III Ultra-Shield 400 MHz spectrometer for all intermediates and all final inhibitor analogs were recorded on a Bruker Avance III HD Ascend 600 MHz spectrometer. All chemical shifts are reported on a δ scale relative to the appropriate solvent peak. Multiplicities are described as follows: s (singlet), d (doublet), dd (doublet of doublets), t (triplet), q (quartet), quin (quintet), sext (sextet), m (multiplet). All high-resolution mass spectra were recorded using a JeolJ MS-600H spectrometer and an Agilent Technologies 6530 Accurate-Mass Q-TOFLC/MS.

Example 1: In Vitro Proteasome Inhibition Assay

Peptide hydrolysis by 2 nM human 20S (R&D Systems) was measured in 50 μL buffer R (20 mM HEPES-KOH pH 7.5, 0.5 mM EDTA) at 37° C. in the presence of various amounts of 20S inhibitors. Reaction components were pre-incubated for 20 min at 37° C. before adding 100 μM Suc-LLVY-Amc fluorogenic substrate (R&D Systems). Peptide cleavage was then followed continuously in Spectramax 5 spectrofluorimeter (Molecular Devices) by changes in fluorescence (excitation 380 nm; emission 440 nm). Peptide hydrolysis by 20 nM Mtb20S was measured as described above in buffer X (20 mM HEPES-KOH, pH 7.5, 0.5 mM EDTA, 5 mM $MgCl_2$).

Example 2: 20S Inhibition Kinetics

In vitro 20S peptidase inhibition assays were recorded in a 384-well plate at a SpectraMax M5 (Molecular devises) plate-reader. Therefore, 5 nM human 20S (R&D) was incubated in buffer R (50 mM HEPES-KOH, pH 7.5, 0.5 mM EDTA) with 100 μM of the fluorogenic peptide substrates Suc-LLVY-AMC or Boc-LRR-AMC. Reactions were started by adding various amounts of inhibitors (5 nM to 500 µM) to a final volume of 30 µL and peptide hydrolysis was continuously monitored for 90 min by changes in fluorescence (excitation 380 nm; emission 440 nm) at 37° C. The $k_{obs}$ values were determined by fitting the raw data to equation (1). The slopes of the plots of $k_{obs}$ versus I gave an apparent value of $k_{obs}/I$, also referred to as $k_{inact}/K_i$ for an irreversible inhibitor, which was then corrected by equation (2) to compensate for the effect of substrate competition, where app is the apparent value at different inhibitor concentrations.

$$P = v_s t + \frac{(v_0 - v_s)}{k_{obs}}[1 - e^{(-k_{obs}t)}] \quad \text{Equation 1}$$

$$k_{obs}/I = (k_{obs}/I)^{app}(1 + S/K_m) \quad \text{Equation 2}$$

Example 3: General Synthesis of Dipeptide Ureas

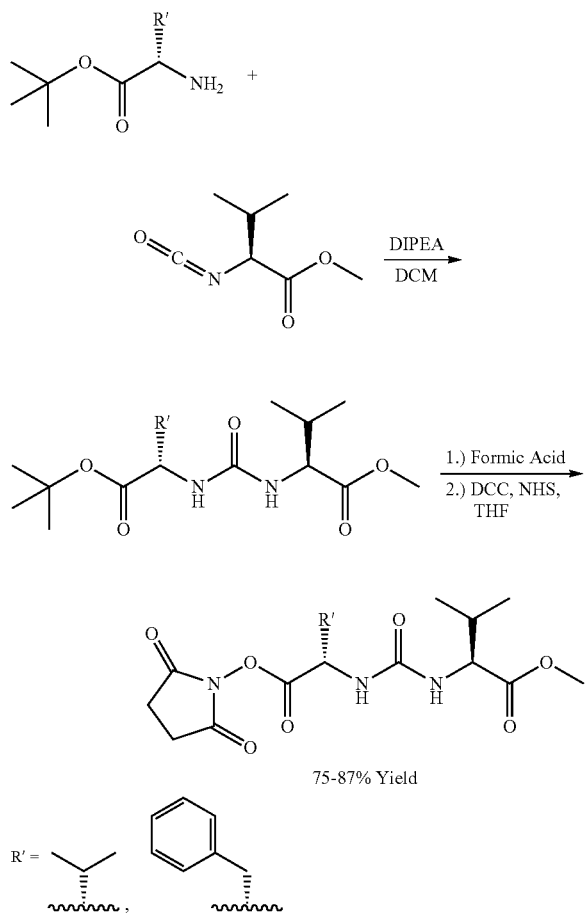

The appropriate tert-butyl amino acid (0.5 mmol) is dissolved in 1 mL of dichloromethane (DCM). To the solution was added the isocyanate (0.5 mmol), followed by the slow addition of DIPEA (174.2 µL, 1.0 mmol). The reaction mixture was stirred for 16 hours at room temperature. Then, the reaction was evaporated to dryness and diluted in 50 mL of ethyl acetate. The solution was washed with 1 M HCl (3×25 mL), water (1×25 mL), and brine. The organic layer was collected, dried with sodium sulfate and filtered. After concentrating, the urea was dissolved in formic acid (1131.9 µL, 30 mmol) and a few drops of water were added before stirring for 16 hours. The reaction was concentrated and toluene was added to azeotropically remove water. This resulting solid was dissolved in 2 mL of THF and placed into an ice bath. To the solution was added N-hydroxysuccinimide (63.3 mg, 0.55 mmol). A solution of DCC (123.8 mg, 0.6 mmol) in 1 mL THF was then slowly added and stirred for 16 hours at room temperature. The reaction was filtered through silica eluting with ethyl acetate. After concentrating, ethyl acetate was added and placed into a freezer for 15-20 minutes, then filtered again through silica before evaporating to dryness. The synthesis of the N,N-diethyl asparagine dipeptide urea was performed according to (Lin, et al., 2013, J. Am. Chem. Soc. 135:9968-9971. (See FIG. 3).

(S)-2,5-dioxopyrrolidin-1-yl-2-(3-((S)-1-methoxy-3-methyl-1-oxobutan-2-yl)ureido)-3-methylbutanoate

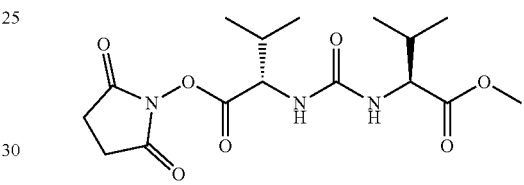

Yield: 87%; NMR $^1$H (400 MHz, CDCl$_3$): δ 5.69-5.63 (dd, 2H), 4.83-4.79 (dd, 1H), 4.48-4.45 (dd, 1H), 3.75 (s, 3H), 2.84 (s, 4H), 2.31-2.23 (m, 1H), 2.15-2.07 (m, 1H), 1.03-1.02 (d, 3H), 1.00-0.98 (d, 3H), 0.95-0.93 (d, 3H), 0.87-0.86 (d, 3H); $^{13}$C (100 MHz, CDCl$_3$): δ 174.50, 168.87, 168.72, 156.96, 58.04, 56.39, 52.30, 31.79, 31.47, 25.60, 18.96, 18.69, 17.74, 17.35; HRMS (m/z): [M+H]$^+$ calcd., 372.1771; found, 372.1758.

(S)-methyl-2-(3-((S)-1-((2,5-dioxopyrrolidin-1-yl)oxy)-1-oxo-3-phenylpropan-2-yl)ureido)-3-methylbutanoate

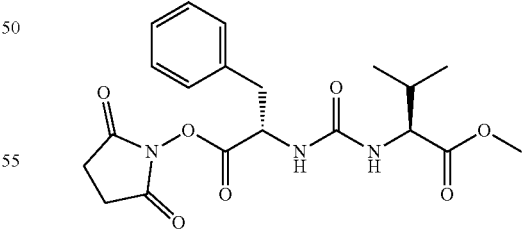

Yield: 75%; NMR $^1$H (400 MHz, CDCl$_3$): δ 7.30-7.29 (m, 5H), 5.71-5.68 (d, 1H), 5.47-5.44 (d, 1H), 5.26-5.21 (m, 1H), 4.48-4.45 (dd, 1H), 3.60 (s, 3H), 3.26-3.25 (d, 2H), 2.84 (s, 4H), 2.12-2.04 (m, 1H), 0.93-0.92 (d, 3H), 0.85-0.83 (d, 3H); $^{13}$C (100 MHz, CDCl$_3$): δ 174.29, 172.24, 168.85, 168.21, 157.43, 134.83, 129.99, 128.55, 127.26, 57.91, 52.30, 52.06, 38.27, 31.47, 25.60, 25.39, 18.92, 17.67, HRMS (m/z): [M+Na]$^+$ calcd., 442.1590; found, 442.1584.

Example 4: General Synthesis of Linear Peptide Macrocyclic Precursors

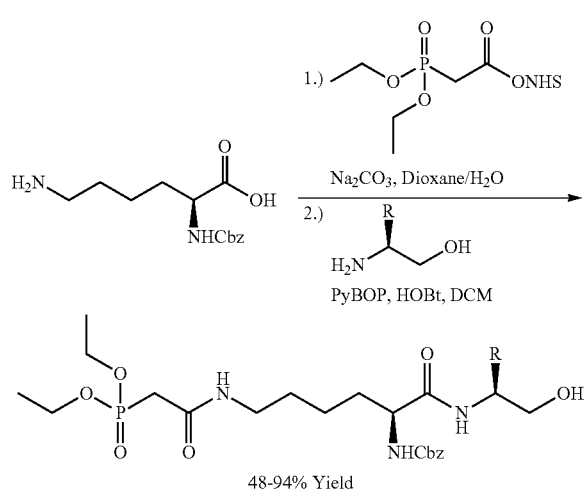

2-(((benzyloxy)carbonyl)amino)-6-(2-(diethoxyphosphoryl)acetamido)hexanoic acid was synthesized as reported in Pirrung, et al., 2010, Org. Lett. 12:2402-2405. This intermediate (458.4 mg, 1.0 mmol) was dissolved in 5 mL of DCM and placed into an ice bath. HOBt (183.7 mg, 1.2 mmol) and PyBOP (624.5 mg, 1.2 mmol) were added to the mixture, followed by the appropriate amino alcohol (1.1 mmol), which was prepared according to McKennon, et al., 1993, J. Org. Chem. 58:3568-3571. After stirring for 5 minutes in the ice bath, DIPEA (261.3 µL, 1.5 mmol) was slowly added before stirring at room temperature for 16 hours. Then, the reaction was evaporated and redissolved in 100 mL of ethyl acetate. The solution was washed with 1 M HCl (3×50 mL), water (1×50 mL) and brine. The organic layer was collected, dried with sodium sulfate and evaporated before TLC and flash chromatography. TLC conditions—Acetone:DCM, 3:1 v/v. (See FIG. 2)

Benzyl (6-(2-(diethoxyphosphoryl)acetamido)-1-(((S)-1-hydroxy-3-methylbutan-2-yl)amino)-1-oxohexan-2-yl)carbamate

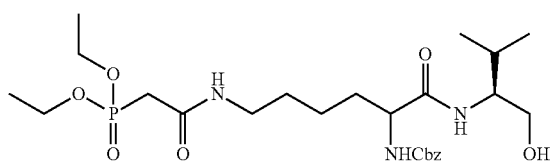 [SMILES: CCOP(=O)(CC(=O)NCCCCC(NC(=O)OCc1ccccc1)C(=O)N[C@H](CO)C(C)C)OCC]

Yield: 55%; NMR $^1$H (400 MHz, CDCl$_3$): δ 7.36-7.34 (m, 5H), 6.97-6.94 (t, 1H), 6.66-6.64 (d, 1H), 5.89-5.87 (d, 1H), 5.10 (s, 2H), 4.19-4.09 (m, 5H), 3.75-3.63 (m, 3H), 3.30-3.26 (m, 2H), 3.14-3.12 (sext, 1H), 2.87 (s, 1H), 2.82 (s, 1H), 1.89-1.79 (m, 3H), 1.76-1.69 (m, 1H), 1.56-1.52 (m, 2H), 1.46-1.41 (m, 2H), 1.35-1.32 (t, 6H), 0.96-0.91 (dd, 6H); $^{13}$C (100 MHz, CDCl$_3$): δ 171.97, 164.23, 156.21, 136.35, 128.50, 128.13, 128.02, 66.86, 63.04, 62.98, 62.93, 62.79, 57.05, 46.30, 38.99, 29.07, 28.53, 26.42, 22.18, 19.45, 19.06, 16.34, 16.28; HRMS (m/z): [M+Na]$^+$ calcd., 566.2607; found, 566.2625.

Benzyl (6-(2-(diethoxyphosphoryl)acetamido)-1-(((S)-1-hydroxy-4-methylpentan-2-yl)amino)-1-oxohexan-2-yl)carbamate

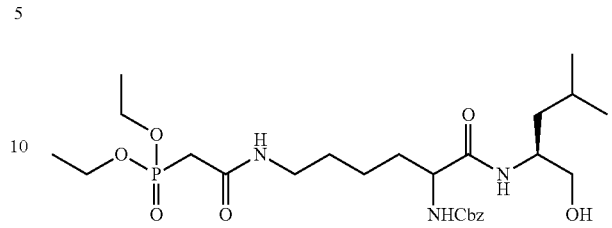

Yield: 78%; NMR $^1$H (400 MHz, CDCl$_3$): δ 7.30-7.27 (m, 5H), 7.11 (bs, 1H), 6.85 (bs, 1H), 6.24 (bs, 1H), 5.04 (s, 2H), 4.12-4.04 (m, 6H), 3.60-3.59 (d, 1H), 3.39 (bs, 1H), 3.22-3.12 (m, 2H), 2.91-2.88 (d, 2H), 1.60-1.56 (m, 2H), 1.47 (m, 2H), 1.34 (m, 3H), 1.26-1.18 (m, 7H), 0.87-0.83 (dd, 6H); $^{13}$C (100 MHz, CDCl$_3$): δ 173.06, 165.59, 156.47, 136.24, 128.49, 128.13, 127.96, 66.89, 65.41, 63.12, 55.44, 49.82, 46.27, 46.24, 30.92, 26.37, 26.32, 24.67, 22.95, 22.01, 16.16, 16.13; HRMS (m/z): [M+H]$^+$ calcd., 558.2944; found, 558.2927.

Benzyl (6-(2-(diethoxyphosphoryl)acetamido)-1-(((S)-1-hydroxy-3-phenylpropan-2-yl)amino)-1-oxohexan-2-yl)carbamate

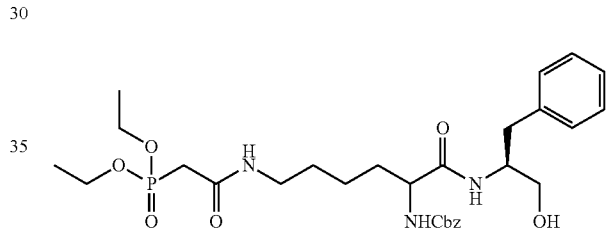

Yield: 66%; NMR $^1$H (400 MHz, CDCl$_3$): δ 7.38-7.29 (m, 5H), 7.24-7.16 (m, 6H), 6.11-6.09 (d, 1H), 5.10-5.04 (s, 2H), 4.18-4.13 (m, 2H), 4.12-4.05 (q, 4H), 3.64-3.62 (m, 1H), 3.53-3.49 (m, 1H), 3.21-3.19 (m, 2H), 2.89-2.82 (m, 4H), 1.76-1.72 (m, 1H), 1.67-1.62 (m, 1H), 1.47-1.46 (m, 2H), 1.36-1.34 (m, 1H), 1.31-1.28 (t, 6H); $^{13}$C (100 MHz, CDCl3): δ 172.00, 164.45, 156.27, 138.09, 136.38, 129.32, 128.51, 128.40, 128.13, 127.99, 126.38, 66.83, 62.98, 62.92, 62.85, 55.07, 52.93, 39.18, 37.02, 35.79, 34.47, 32.26, 28.56, 22.29, 16.34, 16.28; HRMS (m/z): [M+Na]$^+$ calcd., 614.2607; found, 614.2628.

Benzyl (6-(2-(diethoxyphosphoryl)acetamido)-1-(((S)-1-hydroxy-3-(3-(trifluoromethyl)phenyl) propan-2-yl)amino)-1-oxohexan-2-yl)carbamate

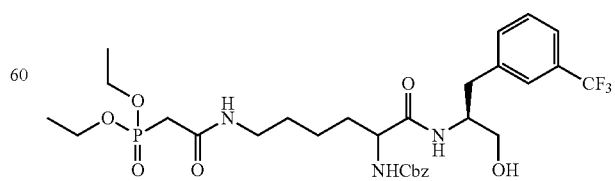

Yield: 67%; NMR $^1$H (400 MHz, CDCl$_3$): δ 7.49-7.36 (m, 4H), 7.32-7.23 (m, 6H), 7.19-7.17 (t, 1H), 6.14-6.13 (d, 1H), 5.06-5.00 (s, 2H), 4.17-4.11 (m, 2H), 4.12-4.05 (q, 4H), 3.61-3.60 (m, 1H), 3.51-3.47 (m, 1H), 3.20-3.15 (m, 2H), 2.92-2.87 (m, 2H), 2.85-2.81 (d, 1H), 1.74-1.68 (m, 1H), 1.65-1.57 (m, 1H), 1.48-1.42 (m, 2H), 1.35-1.29 (m, 2H), 1.27-1.25 (t, 6H); $^{13}$C (100 MHz, CDCl$_3$): δ 172.17, 164.53, 156.25, 139.36, 136.35, 132.83, 128.79, 128.46, 128.08, 127.92, 126.00, 123.17, 66.76, 62.88, 62.82, 62.75, 55.13, 52.71, 46.30, 39.13, 36.66, 35.73, 34.43, 32.31, 28.51, 26.39, 16.27, 16.21; HRMS (m/z): [M+Na]$^+$ calcd., 682.2481; found, 682.2462.

Benzyl (6-(2-(diethoxyphosphoryl)acetamido)-1-(((S)-1-(2-fluorophenyl)-3-hydroxypropan-2-yl) amino)-1-oxohexan-2-yl)carbamate

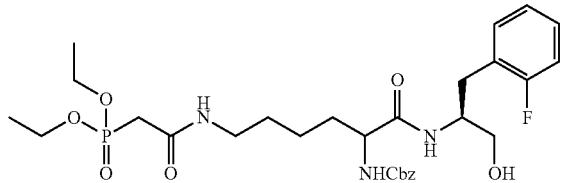 [SMILES: CCOP(=O)(CC(=O)NCCCCC(NC(=O)OCc1ccccc1)C(=O)N[C@H](CO)Cc1ccccc1F)OCC]

Yield: 60%; NMR $^1$H (400 MHz, CDCl$_3$): δ 7.85-7.83 (d, 1H), 7.68-7.67 (d, 1H), 7.38-7.30 (m, 5H), 7.25-7.23 (t, 1H), 7.19-7.16 (q, 1H), 7.05-7.02 (t, 1H), 7.01-6.98 (t, 1H), 6.93-6.92 (t, 1H), 6.85-6.84 (d, 1H), 5.80-5.79 (d, 1H), 5.10 (s, 2H), 4.25-4.22 (m, 1H), 4.15-4.08 (m, 5H), 3.72-3.71 (d, 1H), 3.56-3.53 (dd, 1H), 3.28-3.22 (m, 2H), 2.92-2.90 (d, 2H), 2.86 (s, 1H), 2.83 (s, 1H), 1.80-1.76 (m, 1H), 1.68-1.63 (m, 1H), 1.53-1.49 (m, 2H), 1.40-1.35 (m, 2H), 1.34-1.32 (t, 6H); $^{13}$C (100 MHz, CDCl$_3$): δ 171.70, 164.23, 160.49, 156.13, 136.37, 131.60, 128.51, 128.27, 128.13, 128.00, 127.92, 126.00, 124.86, 124.10, 115.27, 66.86, 63.40, 63.03, 62.99, 62.93, 55.02, 52.07, 46.29, 39.04, 35.58, 34.71, 32.18, 30.25, 29.51, 28.51, 22.10, 16.30, 16.27; HRMS (m/z): [M+H]$^+$ calcd., 610.2694; found, 610.2691.

Benzyl (6-(2-(diethoxyphosphoryl)acetamido)-1-(((S)-1-(3-fluorophenyl)-3-hydroxypropan-2-yl) amino)-1-oxohexan-2-yl)carbamate

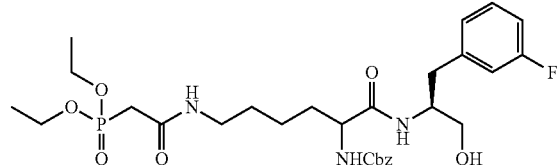 [SMILES: CCOP(=O)(CC(=O)NCCCCC(NC(=O)OCc1ccccc1)C(=O)N[C@H](CO)Cc1cccc(F)c1)OCC]

Yield: 48%; NMR $^1$H (400 MHz, CDCl$_3$): δ 7.33-7.32 (m, 1H), 7.30-7.25 (m, 5H), 7.18-7.13 (m, 2H), 6.97-6.96 (d, 1H), 6.93-6.92 (d, 1H), 6.84-6.81 (t, 1H), 6.15-6.14 (d, 1H), 5.07-5.01 (q, 2H), 4.15-4.11 (m, 2H), 4.09-4.05 (q, 4H), 3.60-3.59 (d, 1H), 3.51-3.47 (m, 1H), 3.19-3.15 (m, 2H), 2.87-2.78 (m, 4H), 1.74-1.69 (m, 1H), 1.64-1.60 (m, 1H), 1.47-1.41 (m, 2H), 1.35-1.30 (m, 2H), 1.28-1.25 (t, 6H); $^{13}$C (100 MHz, CDCl$_3$): δ 172.07, 164.45, 163.53, 161.91, 156.25, 140.88, 136.38, 129.78, 129.72, 128.45, 128.06, 127.93, 126.03, 125.00, 116.23, 113.22, 66.77, 62.90, 62.85, 62.81, 55.09, 52.70, 46.29, 39.17, 36.66, 35.54, 34.66, 32.21, 28.55, 26.36, 26.31, 22.33, 16.27, 16.24; HRMS (m/z): [M+Na]$^+$ calcd., 632.2513; found, 632.2538.

Benzyl (6-(2-(diethoxyphosphoryl)acetamido)-1-(((S)-1-(3,5-difluorophenyl)-3-hydroxy propan-2-yl) amino)-1-oxohexan-2-yl)carbamate

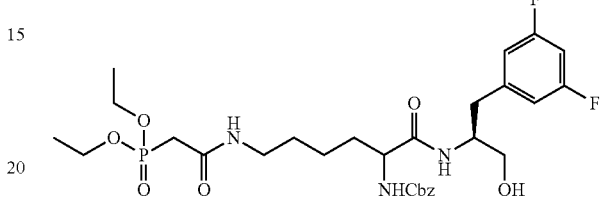

Yield: 73%; NMR $^1$H (400 MHz, CDCl$_3$): δ 7.36-7.31 (m, 5H), 7.19-7.17 (m, 1H), 7.00-6.97 (d, 1H), 6.80-6.79 (d, 2H), 6.67-6.62 (t, 1H), 5.92-5.90 (d, 1H), 5.09-5.08 (d, 2H), 4.15-4.09 (m, 6H), 3.68-3.65 (d, 1H), 3.54-3.50 (m, 1H), 3.32-3.19 (m, 2H), 2.88-2.82 (m, 4H), 1.79-1.74 (m, 2H), 1.69-1.63 (m, 1H), 1.52-1.48 (m, 2H), 1.41-1.38 (m, 2H), 1.35-1.31 (t, 6H); $^{13}$C (100 MHz, CDCl$_3$): δ 171.82, 164.37, 164.33, 161.73, 156.21, 142.19, 136.31, 128.51, 128.16, 128.01, 112.29, 112.04, 101.89, 66.90, 63.03, 62.96, 62.74, 55.02, 52.47, 46.33, 38.99, 36.73, 35.80, 34.49, 32.27, 28.48, 26.43, 26.35, 22.24, 16.33, 16.27; HRMS (m/z): [M+Na]$^+$ calcd., 650.2419; found, 650.2436.

Benzyl (1-(((S)-1-(2-chlorophenyl)-3-hydroxypropan-2-yl)amino)-6-(2-(diethoxyphosphoryl) acetamido)-1-oxohexan-2-yl)carbamate

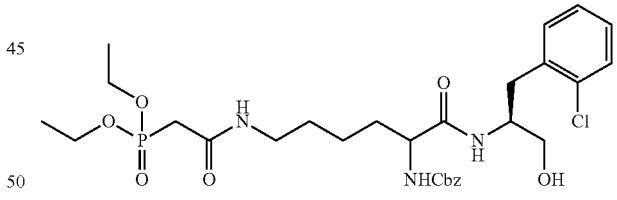

Yield: 80%; NMR $^1$H (400 MHz, CDCl$_3$): δ 7.36-7.31 (m, 6H), 7.30-7.28 (t, 2H), 7.15-7.12 (m, 2H), 7.03-7.01 (m, 2H), 5.85-5.84 (d, 1H), 5.09 (s, 2H), 4.32-4.28 (m, 1H), 4.15-4.08 (m, 5H), 3.73-3.71 (d, 1H), 3.59-3.55 (dd, 1H), 3.27-3.23 (m, 2H), 3.02-3.00 (d, 2H), 2.88 (s, 1H), 2.83 (s, 1H), 1.79-1.74 (m, 2H), 1.69-1.62 (m, 1H), 1.52-1.46 (m, 2H), 1.41-1.36 (m, 2H), 1.34-1.31 (t, 6H); $^{13}$C (100 MHz, CDCl$_3$): δ 171.70, 164.31, 164.28, 156.14, 136.35, 135.91, 134.28, 131.52, 129.44, 128.52, 128.15, 128.00, 126.82, 66.84, 63.44, 63.04, 62.96, 62.90, 55.02, 51.80, 46.27, 39.04, 35.80, 34.61, 32.25, 28.50, 26.42, 26.34, 22.11, 16.35, 16.28; HRMS (m/z): [M+H]$^+$ calcd., 626.2398; found, 626.2415.

Benzyl (1-(((S)-1-(3-chlorophenyl)-3-hydroxypropan-2-yl)amino)-6-(2-(diethoxyphosphoryl) acetamido)-1-oxohexan-2-yl)carbamate

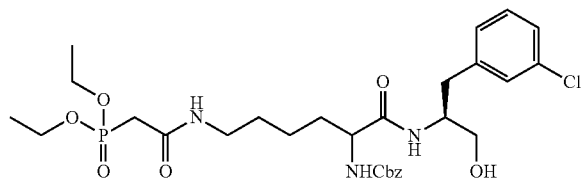 [SMILES: CCOP(=O)(CC(=O)NCCCCC(NC(=O)OCc1ccccc1)C(=O)N[C@H](CO)Cc1cccc(Cl)c1)OCC]

Yield: 66%; NMR ¹H (400 MHz, CDCl₃): δ 7.39-7.33 (m, 5H), 7.25-7.19 (m, 3H), 7.15-7.12 (m, 1H), 6.89-6.84 (m, 2H), 5.81-5.79 (d, 1H), 5.11 (s, 2H), 4.18-4.07 (m, 6H), 3.70-3.67 (d, 1H), 3.53-3.49 (dd, 1H), 3.36-3.30 (m, 1H), 3.28-3.21 (m, 1H), 2.88-2.83 (m, 4H), 1.83-1.77 (m, 1H), 1.72-1.64 (m, 1H), 1.57-1.49 (m, 2H), 1.45-1.38 (m, 2H), 1.36-1.32 (t, 6H); ¹³C (100 MHz, CDCl₃): δ 171.65, 164.25, 156.15 140.17, 136.33, 134.13, 129.71, 129.44, 128.33, 128.17, 128.05, 127.52, 126.64, 66.90, 63.08, 63.01, 62.78, 55.06, 52.65, 38.95, 35.83, 34.53, 32.26, 28.49, 22.15, 16.35, 16.29; HRMS (m/z): [M+Na]⁺ calcd., 648.2218; found, 648.2236.

Benzyl (1-(((S)-1-(4-chlorophenyl)-3-hydroxypropan-2-yl)amino)-6-(2-(diethoxyphosphoryl) acetamido)-1-oxohexan-2-yl)carbamate

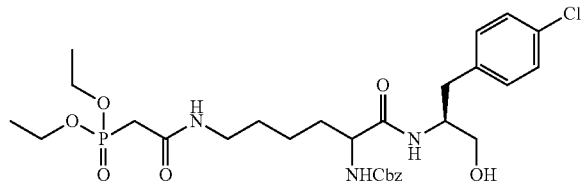 [SMILES: CCOP(=O)(CC(=O)NCCCCC(NC(=O)OCc1ccccc1)C(=O)N[C@H](CO)Cc1ccc(Cl)cc1)OCC]

Yield: 94%; NMR H (400 MHz, CDCl₃): δ 7.75-7.73 (d, 1H), 7.62-7.60 (d, 1H), 7.37-7.31 (m, 5H), 7.25-7.19 (m, 2H), 7.18-7.14 (m, 3H), 7.11-7.09 (t, 1H), 5.92-5.90 (d, 1H), 5.08-5.07 (s, 2H), 4, 15-4.07 (m, 6H), 3.68-3.58 (m, 1H), 3.52-3.48 (dd, 1H), 3.37-3.20 (m, 2H), 2.89-2.80 (m, 4H), 1.77-1.69 (m, 1H), 1.68-1.61 (m, 1H), 1.51-1.45 (m, 2H), 1.39-1.35 (m, 2H), 1.34-1.29 (t, 6H); ¹³C (100 MHz, CDCl₃): δ 171.83, 164.33, 156.22, 142.83, 136.61, 136.28, 132.15, 130.72, 126.88, 128.53, 128.48, 128.17, 128.00, 125.33, 124.64, 66.90, 63.07, 62.97, 62.82, 55.03, 52.78, 46.27, 39.00, 36.33, 34.46, 32.30, 28.45, 22.21, 16.34, 16.27; HRMS (m/z): [M+H]⁺ calcd., 626.2398; found, 626.2395.

Benzyl (6-(2-(diethoxyphosphoryl)acetamido)-1-(((S)-1-hydroxy-3-(m-tolyl)propan-2-yl)amino)-1-oxohexan-2-yl) carbamate

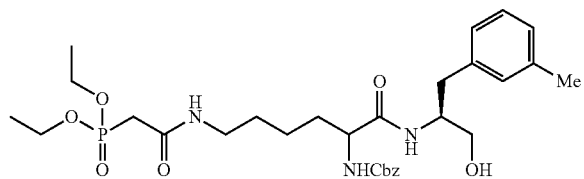 [SMILES: CCOP(=O)(CC(=O)NCCCCC(NC(=O)OCc1ccccc1)C(=O)N[C@H](CO)Cc1cccc(C)c1)OCC]

Yield: 63%; NMR ¹H (400 MHz, CDCl3): δ 7.35-7.28 (m, 5H), 7.20-7.10 (m, 3H), 7.05-6.97 (m, 3H), 6.12-6.10 (d, 1H), 5.07 (s, 2H), 4.18-4.04 (m, 6H), 3.63-3.61 (d, 1H), 3.53-3.48 (dd, 1H), 3.24-3.16 (m, 2H), 2.89-2.77 (m, 4H), 2.28 (s, 3H), 1.79-1.70 (m, 1H), 1.68-1.63 (m, 1H), 1.51-1.41 (m, 2H), 1.38-1.32 (m, 2H), 1.30-1.27 (t, 6H); ¹³C (100 MHz, CDCl₃): δ 172.02, 164.56, 156.24, 138.00, 137.92, 136.38, 130.07, 128.49, 128.26, 128.11, 127.97, 127.12, 126.32, 66.80, 63.08, 62.95, 62.90, 62.83, 55.11, 52.99, 46.27, 39.13, 36.91, 32.31, 28.58, 26.42, 21.34, 16.33, 16.26; HRMS (m/z): [M+H]⁺ calcd., 606.2944; found, 606.2937.

Benzyl (6-(2-(diethoxyphosphoryl)acetamido)-1-(((S)-1-hydroxy-3-(p-tolyl)propan-2-yl)amino)-1-oxohexan-2-yl)carbamate

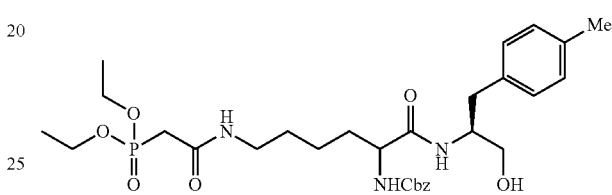

Yield: 66%; NMR ¹H (400 MHz, CDCl₃): δ 7.34-7.26 (m, 6H), 7.10-7.08 (d, 2H), 7.04-7.02 (m, 2H), 6.18-6.16 (d, 1H), 5.06 (s, 2H), 4.18-4.04 (m, 6H), 3.62-3.60 (d, 1H), 3.51-3.47 (dd, 1H), 3.19-3.18 (d, 2H), 2.87-2.78 (m, 4H), 2.26 (s, 3H), 1.78-1.70 (m, 1H), 1.67-1.62 (m, 1H), 1.50-1.42 (m, 2H), 1.38-1.32 (m, 2H), 1.30-1.26 (t, 6H); ¹³C (100 MHz, CDCl₃): δ 171.99, 164.44, 156.25, 136.40, 135.72, 135.00, 129.19, 129.06, 128.48, 128.08, 127.94, 66.76, 62.92, 62.85, 62.76, 55.06, 53.02, 46.32, 39.19, 36.56, 32.32, 28.57, 26.42, 21.01, 16.34, 16.27; HRMS (m/z): [M+H]⁺ calcd., 606.2944; found, 606.2952.

Benzyl (6-(2-(diethoxyphosphoryl)acetamido)-1-(((S)-1-hydroxy-3-(1H-indol-3-yl)propan-2-yl)amino)-1-oxohexan-2-ylcarbamate

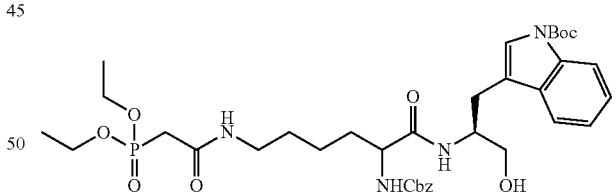

Yield: 75%; NMR ¹H (400 MHz, CDCl₃): δ 8.13-8.11 (m, 1H), 7.71-7.69 (d, 1H), 7.48 (s, 1H), 7.38-7.28 (m, 6H), 7.27-7.23 (t, 1H), 6.93-6.91 (d, 1H), 6.86-6.84 (d, 1H), 5.84-5.82 (d, 1H), 5.10 (s, 2H), 4.36-4.26 (m, 1H), 4.19-4.07 (m, 5H), 3.74-3.71 (d, 1H), 3.61-3.57 (m, 1H), 3.35-3.31 (m, 1H), 3.26-3.20 (m, 1H), 3.00-2.94 (m, 1H), 2.86 (s, 1H), 2.81 (s, 1H), 1.85-1.77 (m, 2H), 1.75-1.65 (m, 10H), 1.56-1.52 (m, 2H), 1.46-1.38 (m, 2H), 1.35-1.28 (m, 6H); ¹³C (100 MHz, CDCl₃): δ 171.75, 164.23, 156.12, 149.76, 136.35, 130.65, 128.50, 128.13, 128.03, 124.42, 123.89, 122.61, 119.31, 116.93, 115.18, 83.57, 66.88, 63.06, 62.99, 62.98, 55.09, 51.45, 46.30, 39.00, 32.43, 28.47, 28.22, 26.55, 22.17, 16.32, 16.26; HRMS (m/z): [M+H]⁺ calcd., 731.3421; found, 731.3408.

Example 5: General Procedure for Horner-Emmons-Wadsworth Macrocyclization

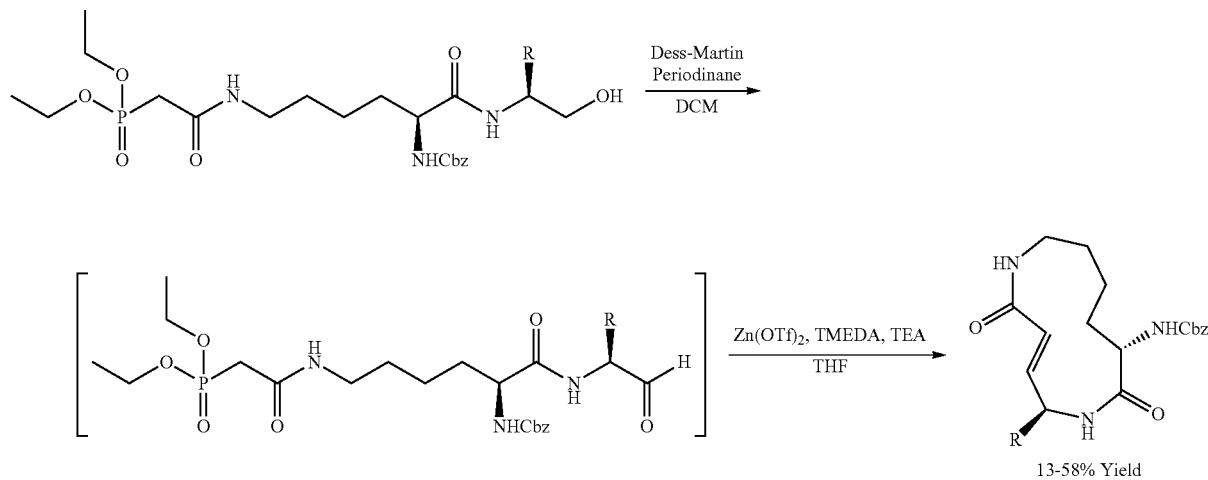

The linear peptide (0.9 mmol) was dissolved in 10 mL of DCM and Dess-Martin periodinane (420 mg, 0.99 mmol) was added. After stirring at room temperature for 90 minutes, the reaction was diluted in 100 mL of ethyl acetate. The organic solution was then washed with 1:1 mixture of saturated sodium bicarbonate and 2% $Na_2S_2O_3$ (2×50 mL). The organic phase was collected, dried, filtered and concentrated, which was used without further purification. TMEDA (162 μL, 1.08 mmol) and TEA (502 μL, 3.6 mmol) was added to a solution of $Zn(OTf)_2$ (720 mg, 1.98 mmol) in 200 mL of THF. The solution was stirred for 15-20 minutes before adding the linear peptide in 100 mL of THF to a pressure-equalizing addition funnel. The solution in the funnel was added dropwise to the reaction over 2 hours. The reaction was stirred for 20 hours at room temperature before concentrating and redissolving in 100 mL of ethyl acetate. Then, the solution was washed with 1 M HCl (1×50 mL), water (1×50 mL) and brine. Once the organic phase was collected, dried, filtered and concentrated. The resulting oil was purified via flash chromatography, yielding a white or yellow solid. In certain embodiments, pure macrocycle can be achieved in the case of yellow-colored macroacycles by redissolving in a small amount of MeOH and placing the solution into the freezer for 15 minutes, followed by filtration. (See FIG. 2).

Benzyl ((5S,8S,E)-5-isopropyl-2,7-dioxo-1,6-diazacyclododec-3-en-8-yl)carbamate

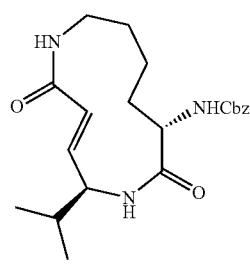 [SMILES: CC(C)[C@H]1/C=C/C(=O)NCCCC[C@H](NC(=O)OCc2ccccc2)C(=O)N1]

Yield: 58%; NMR $^1$H (400 MHz, DMSO-$d_6$): δ 8.25-8.23 (d, 1H), 7.41-7.31 (m, 6H), 7.12-7.11 (d, 1H), 6.80-6.76 (dd, 1H), 6.23-6.20 (d, 1H), 5.01 (s, 2H), 4.41-4.40 (m, 1H), 4.14-4.10 (q, 1H), 3.30-3.24 (m, 1H), 2.95-2.93 (d, 1H), 2.15-2.10 (m, 1H), 1.79-1.75 (m, 1H), 1.58-1.53 (m, 1H), 1.43-1.41 (m, 2H), 1.27-1.23 (m, 1H), 0.97-0.96 (d, 3H), 0.93-0.92 (d, 3H); $^{13}$C (100 MHz, DMSO-$d_6$): δ 171.64, 166.25, 155.94, 145.40, 137.52, 128.80, 128.24, 128.16, 120.24, 65.78, 56.44, 53.64, 46.19, 40.50, 38.37, 31.65, 30.75, 30.65, 20.39, 19.76, 17.69; HRMS (m/z): [M+H]$^+$ calcd., 388.2236; found, 388.2235.

Benzyl ((5S,8S,E)-5-isobutyl-2,7-dioxo-1,6-diazacyclododec-3-en-8-yl)carbamate

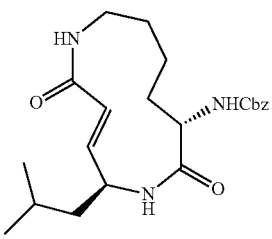 [SMILES: CC(C)C[C@H]1/C=C/C(=O)NCCCC[C@H](NC(=O)OCc2ccccc2)C(=O)N1]

Yield: 39%; NMR $^1$H (400 MHz, DMSO-$d_6$): δ 8.31-8.29 (d, 1H), 7.39-7.33 (m, 5H), 7.32-7.31 (m, 1H), 7.08-7.06 (d, 1H), 6.78-6.76 (dd, 1H), 6.27-6.25 (d, 1H), 5.02 (s, 2H), 4.39-4.34 (m, 2H), 3.30-3.24 (m, 1H), 2.96-2.94 (m, 1H), 2.17-2.13 (t, 1H), 1.70-1.64 (sext, 1H), 1.60-1.56 (t, 1H), 1.43-1.38 (m, 4H), 1.27-1.23 (t, 1H), 0.93-0.92 (m, 4H), 0.88-0.87 (d, 3H); $^{13}$C (100 MHz, DMSO-$d_6$): δ 171.56, 166.35, 155.94, 146.58, 137.50, 128.79, 128.23, 128.15, 127.68, 68.81, 53.75, 48.69, 46.25, 42.10, 38.38, 30.77, 30.51, 25.34, 23.22, 22.20, 17.70, 9.12; HRMS (m/z): [M+H]$^+$ calcd., 402.2393; found, 402.2392.

Benzyl ((5S,8S,E)-5-benzyl-2,7-dioxo-1,6-diazacyclododec-3-en-8-yl)carbamate

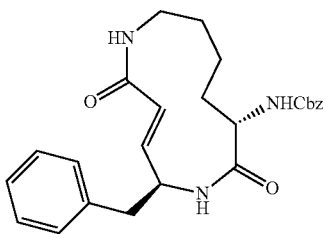 [SMILES: O=C1/C=C/[C@H](Cc2ccccc2)NC(=O)[C@@H](NC(=O)OCc2ccccc2)CCCCN1]

Yield: 20%; NMR $^1$H (400 MHz, DMSO-d6): δ 8.44-8.43 (d, 1H), 7.41-7.22 (m, 12H), 7.08-7.07 (d, 1H), 6.77-6.74 (dd, 1H), 6.35-6.32 (d, 1H), 5.01-4.97 (s, 2H), 4.61 (m, 1H), 4.33-4.32 (m, 1H), 2.99-2.97 (m, 1H), 2.92-2.89 (dd, 1H), 2.76-2.72 (dd, 1H), 2.22-2.17 (t, 1H), 1.60-1.56 (m, 1H), 1.45-1.43 (m, 2H), 1.28-1.19 (m, 2H), 0.93-0.91 (q, 1H); $^{13}$C (100 MHz, DMSO-d$_6$): δ 171.63, 166.20, 155.92, 145.90, 138.84, 137.46, 129.37, 128.78, 128.21, 128.14, 126.85, 119.92, 65.81, 53.73, 52.18, 40.55, 38.87, 38.35, 30.76, 30.56, 17.66; HRMS (m/z): [M+Na]$^+$ calcd., 458.2056; found, 458.2056.

Benzyl ((5S,8S,E)-2,7-dioxo-5-(3-(trifluoromethyl)benzyl)-1,6-diazacyclododec-3-en-8-yl) carbamate

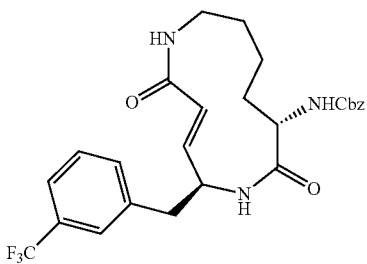 [SMILES: O=C1/C=C/[C@H](Cc2cccc(C(F)(F)F)c2)NC(=O)[C@@H](NC(=O)OCc2ccccc2)CCCCN1]

Yield: 25%; NMR $^1$H (400 MHz, DMSO-d$_6$): δ 8.47-8.46 (d, 1H), 7.71 (s, 1H), 7.65-7.55 (m, 3H), 7.43-7.41 (t, 1H), 7.36-7.30 (m, 5H), 7.10-7.09 (d, 1H), 6.82-6.78 (dd, 1H), 6.36-6.33 (d, 1H), 4.98 (s, 2H), 4.63 (m, 1H), 4.31 (m, 1H), 3.30-3.25 (m, 1H), 3.07-3.04 (dd, 1H), 2.99-2.97 (m, 1H), 2.79-2.75 (dd, 1H), 2.20-2.16 (t, 1H), 1.60-1.58 (m, 1H), 1.45-1.43 (m, 2H), 1.29-1.25 (m, 1H), 0.92-0.90 (q, 1H); $^{13}$C (100 MHz, DMSO-d$_6$): δ 171.63, 166.20, 155.92, 145.90, 138.84, 137.46, 129.37, 128.78, 128.21, 128.14, 126.85, 119.92, 65.81, 53.73, 52.18, 40.55, 38.87, 38.35, 30.76, 30.56, 17.66; HRMS (m/z): [M+Na]+ calcd., 526.1930; found, 526.1948.

Benzyl ((5S,8S,E)-5-(2-fluorobenzyl)-2,7-dioxo-1,6-diazacyclododec-3-en-8-yl)carbamate

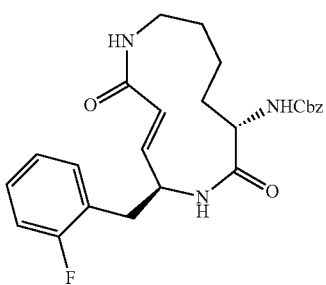 [SMILES: O=C1/C=C/[C@H](Cc2ccccc2F)NC(=O)[C@@H](NC(=O)OCc2ccccc2)CCCCN1]

Yield: 22%; NMR $^1$H (400 MHz, DMSO-d$_6$): δ 8.46-8.45 (d, 1H), 7.41-7.38 (m, 2H), 7.36-7.33 (m, 4H), 7.32-7.29 (m, 2H), 7.20-7.17 (m, 2H), 7.11-7.10 (d, 1H), 6.71-6.67 (dd, 1H), 6.37-6.35 (d, 1H), 5.00 (s, 2H), 4.66 (m, 1H), 4.30 (m, 1H), 3.30-3.28 (m, 1H), 2.98-2.94 (m, 2H), 2.84-2.80 (dd, 1H), 2.22-2.21 (t, 1H), 1.60-1.56 (m, 1H), 1.45-1.43 (m, 2H), 1.29-1.24 (m, 1H), 0.94-0.88 (q, 1H); $^{13}$C (100 MHz, DMSO-d$_6$): δ 171.72, 166.15, 160.23, 155.94, 145.04, 137.46, 131.77, 128.78, 128.22, 128.15, 124.88, 120.49, 115.75, 65.82, 53.80, 50.68, 40.55, 38.36, 32.07, 30.76, 30.44, 17.72; HRMS (m/z): [M+H]$^+$ calcd., 454.2142; found, 454.2138.

Benzyl ((5S,8S,E)-5-(3-fluorobenzyl)-2,7-dioxo-1,6-diazacyclododec-3-en-8-yl)carbamate

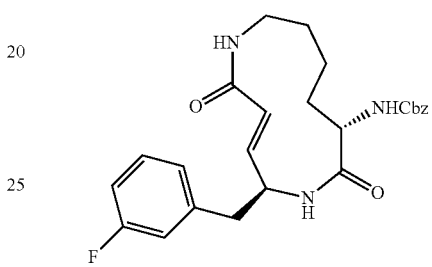

Yield: 39%; NMR $^1$H (400 MHz, DMSO-d$_6$): δ 8.44-8.43 (d, 1H), 7.42-7.40 (t, 1H), 7.37-7.33 (m, 4H), 7.32-7.30 (m, 1H), 7.18-7.15 (m, 2H), 7.11-7.10 (d, 1H), 7.07-7.05 (t, 1H), 6.78-6.75 (dd, 1H), 6.34-6.32 (d, 1H), 4.99 (s, 2H), 4.61 (m, 1H), 4.32-4.31 (m, 1H), 3.32-3.28 (m, 1H), 2.99-2.93 (m, 2H), 2.74-2.70 (dd, 1H), 2.20-2.16 (t, 1H), 1.61-1.56 (m, 1H), 1.46-1.41 (m, 2H), 1.29-1.22 (m, 1H), 0.94-0.88 (q, 1H); $^{13}$C (100 MHz, DMSO-d$_6$): δ 171.69, 166.16, 161.78, 155.93, 145.65, 137.45, 130.64, 128.78, 128.22, 128.15, 125.55, 120.06, 116.10, 113.76, 65.82, 53.74, 51.99, 40.54, 38.36, 30.75, 30.54, 17.66; HRMS (m/z): [M+Na]$^+$ calcd., 476.1962; found, 476.1978.

Benzyl ((5S,8S,E)-5-(3,5-difluorobenzyl)-2,7-diox-1,6-diazacyclododec-en-8-yl)carbamate

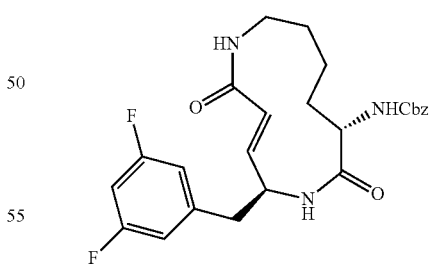

Yield: 30%; NMR $^1$H (400 MHz, DMSO-d$_6$): δ 8.43-8.42 (d, 1H), 7.43-7.41 (t, 1H), 7.36-7.33 (m, 4H), 7.32-7.29 (m, 1H), 7.13-7.10 (m, 1H), 7.09-7.05 (m, 3H), 6.78-6.75 (dd, 1H), 6.33-6.31 (d, 1H), 4.99 (s, 2H), 4.61 (m, 1H), 4.32-4.31 (m, 1H), 3.32-3.28 (m, 1H), 3.12-3.06 (m, 2H), 2.99-2.95 (m, 2H), 2.72-2.69 (dd, 1H), 2.18-2.14 (t, 1H), 1.61-1.57 (m, 1H), 1.46-1.42 (m, 2H), 1.29-1.23 (m, 1H), 0.92-0.88 (q, 1H); $^{13}$C (100 MHz, DMSO-d$_6$): δ 171.76, 166.13, 163.55, 161.92, 155.95, 145.39, 135.46, 130.33, 128.79, 128.23, 128.16, 120.22, 112.71, 112.54, 102.45, 65.82, 59.61, 53.75, 40.53, 38.36, 30.73, 30.51, 17.67; HRMS (m/z): [M+Na]+ calcd., 494.1867; found, 494.1889.

Benzyl ((5S,8S,E)-5-(2-chlorobenzyl)-2,7-dioxo-1,6-diazacyclododec-3-en-8-yl)carbamate

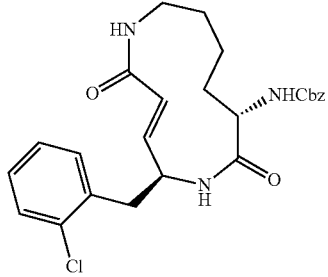 [SMILES: O=C1/C=C/[C@H](Cc2ccccc2Cl)NC(=O)[C@@H](NC(=O)OCc2ccccc2)CCCCN1]

Yield: 22%; NMR $^1$H (400 MHz, DMSO-$d_6$): δ 8.51-8.50 (d, 1H), 7.47-7.43 (m, 2H), 7.42-7.40 (d, 1H), 7.37-7.33 (m, 4H), 7.32-7.29 (m, 2H), 7.19-7.18 (d, 1H), 6.71-6.68 (dd, 1H), 6.38-6.35 (d, 1H), 4.99 (s, 2H), 4.70 (m, 1H), 4.32-4.30 (m, 1H), 3.32-3.29 (m, 1H), 3.05-3.02 (dd, 1H), 2.99-2.97 (m, 1H), 2.89-2.85 (dd, 1H), 2.23-2.18 (t, 1H), 1.60-1.55 (t, 1H), 1.46-1.43 (m, 2H), 1.29-1.25 (m, 1H), 1.19-1.15 (m, 1H), 0.92-0.88 (q, 1H); $^{13}$C (100 MHz, DMSO-$d_6$): δ 171.79, 166.07, 155.98, 144.98, 137.45, 135.97, 133.57, 131.73, 129.83, 128.80, 128.24, 128.17, 127.75, 120.44, 65.81, 53.79, 50.05, 46.19, 40.50, 36.48, 30.75, 30.46, 17.70; HRMS (m/z): [M+H]+ calcd., 470.1847; found, 470.1858.

Benzyl ((5S,8S,E)-5-(3-chlorobenzyl)-2,7-dioxo-1,6-diazacyclododec-3-en-8-yl)carbamate

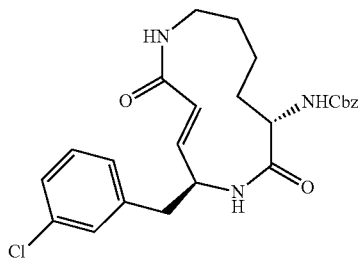 [SMILES: O=C1/C=C/[C@H](Cc2cccc(Cl)c2)NC(=O)[C@@H](NC(=O)OCc2ccccc2)CCCCN1]

Yield: 28%; NMR $^1$H (400 MHz, DMSO-$d_6$): δ 8.43-8.42 (d, 1H), 7.41 (s, 1H), 7.37-7.33 (m, 5H), 7.32-7.28 (d, 3H), 7.09-7.08 (d, 1H), 6.79-6.76 (dd, 1H), 6.34-6.31 (d, 1H), 4.99 (s, 2H), 4.62-4.58 (m, 1H), 4.34-4.30 (m, 1H), 3.31-3.29 (m, 1H), 3.12-3.08 (m, 1H), 2.99-2.93 (m, 2H), 2.71-2.67 (dd, 1H), 2.20-2.16 (t, 1H), 1.61-1.57 (t, 1H), 1.47-1.43 (m, 2H), 1.29-1.25 (m, 1H), 1.19-1.15 (m, 1H), 0.94-0.88 (q, 1H); $^{13}$C (100 MHz, DMSO-$d_6$): δ 171.71, 166.09, 155.92, 145.64, 141.51, 137.45, 133.34, 130.61, 129.32, 128.78, 128.21, 128.15, 126.89, 120.08, 65.82, 53.72, 51.97, 46.24, 40.55, 38.23, 30.74, 30.54, 17.65; HRMS (m/z): [M+Na]+ calcd., 492.1666; found, 492.1651.

Benzyl ((5S,8S,E)-5-(4-chlorobenzyl)-2,7-dioxo-1,6-diazacyclododec-3-en-8-yl)carbamate

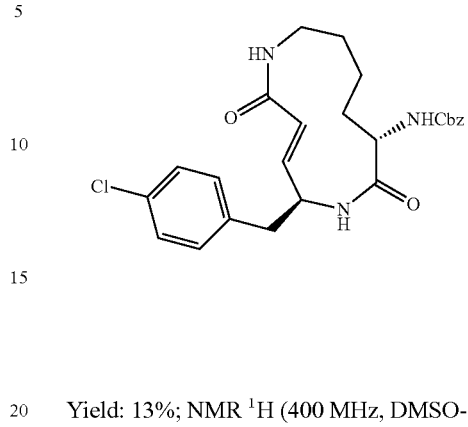

Yield: 13%; NMR $^1$H (400 MHz, DMSO-$d_6$): δ 8.44-8.42 (d, 1H), 7.44-7.42 (t, 1H), 7.39-7.36 (m, 3H), 7.35-7.30 (m, 5H), 7.14-7.13 (d, 1H), 6.77-6.74 (dd, 1H), 6.33-6.30 (d, 1H), 4.99 (s, 2H), 4.60-4.56 (m, 1H), 4.32-4.29 (m, 1H), 3.31-3.27 (m, 1H), 2.99-2.95 (m, 1H), 2.93-2.90 (dd, 1H), 2.71-2.67 (dd, 1H), 2.20-2.16 (t, 1H), 1.59-1.55 (t, 1H), 1.46-1.42 (m, 2H), 1.28-1.24 (m, 1H), 0.93-0.86 (q, 1H); $^{13}$C (100 MHz, DMSO-$d_6$): δ 171.72, 166.14, 155.94, 145.74, 137.95, 137.45, 131.52, 131.28, 128.80, 128.72, 128.24, 128.17, 119.99, 65.81, 53.72, 52.10, 49.06, 40.50, 38.30, 30.75, 26.42, 17.64; HRMS (m/z): [M+H]+ calcd., 470.1847; found, 470.1850.

Benzyl ((5S,8S,E)-5-(3-methylbenzyl)-2,7-dioxo-1,6-diazacyclododec-3-en-8-yl)carbamate

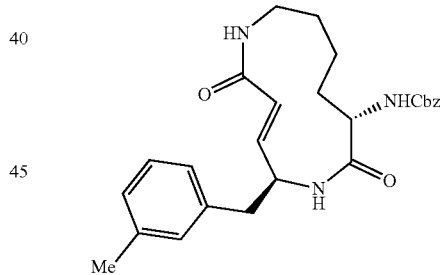

Yield: 31%; NMR $^1$H (400 MHz, DMSO-$d_6$): δ 8.43-8.42 (d, 1H), 7.42-7.40 (t, 1H), 7.37-7.29 (m, 5H), 7.21-7.19 (t, 1H), 7.13-7.11 (m, 2H), 7.10-7.08 (d, 1H), 7.05-7.04 (d, 1H), 6.77-6.73 (dd, 1H), 6.33-6.30 (d, 1H), 4.99 (s, 2H), 4.61-4.57 (m, 1H), 4.32-4.30 (m, 1H), 3.32-3.27 (m, 1H), 2.99-2.96 (m, 1H), 2.87-2.84 (dd, 1H), 2.70-2.66 (dd, 1H), 2.30 (s, 3H), 2.21-2.17 (t, 1H), 1.59-1.55 (t, 1H), 1.45-1.42 (m, 2H), 1.28-1.24 (t, 1H), 0.93-0.87 (q, 1H); $^{13}$C (100 MHz, DMSO-$d_6$): δ 171.65, 166.18, 155.94, 146.04, 138.73, 137.80, 137.45, 130.04, 128.80, 128.68, 128.23, 128.16, 127.54, 126.42, 119.76, 65.79, 53.72, 52.21, 40.50, 38.83, 38.31, 30.74, 30.54, 21.51, 17.64; HRMS (m/z): [M+H]+ calcd., 450.2393; found, 450.2398.

49
Benzyl ((5S,8S,E)-5-(4-methylbenzyl)-2,7-dioxo-1,6-diazacyclododec-3-en-8-yl)carbamate

50
tert-Butyl 3-(((2S,1S,E)-11-(((benzyloxy)carbonyl)amino)-5,12-dioxo-1,6-diazacyclododec-3-en-2-yl)methyl)-1H-indole-1-carboxylate

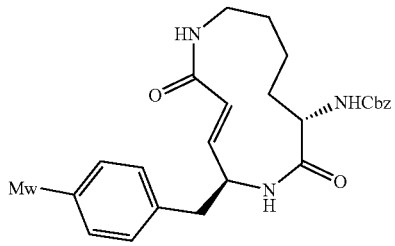

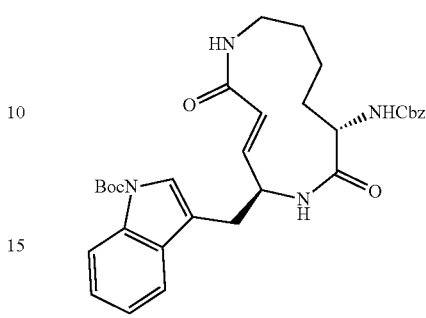

Yield: 20%; NMR $^1$H (400 MHz, DMSO-d$_6$): δ 8.42-8.40 (d, 1H), 7.42-7.40 (t, 1H), 7.37-7.29 (m, 5H), 7.19-7.10 (d, 2H), 7.13-7.11 (m, 3H), 6.75-6.72 (dd, 1H), 6.32-6.30 (d, 1H), 4.99 (s, 2H), 4.57-4.55 (m, 1H), 4.32-4.30 (m, 1H), 3.32-3.27 (m, 1H), 2.98-2.96 (m, 1H), 2.86-2.83 (dd, 1H), 2.70-2.66 (dd, 1H), 2.28 (s, 3H), 2.21-2.17 (t, 1H), 1.58-1.54 (t, 1H), 1.45-1.42 (m, 2H), 1.28-1.24 (t, 1H), 0.93-0.87 (q, 1H); $^{13}$C (100 MHz, DMSO-d$_6$): δ 171.62, 166.18, 155.94, 146.03, 137.46, 135.83, 135.72, 129.37, 129.25, 128.80, 128.23, 128.15, 119.75, 65.79, 53.71, 52.31, 40.50, 38.48, 38.29, 30.76, 30.55, 21.14, 17.63; HRMS (m/z): [M+H]+ calcd., 450.2393; found, 450.2392.

Yield: 29%; NMR $^1$H (400 MHz, MeOD-d$_4$): δ 8.14-8.12 (d, 1H), 7.65-7.63 (d, 1H), 7.55 (s, 1H), 7.36-7.26 (m, 6H), 7.24-7.7.16 (m, 1H), 7.06-7.03 (dd, 1H), 6.51-6.49 (d, 1H), 5.07 (s, 2H), 4.99-4.94 (m, 1H), 4.49-4.47 (m, 1H), 3.57-3.52 (t, 1H), 3.16-3.10 (m, 2H), 3.00-2.96 (dd, 1H), 2.22-2.17 (t, 1H), 1.87-1.83 (m, 1H), 1.70-1.63 (m, 10H), 1.52-1.46 (m, 1H), 1.45-1.40 (m, 1H), 1.18-1.14 (m, 1H); $^{13}$C (100 MHz, MeOD-d$_4$): δ 172.34, 168.13, 156.52, 149.59, 146.50, 136.72, 128.04, 127.60, 127.47, 124.15, 123.51, 122.33, 119.06, 118.59, 116.45, 114.78, 83.44, 66.24, 53.73, 50.33, 48.16, 38.37, 30.03, 29.89, 28.20, 26.99, 17.35; HRMS (m/z): [M+H]+ calcd., 575.2870; found, 575.2863.

Example 6: General Synthesis of Syringolin Proteasome Inhibitor Analogs

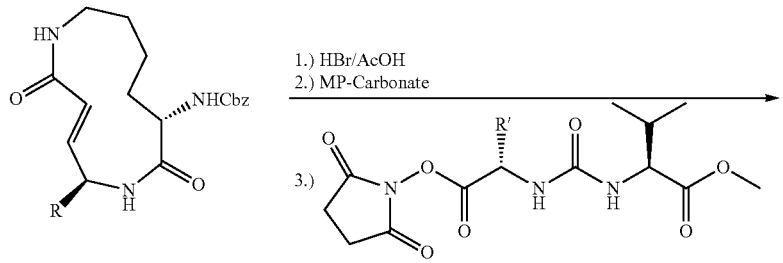

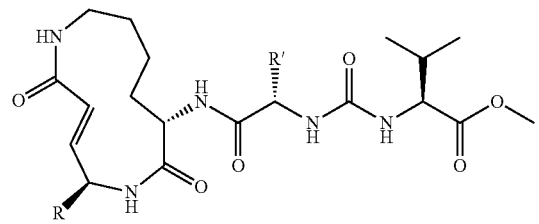

27-70% Yield

Each macrocycle (0.05 mmol) was first deprotected by dissolving in 250 μL of acetic acid, followed by addition of a 33% HBr solution in acetic acid (753 μL, 4.3 mmol). After stirring for 45 minutes at room temperature, the solution was concentrated, dissolved in 500 μL of DMF, and placed into an ice bath. MP-Carbonate resin (133 mg, 0.4 mmol) was then added and the solution was stirred at room temperature for 20 minutes. Then, the dipeptide urea NHS-ester (0.1 mmol) was added to the reaction and was stirred at room temperature for 18 hours. The resin was then filtered, washing with THF, and concentrated before purification via flash chromatography using a 5%-10% MeOH in DCM gradient. TLC conditions—DCM:MeOH, 10:1 v/v, (See FIG. 3).

Syringolin B Methyl Ester (1):

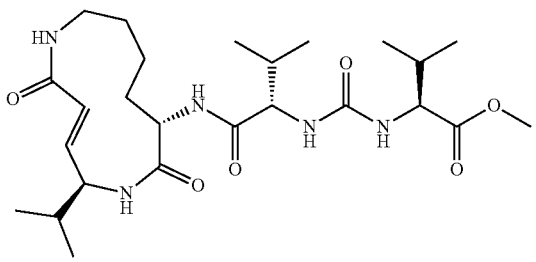 [SMILES: COC(=O)[C@@H](NC(=O)N[C@H](C(=O)N[C@H]1CCCCNC(=O)/C=C/[C@H](C(C)C)NC1=O)C(C)C)C(C)C]

Yield: 51%; NMR $^1$H (600 MHz, MeOD-d$_4$): δ 7.93-7.92 (d, 1H), 7.07-7.04 (dd, 1H), 6.59-6.58 (d, 1H), 6.49-6.48 (d, 1H), 6.40-6.37 (d, 1H), 4.71-4.69 (m, 1H), 4.25-4.22 (m, 2H), 4.13-4.11 (dd, 1H), 3.73 (s, 3H), 3.53-3.48 (t, 1H), 3.15-3.12 (m, 1H), 2.14-2.08 (m, 3H), 1.91-1.83 (m, 2H), 1.67-1.63 (m, 1H), 1.46-1.38 (m, 2H), 1.16-1.14 (m, 1H), 1.08-1.07 (d, 3H), 1.05-1.04 (d, 3H), 0.99-0.97 (t, 6H), 0.94-0.93 (m, 6H); $^{13}$C (150 MHz, MeOD-d$_4$): δ 173.28, 172.69, 171.67, 168.27, 159.09, 146.61, 119.06, 58.85, 58.23, 56.86, 52.10, 50.97, 48.44, 38.43, 31.94, 30.73, 29.89, 29.80, 19.14, 18.42, 18.37, 18.18, 17.46, 16.62, 16.49; HRMS (m/z): [M+H]$^+$ calcd., 510.3292; found, 510.3287.

(S)-methyl 2-(3-((S)-1-(((5S,8S,E)-5-isobutyl-2,7-dioxo-1,6-diazacyclododec-3-en-8-yl)amino)-3-methyl-1-oxobutan-2-yl) ureido)-3-methylbutanoate (2)

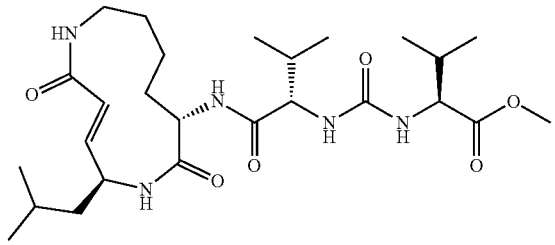 [SMILES: COC(=O)[C@@H](NC(=O)N[C@H](C(=O)N[C@H]1CCCCNC(=O)/C=C/[C@H](CC(C)C)NC1=O)C(C)C)C(C)C]

Yield: 42%; NMR 1H (600 MHz, MeOD-d$_4$): δ 8.54-8.53 (d, 1H), 8.00-7.95 (d, 1H), 7.04-7.01 (dd, 1H), 6.41-6.38 (d, 1H), 4.68-4.65 (m, 1H), 4.59-4.56 (m, 1H), 4.24-4.22 (d, 1H), 4.13-4.12 (d, 1H), 3.53-3.49 (t, 1H), 3.14-3.12 (d, 1H), 2.15-2.09 (m, 3H), 1.92-1.87 (m, 1H), 1.81-1.76 (m, 1H), 1.68-1.64 (m, 1H), 1.53-1.38 (m, 4H), 1.20-1.14 (q, 1H), 1.01-0.98 (dd, 6H), 0.98-0.95 (dd, 6H), 0.94-0.93 (d, 6H); $^{13}$C (150 MHz, MeOD-d$_4$): δ 173.26, 172.80, 171.72, 168.31, 159.04, 147.46, 118.36, 58.92, 58.14, 52.29, 50.97, 48.94, 41.71, 38.39, 30.73, 29.89, 29.77, 25.08, 21.88, 20.66, 18.43, 18.18, 17.46, 16.62, 16.50; HRMS (m/z): [M+H]$^+$ calcd., 524.3448; found, 524.3439.

(S)-methyl 2-(3-((S)-1-(((5S,8S,E)-5-benzyl-2,7-dioxo-1,6-diazacyclododec-3-en-8-yl)amino)-3-methyl-1-oxobutan-2-yl)ureido)-3-methylbutanoate (3)

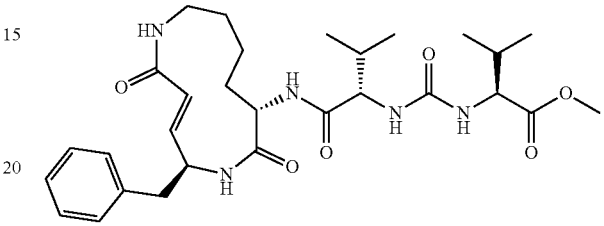

Yield: 60%; NMR $^1$H (600 MHz, MeOD-d$_4$): δ 7.91-7.90 (d, 1H), 7.33-7.29 (m, 4H), 7.25-7.23 (t, 1H), 7.00-6.97 (dd, 1H), 6.59-6.57 (d, 1H), 6.49-6.46 (d, 2H), 4.81 (m, 1H), 4.64 (m, 1H), 4.22-4.19 (dd, 1H), 4.10-4.08 (m, 1H), 3.72 (s, 3H), 3.57-3.52 (t, 1H), 3.16-3.13 (d, 1H), 3.00-2.98 (m, 1H), 2.87-2.85 (m, 1H), 2.19-2.07 (m, 3H), 1.93-1.88 (m, 1H), 1.66 (m, 1H), 1.49-1.39 (m, 2H), 1.19-1.13 (m, 1H), 1.00-0.99 (m, 1H), 0.96-0.95 (d, 6H), 0.93-0.90 (t, 6H); $^{13}$C (150 MHz, MeOD-d$_4$): δ 173.26, 172.68, 171.52, 168.08, 159.06, 146.61, 137.55, 128.56, 128.21, 126.38, 118.88, 58.94, 58.23, 52.22, 50.95, 48.17, 38.61, 38.37, 30.72, 30.62, 29.89, 29.72, 18.40, 18.15, 17.39, 16.62, 16.48; HRMS (m/z): [M+H]$^+$ calcd., 556.3130; found, 556.3127.

(S)-methyl 2-(3-((S)-1-(((5S,8S,E)-2,7-dioxo-5-(3-(trifluoromethyl)benzyl)-1,6-diaza cyclododec-3-en-8-yl)amino)-3-methyl-1-oxobutan-2-yl)ureido)-3-methylbutanoate (4)

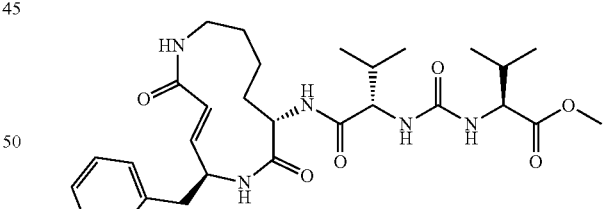

Yield: 49%; NMR $^1$H (600 MHz, MeOD-d$_4$): δ 7.91-7.90 (d, 1H), 7.64 (s, 1H), 7.60-7.59 (d, 1H), 7.57-7.51 (m, 3H), 7.03-7.00 (dd, 1H), 6.59-6.57 (d, 1H), 6.50-6.46 (d, 1H), 4.86-4.85 (m, 1H), 4.62 (m, 1H), 4.20-4.19 (dd, 1H), 4.09-4.07 (m, 1H), 3.72 (s, 3H), 3.57-3.52 (t, 1H), 3.16-3.12 (d, 2H), 2.91-2.85 (m, 1H), 2.18-2.07 (m, 3H), 1.94-1.92 (m, 1H), 1.68-1.66 (m, 1H), 1.48-1.39 (m, 2H), 1.19-1.13 (m, 1H), 0.95-0.94 (d, 6H), 0.92-0.89 (t, 6H); $^{13}$C (150 MHz, MeOD-d$_4$): δ 173.25, 172.70, 171.66, 167.98, 159.01, 146.11, 139.11, 132.36, 128.99, 125.36, 123.19, 119.25, 58.94, 58.13, 52.01, 50.94, 48.16, 38.37, 38.01, 30.71, 30.61, 29.88, 29.68, 18.37, 18.13, 17.39, 16.59, 16.47; HRMS (m/z): [M+Na]+ calcd., 648.2985; found, 648.2968.

(S)-methyl 2-(3-((S)-1-(((5S,8S,E)-5-(2-fluorobenzyl)-2,7-dioxo-1,6-diazacyclododec-3-en-8-yl)amino)-3-methyl-1-oxobutan-2-yl) ureido)-3-methylbutanoate (5)

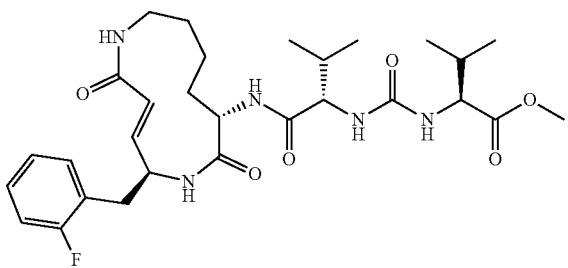 [SMILES: COC(=O)[C@@H](NC(=O)N[C@H](C(=O)N[C@H]1CCCCNC(=O)/C=C/[C@H](Cc2ccccc2F)NC1=O)C(C)C)C(C)C]

Yield: 52%; NMR $^1$H (600 MHz, MeOD-d$_4$): δ 7.92-7.91 (d, 1H), 7.36-7.34 (t, 1H), 7.31-7.28 (q, 1H), 7.16-7.14 (t, 1H), 7.11-7.08 (t, 1H), 6.97-6.93 (dd, 1H), 6.60-6.59 (d, 1H), 6.51-6.48 (d, 2H), 4.87-4.84 (m, 1H), 4.62 (m, 1H), 4.21-4.19 (dd, 1H), 4.09-4.06 (m, 1H), 3.72 (s, 3H), 3.57-3.53 (t, 1H), 3.16-3.13 (d, 1H), 3.06-3.04 (dd, 1H), 2.94-2.90 (m, 1H), 2.21-2.16 (m, 1H), 2.14-2.09 (m, 2H), 1.93-1.89 (m, 1H), 1.69-1.64 (m, 1H), 1.49-1.40 (m, 2H), 1.18-1.12 (m, 1H), 0.97-0.95 (dd, 6H), 0.93-0.91 (d, 6H); $^{13}$C (150 MHz, MeOD-d$_4$): δ 173.25, 172.73, 171.55, 167.98, 160.36, 159.07, 145.98, 130.92, 128.56, 124.08, 119.22, 114.99, 114.84, 59.02, 58.19, 52.16, 50.96, 48.44, 48.16, 38.34, 31.76, 30.73, 29.89, 29.61, 18.40, 18.14, 17.37, 16.57, 16.46; HRMS (m/z): [M+H]+ calcd., 576.3197; found, 576.3190.

(S)-methyl 2-(3-((S)-1-(((5S,8S,E)-5-(3-fluorobenzyl)-2,7-dioxo-1,6-diazacyclododec-3-en-8-yl)amino)-3-methyl-1-oxobutan-2-yl)ureido)-3-methylbutanoate (6)

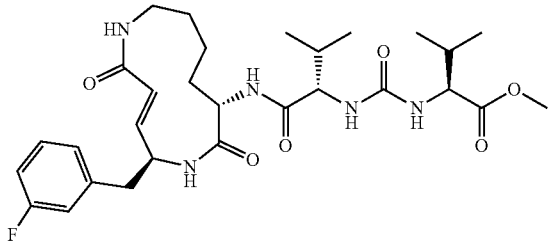 [SMILES: COC(=O)[C@@H](NC(=O)N[C@H](C(=O)N[C@H]1CCCCNC(=O)/C=C/[C@H](Cc2cccc(F)c2)NC1=O)C(C)C)C(C)C]

Yield: 56%; NMR $^1$H (600 MHz, MeOD-d$_4$): δ 7.97-7.96 (d, 1H), 7.35-7.31 (q, 1H), 7.13-7.12 (d, 1H), 7.08-7.06 (d, 1H), 7.02-6.99 (d, 1H), 6.98-6.96 (d, 1H), 6.60-6.58 (d, 1H), 6.49-6.46 (m, 2H), 4.84-4.81 (m, 1H), 4.65 (m, 1H), 4.22-4.19 (dd, 1H), 4.13-4.10 (t, 1H), 3.72 (s, 3H), 3.56-3.52 (t, 1H), 3.16-3.13 (d, 1H), 3.05-3.02 (dd, 1H), 2.88-2.80 (m, 1H), 2.19-2.13 (m, 1H), 2.12-2.06 (m, 2H), 1.92-1.87 (m, 1H), 1.69-1.64 (m, 1H), 1.48-1.39 (m, 2H), 1.19 (q, 1H), 0.96-0.94 (dd, 6H), 0.92-0.89 (dd, 6H); $^{13}$C (150 MHz, MeOD-d$_4$): δ 173.29, 172.72, 171.62, 168.00, 163.73, 159.09, 146.31, 140.46, 129.91, 129.85, 124.47, 119.07, 115.41, 113.03, 58.93, 58.24, 52.01, 50.96, 38.37, 38.10, 30.74, 29.88, 29.73, 18.42, 18.16, 17.41, 16.62, 16.48; HRMS (m/z): [M+Na]+ calcd., 598.3017; found, 598.3038.

(S)-methyl 2-(3-((S)-1-(((5S,8S,E)-5-(3,5-difluorobenzyl)-2,7-dioxo-1,6-diazacyclododec-3-en-8-yl)amino)-3-methyl-1-oxobutan-2-yl)ureido)-3-methylbutanoate (7)

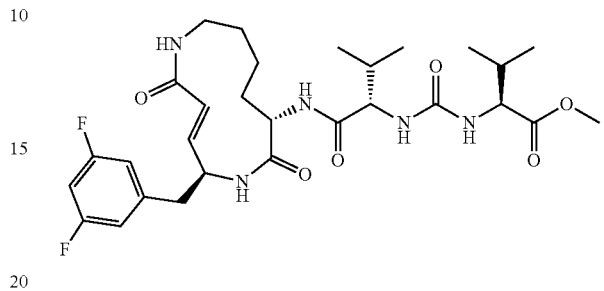

Yield: 40%; NMR $^1$H (600 MHz, MeOD-d$_4$): δ 7.90-7.89 (d, 1H), 7.01-7.00 (d, 1H), 6.99-6.98 (d, 1H), 6.96-6.92 (d, 2H), 6.84-6.81 (t, 1H), 6.57-6.56 (d, 1H), 6.49-6.45 (m, 2H), 4.82-4.80 (m, 1H), 4.64-4.60 (m, 1H), 4.22-4.19 (dd, 1H), 4.09-4.07 (t, 1H), 3.72 (s, 3H), 3.55-3.51 (t, 1H), 3.16-3.14 (d, 1H), 3.08-3.04 (dd, 1H), 2.85-2.80 (m, 1H), 2.18-2.08 (m, 3H), 1.94-1.89 (m, 1H), 1.68-1.64 (m, 1H), 1.49-1.39 (m, 2H), 1.18-1.13 (q, 1H), 0.96-0.95 (dd, 6H), 0.93-0.91 (dd, 6H); 13C (150 MHz, MeOD-d$_4$): δ 173.27, 172.72, 171.66, 168.00, 163.99, 162.26, 159.01, 145.85, 119.40, 111.59, 111.42, 101.55, 59.00, 58.18, 52.14, 50.94, 48.16, 38.41, 37.89, 30.73, 29.87, 18.37, 18.12, 17.44, 16.61, 16.50; HRMS (m/z): [M+Na]+ calcd., 616.2923; found, 616.2941.

(S)-methyl 2-(3-((S)-1-(((5S,8S,E)-5-(2-chlorobenzyl)-2,7-dioxo-1,6-diazacyclododec-3-en-8-yl)amino)-3-methyl-1-oxobutan-2-yl)ureido)-3-methylbutanoate (8)

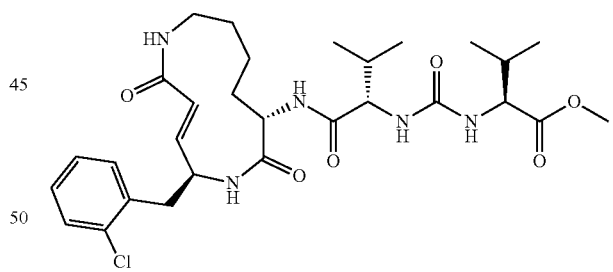

Yield: 53%; NMR $^1$H (600 MHz, MeOD-d$_4$): δ 7.43-7.42 (dd, 1H), 7.38-7.36 (dd, 1H), 7.30-7.26 (m, 2H), 7.16-7.13 (d, 1H), 6.96-6.93 (dd, 1H), 6.52-6.49 (d, 1H), 4.65-4.63 (t, 1H), 4.21-4.20 (d, 1H), 4.08-4.07 (d, 1H), 3.72 (s, 3H), 3.58-3.52 (m, 1H), 3.17-3.14 (dd, 2H), 3.01-2.97 (dd, 1H), 2.21-2.14 (m, 1H), 2.13-2.08 (m, 2H), 1.94-1.88 (m, 1H), 1.68-1.64 (m, 1H), 1.50-1.40 (m, 2H), 1.18-1.12 (q, 1H), 0.97-0.94 (dd, 6H), 0.92-0.91 (d, 6H); $^{13}$C (150 MHz, MeOD-d$_4$): δ 173.24, 172.73, 171.55, 167.95, 159.03, 145.89, 135.00, 133.69, 130.96, 129.32, 128.97, 128.78, 128.27, 126.87, 119.25, 58.95, 58.11, 52.16, 50.97, 50.25, 38.35, 36.22, 30.72, 29.88, 18.42, 18.16, 17.39, 16.58, 16.48; HRMS (m/z): [M+H]+ calcd., 592.2902; found, 592.2899.

(S)-methyl 2-(3-((S)-1-(((5S,8S,E)-5-(2-chlorobenzyl)-2,7-dioxo-1,6-diazacyclododec-3-en-8-yl)amino)-3-methyl-1-oxobutan-2-yl) ureido)-3-methylbutanoate (9)

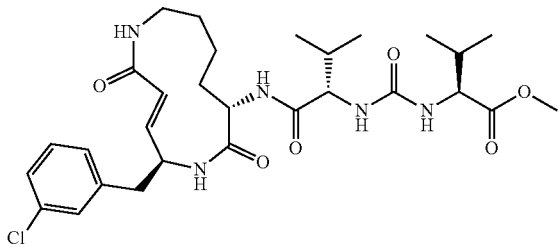 [SMILES: COC(=O)[C@@H](NC(=O)N[C@H](C(=O)N[C@H]1CCCCNC(=O)/C=C/[C@H](Cc2cccc(Cl)c2)NC1=O)C(C)C)C(C)C]

Yield: 66%; NMR ¹H (600 MHz, MeOD-d₄): δ 7.35 (s, 1H), 7.32-7.30 (m, 1H), 7.27-7.25 (m, 2H), 7.02-6.98 (dd, 1H), 6.58-6.57 (d, 1H), 6.49-6.46 (d, 1H), 4.83-4.80 (quin, 1H), 4.64-4.62 (m, 1H), 4.21-4.19 (m, 1H), 4.09-4.07 (m, 1H), 3.72 (s, 3H), 3.56-3.52 (t, 1H), 3.16-3.14 (d, 2H), 3.05-3.02 (dd, 1H), 2.83-2.79 (dd, 1H), 2.18-2.07 (m, 3H), 1.94-1.88 (m, 1H), 1.70-1.64 (m, 1H), 1.48-1.39 (m, 2H), 1.18-1.12 (q, 1H), 0.97-0.95 (dd, 6H), 0.92-0.90 (t, 6H); ¹³C (150 MHz, MeOD-d₄): δ 173.25, 172.69, 171.61, 168.00, 159.01, 146.20, 140.03, 133.94, 129.69, 128.69, 126.99, 126.52, 119.15, 58.96, 58.14, 52.11, 52.02, 50.95, 48.16, 38.37, 37.99, 30.73, 29.88, 29.68, 18.40, 18.15, 17.40, 16.61, 16.49; HRMS (m/z): [M+Na]⁺ calcd., 614.2721; found, 614.2736.

(S)-methyl 2-(3-((S)-1-(((5S,8S,E)-5-(4-chlorobenzyl)-2,7-dioxo-1,6-diazacyclododec-3-en-8-yl)amino)-3-methyl-oxobutan-2-yl)ureido)-3-methylbutanoate(10)

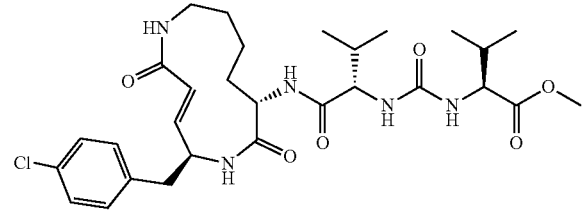 [SMILES: COC(=O)[C@@H](NC(=O)N[C@H](C(=O)N[C@H]1CCCCNC(=O)/C=C/[C@H](Cc2ccc(Cl)cc2)NC1=O)C(C)C)C(C)C]

Yield: 58%; NMR ¹H (600 MHz, MeOD-d₄): δ 8.00 (s, 1H), 7.94-7.93 (d, 1H), 7.33-7.29 (m, 4H), 6.99-6.96 (dd, 1H), 6.60-6.59 (d, 1H), 6.48-6.46 (d, 2H), 4.80-4.77 (quin, 1H), 4.63-4.61 (m, 1H), 4.21-4.19 (dd, 1H), 4.09-4.07 (t, 1H), 3.72 (s, 3H), 3.56-3.51 (t, 1H), 3.16-3.13 (d, 2H), 3.01-2.98 (dd, 1H), 2.85-2.81 (dd, 1H), 2.72-2.68 (m, 1H), 2.18-2.07 (m, 3H), 1.92-1.88 (m, 1H), 1.70-1.64 (m, 1H), 1.48-1.39 (m, 2H), 1.34-1.30 (m, 2H), 1.18-1.12 (m, 1H), 0.96-0.95 (d, 6H), 0.92-0.90 (t, 6H); ¹³C (150 MHz, MeOD-d₄): δ 173.27, 171.61, 168.01, 163.45, 159.11, 146.30, 136.44, 132.20, 130.21, 128.24, 119.10, 58.21, 52.08, 50.96, 48.16, 38.37, 37.75, 30.73, 29.87, 29.66, 18.40, 18.16, 17.42, 16.59, 16.47; HRMS (m/z): [M+H]⁺ calcd., 592.2902; found, 592.2889.

(S)-methyl 3-methyl-2-(3-((S)-3-methyl-1-(((5S,8S,E)-5-(3-methylbenzyl)-2,7-dioxo-1,6-diazacyclododec-3-en-8-yl)amino)-1-oxobutan-2-yl)ureido)butanoate (11)

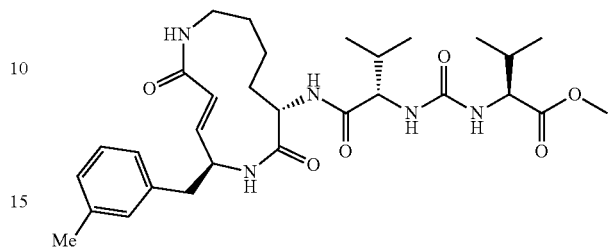

Yield: 58%; NMR ¹H (600 MHz, MeOD-d₄): δ 7.94-7.92 (d, 1H), 7.20-7.18 (t, 1H), 7.12 (s, 1H), 7.09-7.07 (d, 1H), 7.06-7.05 (d, 1H), 7.00-6.97 (dd, 1H), 6.60-6.58 (d, 1H), 6.49-6.45 (m, 2H), 4.81-4.78 (m, 1H), 4.66-4.62 (m, 1H), 4.22-4.19 (m, 1H), 4.11-4.09 (m, 1H), 3.72 (s, 3H), 3.57-3.52 (t, 1H), 3.16-3.13 (d, 1H), 2.97-2.93 (dd, 1H), 2.85-2.80 (dd, 1H), 2.33 (s, 3H), 2.19-2.05 (m, 3H), 1.94-1.87 (m, 1H), 1.68-1.64 (m, 1H), 1.48-1.39 (m, 3H), 1.34-1.31 (m, 1H), 1.18-1.12 (q, 1H), 0.97-0.95 (d, 6H), 0.92-0.90 (t, 6H); ¹³C (150 MHz, MeOD-d₄): δ 173.27, 172.77, 171.55, 168.08, 159.10, 146.74, 137.89, 137.42, 129.25, 128.10, 127.06, 125.60, 118.76, 59.01, 58.23, 52.29, 52.19, 50.96, 48.17, 38.59, 38.35, 30.74, 29.89, 29.73, 20.06, 18.42, 18.16, 17.37, 16.62, 16.47; HRMS (m/z): [M+H]⁺ calcd., 572.3443; found, 572.3440.

(S)-methyl 3-methyl-2-(3-((S)-3-methyl-1-(((5S,8S,E)-5-(4-methylbenzyl)-2,7-dioxo-1,6-diazacyclododec-3-en-8-yl)amino)-1-oxobutan-2-yl)ureido)butanoate (12)

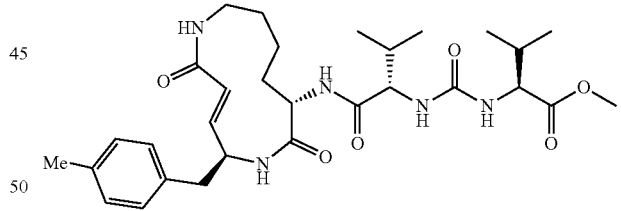

Yield: 49%; NMR ¹H (600 MHz, MeOD-d₄): δ 7.92-7.91 (d, 1H), 7.18-7.17 (d, 2H), 7.13-7.12 (d, 2H), 6.99-6.96 (dd, 1H), 6.59-6.58 (d, 1H), 6.49-6.45 (m, 2H), 4.79-4.75 (m, 1H), 4.65-4.63 (m, 1H), 4.21-4.19 (m, 1H), 4.10-4.08 (m, 1H), 3.72 (s, 3H), 3.56-3.52 (t, 1H), 3.15-3.13 (d, 1H), 2.96-2.92 (dd, 1H), 2.85-2.80 (dd, 1H), 2.32 (s, 3H), 2.19-2.08 (m, 3H), 1.92-1.88 (m, 1H), 1.68-1.64 (m, 1H), 1.49-1.39 (m, 3H), 1.34-1.31 (m, 1H), 1.18-1.12 (q, 1H), 0.96-0.95 (d, 6H), 0.92-0.90 (t, 6H); ¹³C (150 MHz, MeOD-d₄): δ 173.27, 172.77, 171.50, 168.08, 159.07, 146.74, 136.02, 134.40, 128.80, 128.45, 118.76, 59.04, 58.23, 52.33, 52.21, 50.95, 48.16, 38.35, 38.23, 30.73, 29.89, 29.71, 19.68, 18.40, 18.16, 17.37, 16.61, 16.47; HRMS (m/z): [M+H]+ calcd., 572.3443; found, 572.3444.

57

(S)-methyl 2-(3-((S)-1-(((5S,8S,E)-5-((1H-indol-3-yl)methyl)-2,7-dioxo-1,6-diazacyclododec-3-en-8-yl)amino)-3-methyl-1-oxobutan-2-yl)ureido)-3-methylbutanoate (13)

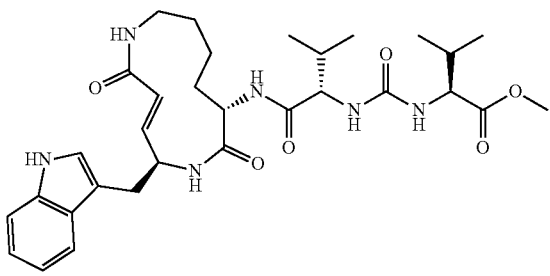 [SMILES: COC(=O)[C@@H](NC(=O)N[C@H](C(=O)N[C@H]1CCCCNC(=O)/C=C/[C@H](Cc2c[nH]c3ccccc23)NC1=O)C(C)C)C(C)C]

Yield: 27%; NMR $^1$H (600 MHz, MeOD-d$_4$): δ 7.93-7.92 (d, 1H), 7.59-7.57 (d, 1H), 7.36-7.35 (d, 1H), 7.14 (s, 1H), 7.12-7.10 (t, 1H), 7.06-7.02 (m, 2H), 6.59-6.58 (d, 1H), 6.50-6.48 (m, 2H), 4.67-4.65 (m, 1H), 4.21-4.19 (dd, 1H), 4.11-4.08 (t, 1H), 3.72 (s, 3H), 3.57-3.52 (t, 1H), 3.15-3.11 (m, 2H), 3.07-3.04 (m, 1H), 2.19-2.14 (m, 1H), 2.12-2.06 (m, 2H), 1.93-1.89 (m, 1H), 1.68-1.64 (m, 1H), 1.48-1.38 (m, 2H), 1.21-1.15 (q, 1H), 0.97-0.96 (d, 3H), 0.94-0.93 (d, 3H), 0.92-0.91 (d, 3H), 0.91-0.89 (d, 3H); $^{13}$C (150 MHz, MeOD-d$_4$): δ 173.28, 172.74, 171.50, 168.25, 159.10, 147.33, 136.74, 127.11, 122.72, 121.05, 118.41, 117.77, 110.91, 110.13, 59.00, 58.15, 52.19, 51.32, 50.95, 48.17, 38.39, 30.73, 29.89, 28.83, 18.41, 18.13, 17.43, 16.60, 16.50; HRMS (m/z): [M+H]$^+$ calcd., 597.3395; found, 597.3393.

(S)-methyl 2-(3-((S)-1-(((5S,8S,E)-5-isopropyl-2,7-dioxo-1,6-diazacyclododec-3-en-8-yl)amino)-1-oxo-3-phenylpropan-2-yl)ureido)-3-methylbutanoate (14)

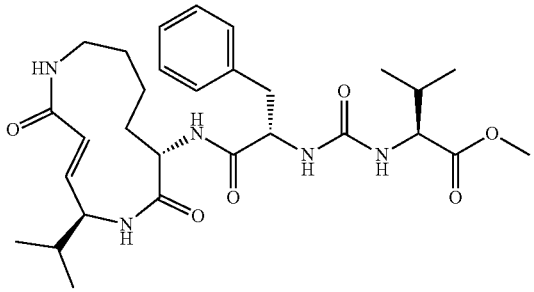 [SMILES: COC(=O)[C@@H](NC(=O)N[C@@H](Cc1ccccc1)C(=O)N[C@H]1CCCCNC(=O)/C=C/[C@H](C(C)C)NC1=O)C(C)C]

Yield: 62%; NMR $^1$H (600 MHz, MeOD-d$_4$): δ 7.90-7.88 (d, 1H), 7.29-7.27 (t, 2H), 7.24-7.20 (m, 3H), 7.07-7.04 (dd, 1H), 6.71-6.70 (d, 1H), 6.44-6.43 (d, 1H), 6.37-6.35 (d, 1H), 4.68-4.66 (m, 1H), 4.58-4.54 (q, 1H), 4.25-4.23 (m, 1H), 4.19-4.17 (dd, 1H), 3.71 (s, 3H), 3.51-3.47 (t, 1H), 3.14-3.10 (d, 1H), 3.07-3.04 (dd, 1H), 3.01-2.98 (dd, 1H), 2.69 (bs, 1H), 2.12-2.03 (m, 2H), 1.88-1.81 (m, 2H), 1.62-1.58 (m, 1H), 1.39-1.34 (t, 1H), 1.24-1.20 (m, 1H), 1.08-1.06 (d, 3H), 1.05-1.04 (d, 3H), 0.95-0.93 (d, 3H), 0.91-0.90 (d, 3H); $^{13}$C (150 MHz, MeOD-d$_4$): δ 173.20, 172.30, 171.53, 168.24, 158.50, 146.57, 136.73, 129.14, 128.07, 126.38, 119.03, 58.18, 56.84, 52.02, 50.99, 38.42, 37.87, 31.92, 30.75, 29.95, 19.15, 18.37, 18.14, 17.18, 16.67; HRMS (m/z): [M+H]$^+$ calcd., 558.3292; found, 558.3283.

58

(S)-methyl 2-(3-((S)-1-(((5S,8S,E)-5-benzyl-2,7-dioxo-1,6-diazacyclododec-3-en-8-yl)amino)-1-oxo-3-phenylpropan-2-yl)ureido)-3-methylbutanoate (15)

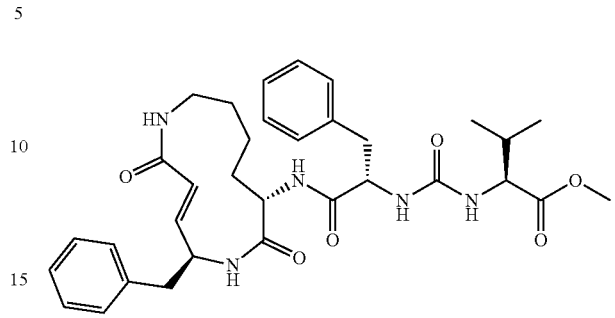

Yield: 53%; NMR $^1$H (600 MHz, MeOD-d$_4$): δ 7.35-7.15 (m, 10H), 7.01-6.98 (dd, 1H), 6.70-6.68 (d, 1H), 6.46-6.43 (d, 1H), 4.80-4.78 (m, 1H), 4.59 (bs, 1H), 4.49-4.47 (m, 1H), 4.18-4.15 (m, 1H), 3.70 (s, 3H), 3.55-3.51 (t, 1H), 3.15-3.12 (d, 1H), 3.03-2.96 (m, 3H), 2.84-2.80 (dd, 1H), 2.14-2.05 (m, 2H), 1.89-1.85 (m, 1H), 1.61 (m, 1H), 1.42-1.31 (m, 2H), 1.25-1.21 (m, 1H), 1.06-0.99 (q, 1H), 0.93-0.92 (d, 3H), 0.89-0.88 (d, 3H); $^{13}$C (150 MHz, MeOD-d$_4$): δ 173.17, 172.20, 171.31, 168.01, 158.45, 146.64, 137.66, 136.64, 129.05, 128.56, 128.21, 128.07, 126.39, 118.75, 58.09, 54.94, 52.30, 52.00, 50.97, 38.48, 38.31, 37.77, 30.70, 29.94, 29.72, 18.13, 17.02, 16.63; HRMS (m/z): [M+H]$^+$ calcd., 606.3292; found, 606.3283.

(S)-methyl 2-(3-(2-(((5S,8S,E)-5-((1H-indol-3-yl)methyl)-2,7-dioxo-1,6-diazacyclododec-3-en-8-yl)amino)-2-oxoethyl)ureido)-3-methylbutanoate (16)

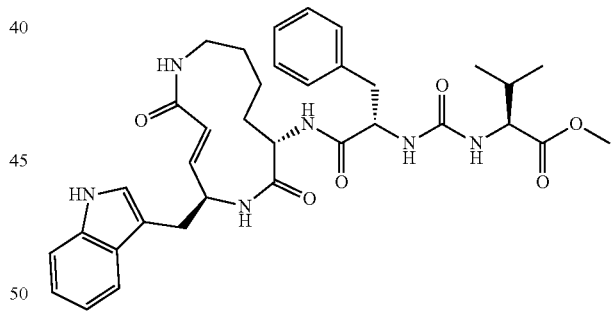

Yield: 70%; NMR $^1$H (600 MHz, MeOD-d$_4$): δ 7.60-7.59 (d, 1H), 7.37-7.36 (d, 1H), 7.21-7.18 (m, 3H), 7.15 (s, 1H), 7.12-7.10 (m, 2H), 7.07-7.02 (m, 2H), 6.68-6.67 (d, 1H), 6.47-6.44 (d, 1H), 4.60-4.58 (m, 1H), 4.48-4.45 (m, 1H), 4.17-4.14 (m, 1H), 3.70 (s, 3H), 3.56-3.51 (t, 1H), 3.16-3.12 (m, 2H), 3.03-2.99 (m, 3H), 2.13-2.04 (m, 2H), 1.90-1.86 (m, 1H), 1.62-1.59 (m, 1H), 1.41-1.36 (m, 2H), 1.24-1.21 (m, 1H), 1.08-1.02 (m, 1H), 0.91-0.90 (d, 3H), 0.88-0.87 (d, 3H); $^{13}$C (150 MHz, MeOD-d$_4$): δ 173.16, 172.24, 171.64, 168.93, 158.45, 147.26, 136.77, 136.61, 129.01, 128.07, 127.08, 126.41, 122.72, 121.06, 118.41, 117.79, 110.93, 110.23, 60.13, 58.09, 55.03, 52.08, 51.36, 50.95, 48.16, 38.35, 37.73, 30.70, 29.92, 28.74, 24.86, 18.08, 17.05, 16.60; HRMS (m/z): [M+H]$^+$ calcd., 645.3401; found, 645.3392.

(S)-methyl 2-(3-((S)-3-(2-chlorophenyl)-1-((5S,8S,E)-5-(2-fluorobenzyl)-2,7-dioxo-1,6-diazacyclodo-dec-3-en-8-ylamino)-1-oxopropan-2-yl)ureido)-3-methylbutanoate (17)

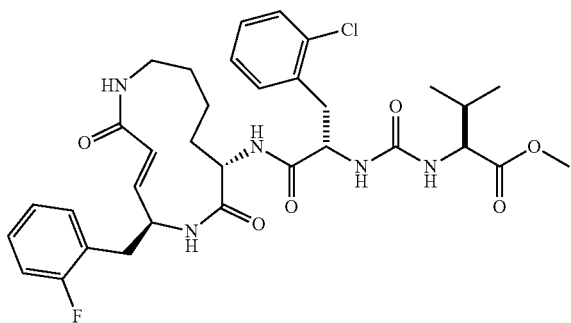

Figure 12A:
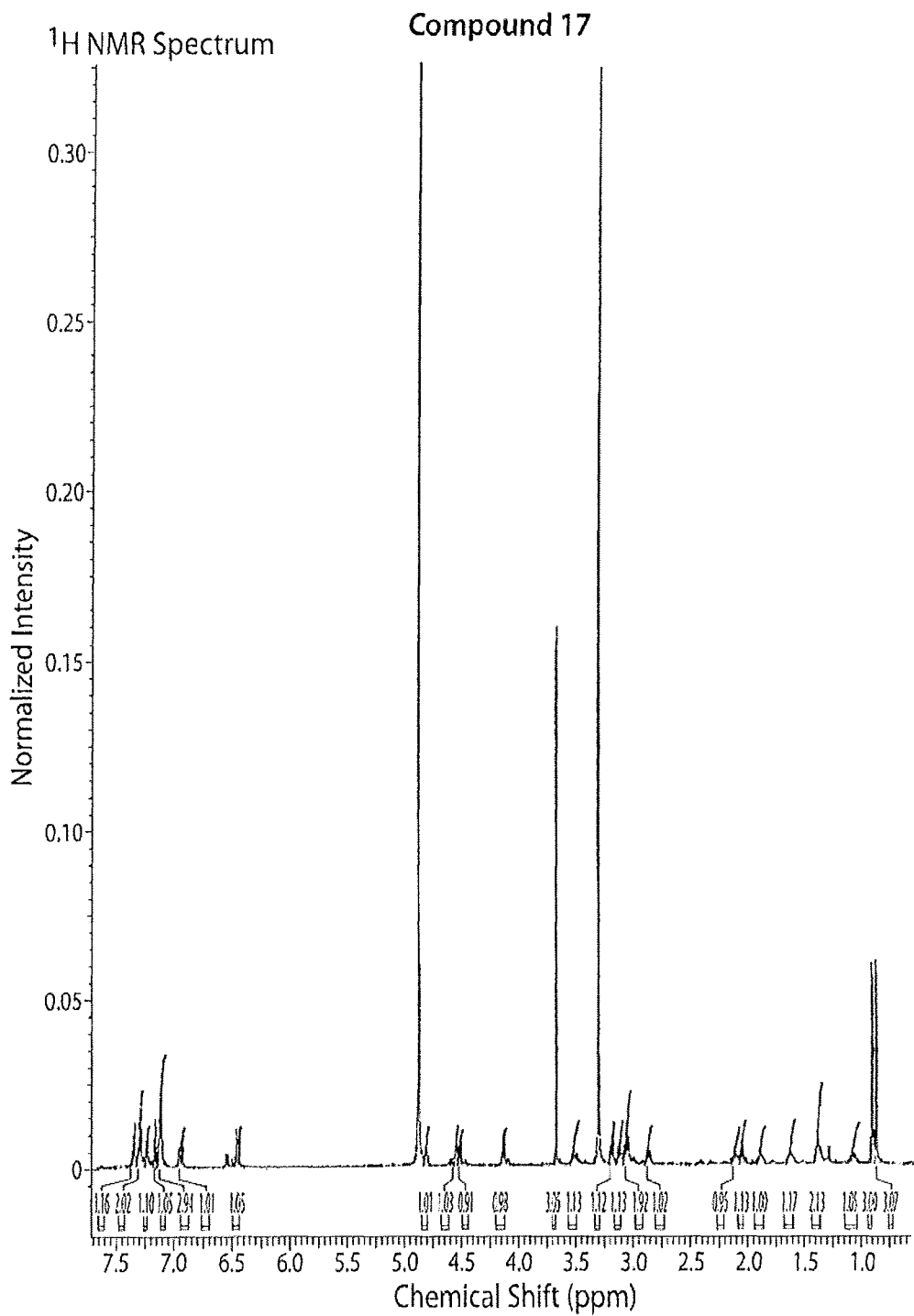
FIGS. 12A-12B show the $^{1}$H NMR and $^{13}$C NMR, respectively, for compound 17.
Figure 12B:
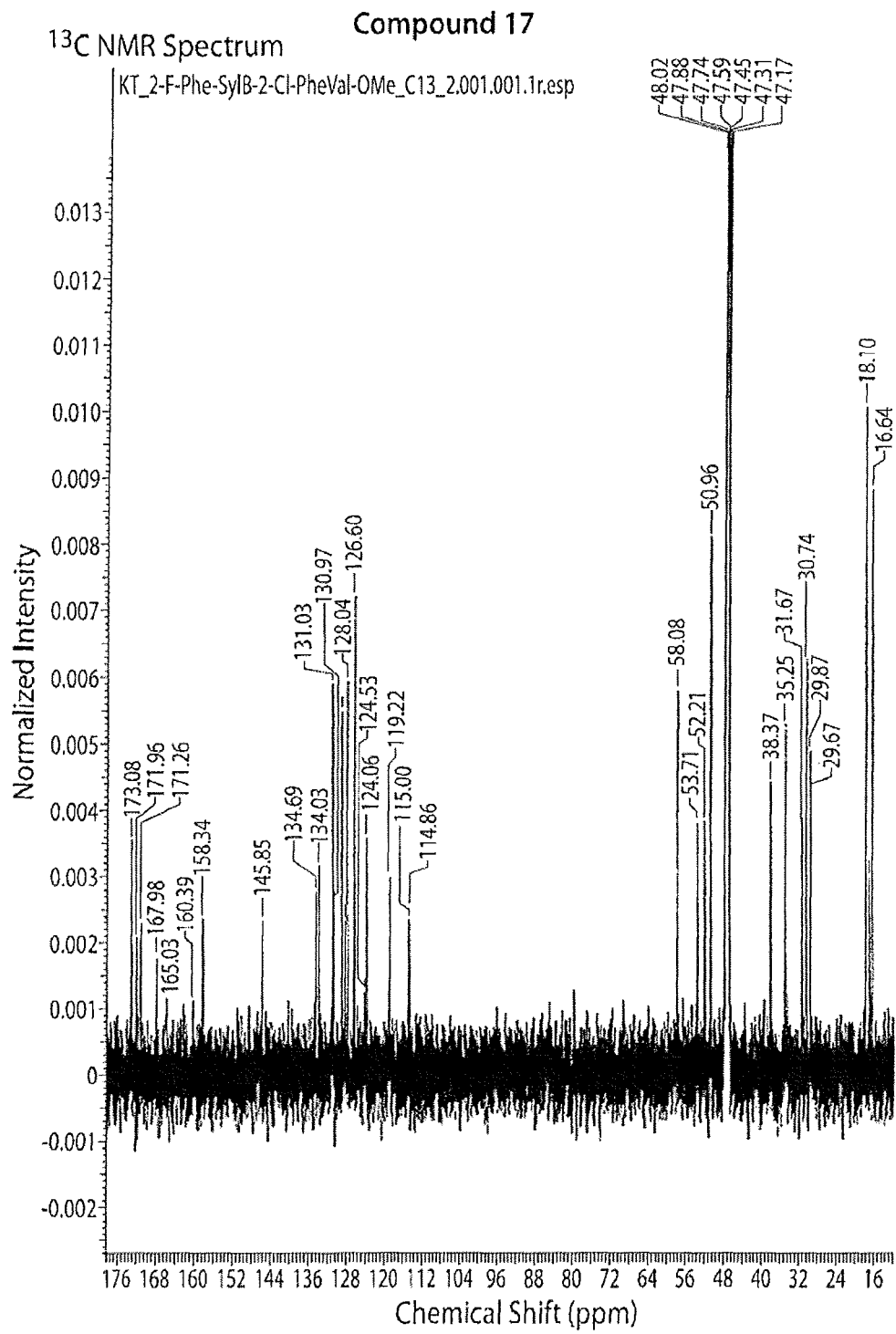

NMR $^1$H (600 MHz, MeOD-d$_4$) spectrum shown in FIG. 12A; NMR $^{13}$C (150 MHz, MeOD-d$_4$) spectrum shown in FIG. 13B.

(S)-methyl 2-(3-((S)-3-(3-chlorophenyl)-1-((5S,8S,E)-5-(2-fluorobenzyl)-2,7-dioxo-1,6-diazacyclodo-dec-3-en-8-ylamino)-1-oxopropan-2-yl) ureido)-3-methylbutanoate (18)

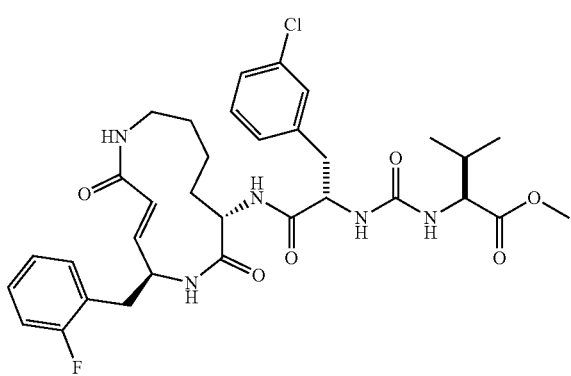

Figure 13A:
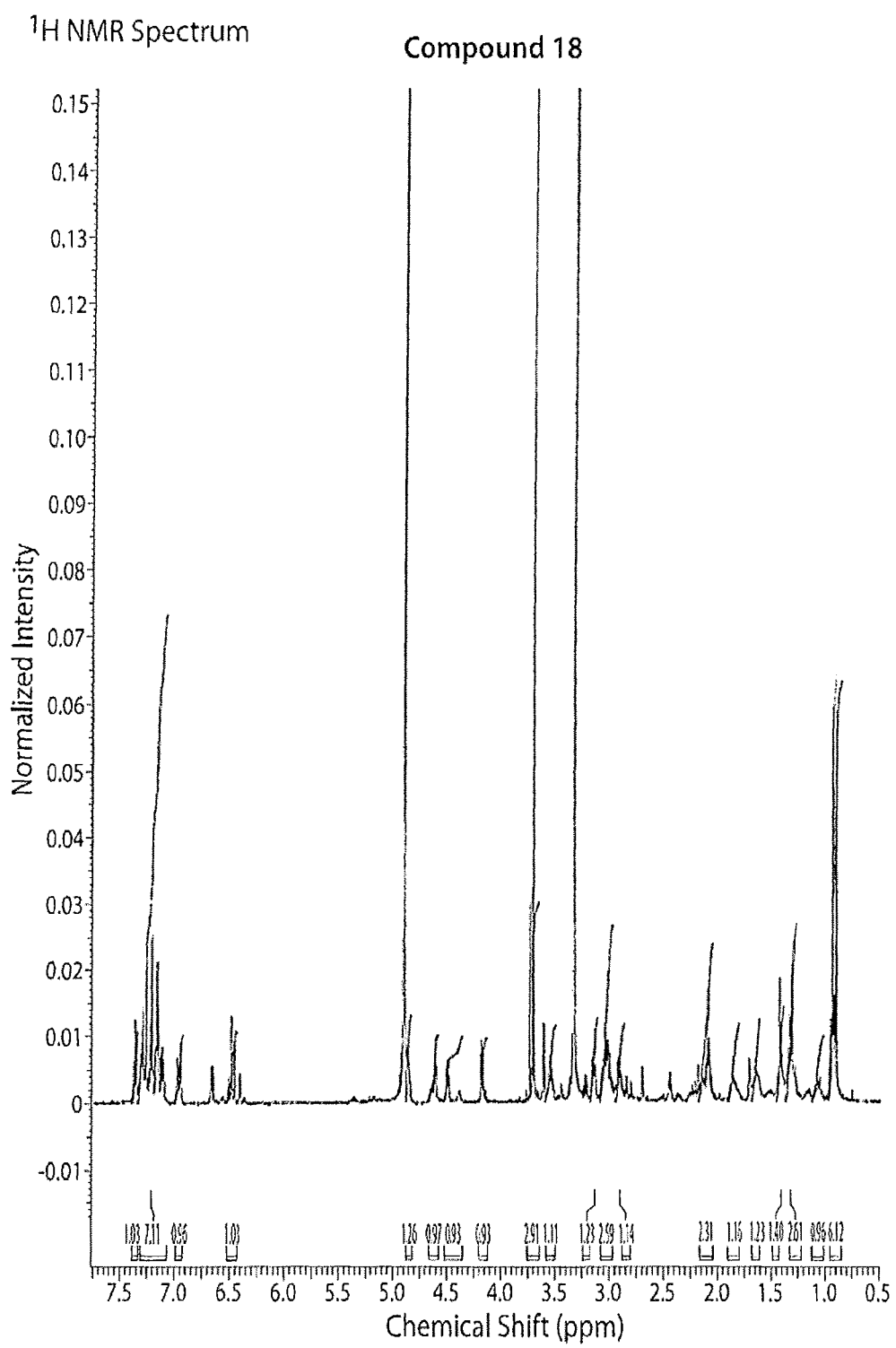
FIGS. 13A-13B show the $^{1}$H NMR and $^{13}$C NMR, respectively, for compound 18.
Figure 13B:
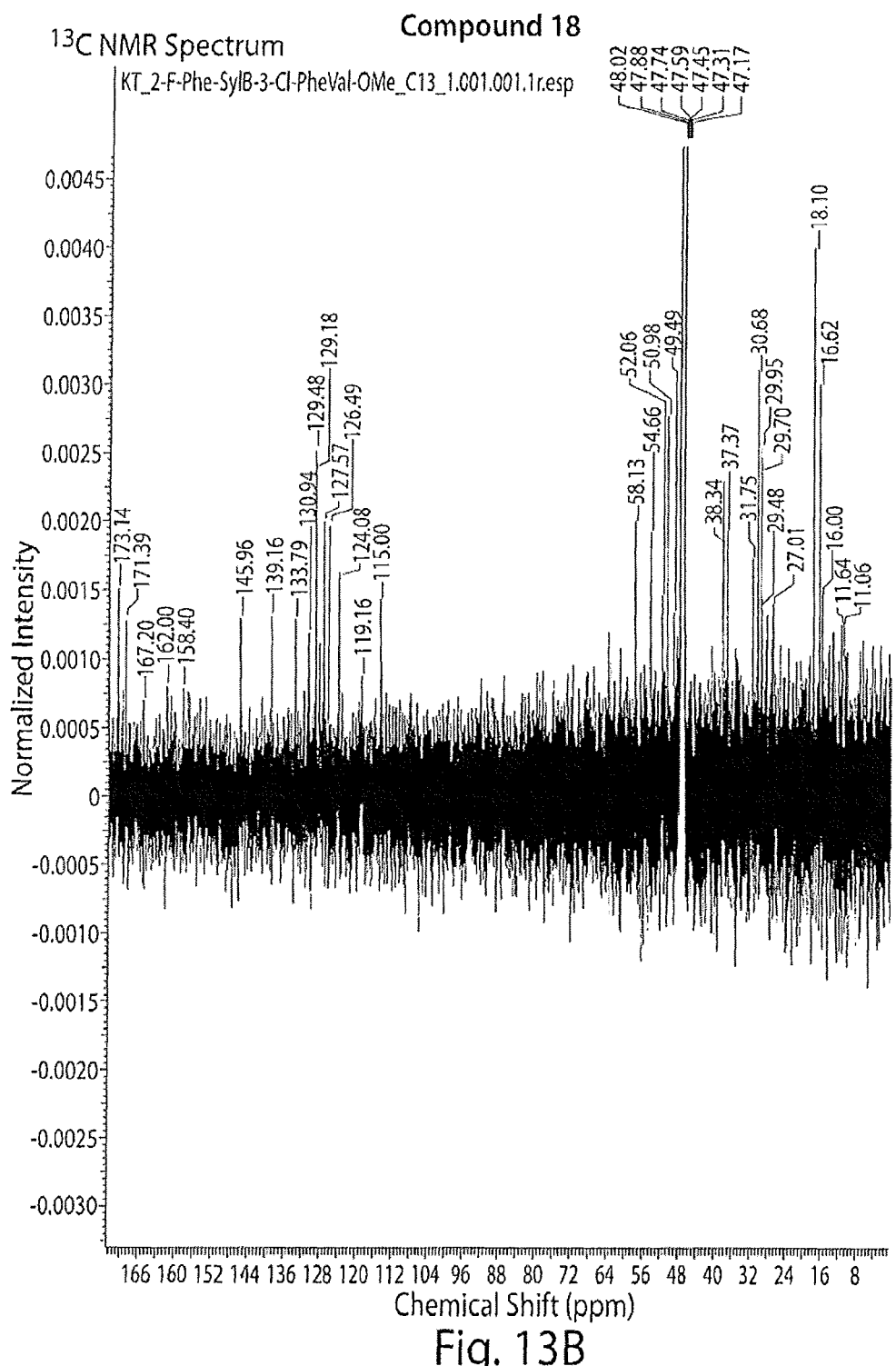

NMR $^1$H (600 MHz, MeOD-d$_4$) spectrum shown in FIG. 13A; NMR $^{13}$C (150 MHz, MeOD-d$_4$) spectrum shown in FIG. 13B.

(S)-methyl 2-(3-((S)-1-((5S,8S,E)-5-(2-fluorobenzyl)-2,7-dioxo-1,6-diazacyclododec-3-en-8-ylamino)-1-oxo-3-phenylpropan-2-yl)ureido)-3-methylbutanoate (19)

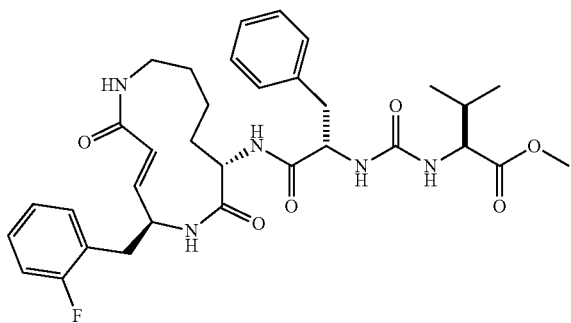 [SMILES: COC(=O)[C@@H](NC(=O)N[C@@H](Cc1ccccc1)C(=O)N[C@H]1CCCCNC(=O)/C=C/[C@H](Cc2ccccc2F)NC1=O)C(C)C]

Figure 14A:
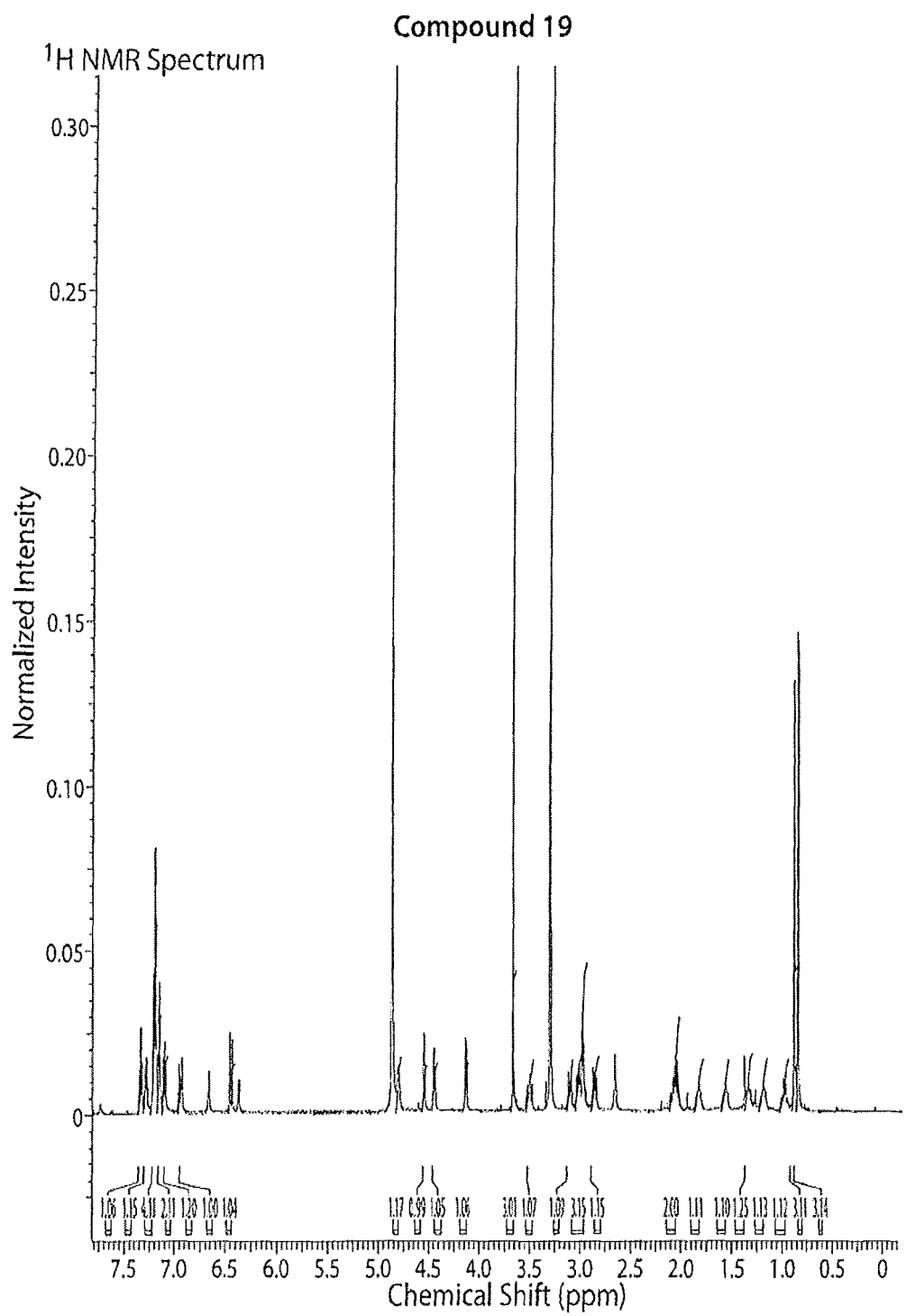
FIGS. 14A-14B show the $^{1}$H NMR and $^{13}$C NMR, respectively, for compound 19.
Figure 14B:
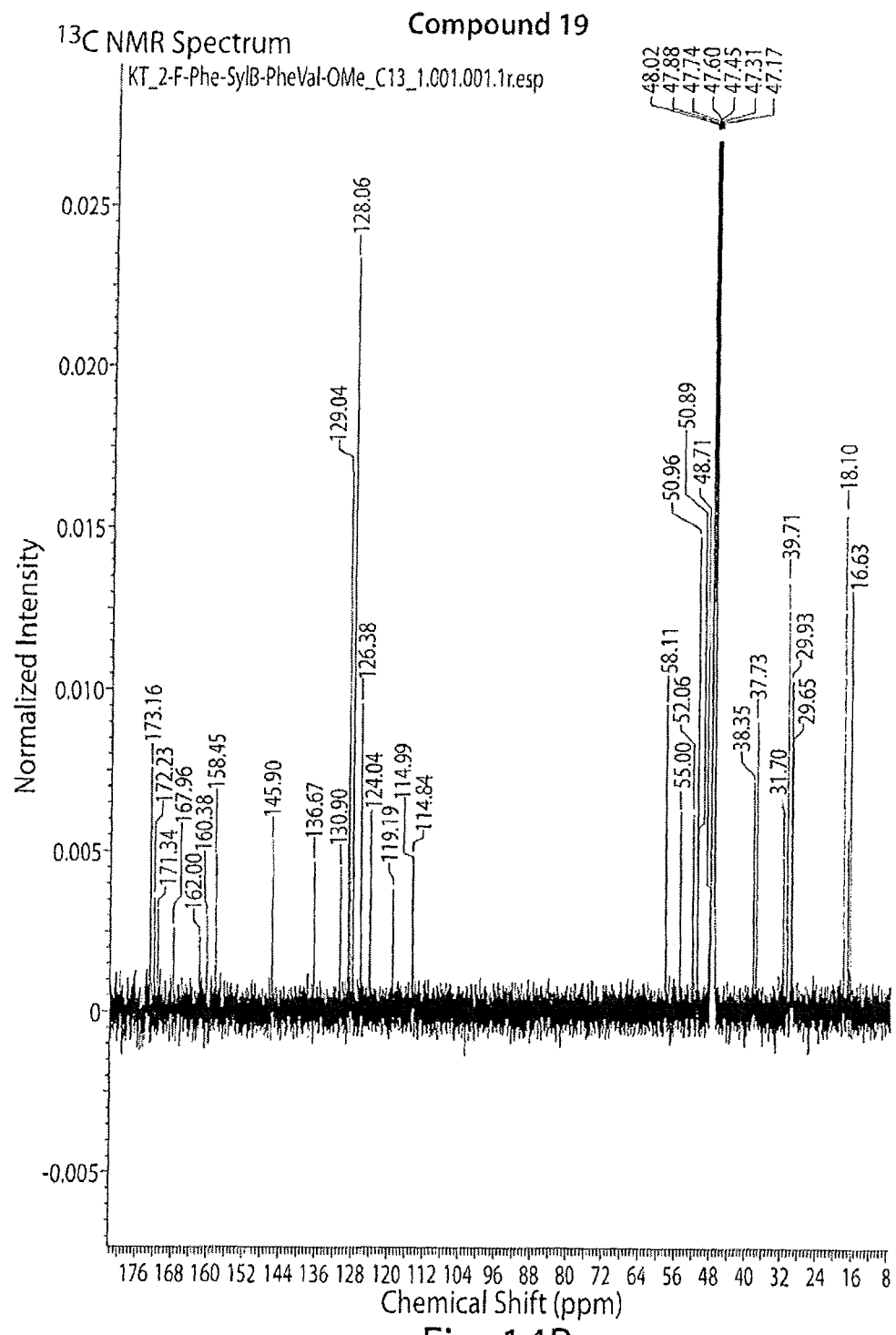

NMR $^1$H (600 MHz, MeOD-d$_4$) spectrum shown in FIG. 14A; NMR $^{13}$C (150 MHz, MeOD-d$_4$) spectrum shown in FIG. 14B.

(S)-methyl 2-(3-((S)-1-((5S,8S,E)-5-(2-fluorobenzyl)-2,7-dioxo-1,6-diazacyclododec-3-en-8-ylamino)-1-oxo-3-m-tolylpropan-2-yl) ureido)-3-methylbutanoate (20)

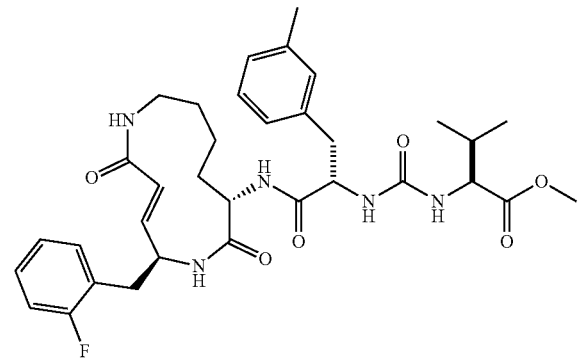 [SMILES: COC(=O)[C@@H](NC(=O)N[C@@H](Cc1cccc(C)c1)C(=O)N[C@H]1CCCCNC(=O)/C=C/[C@H](Cc2ccccc2F)NC1=O)C(C)C]

Figure 15A:
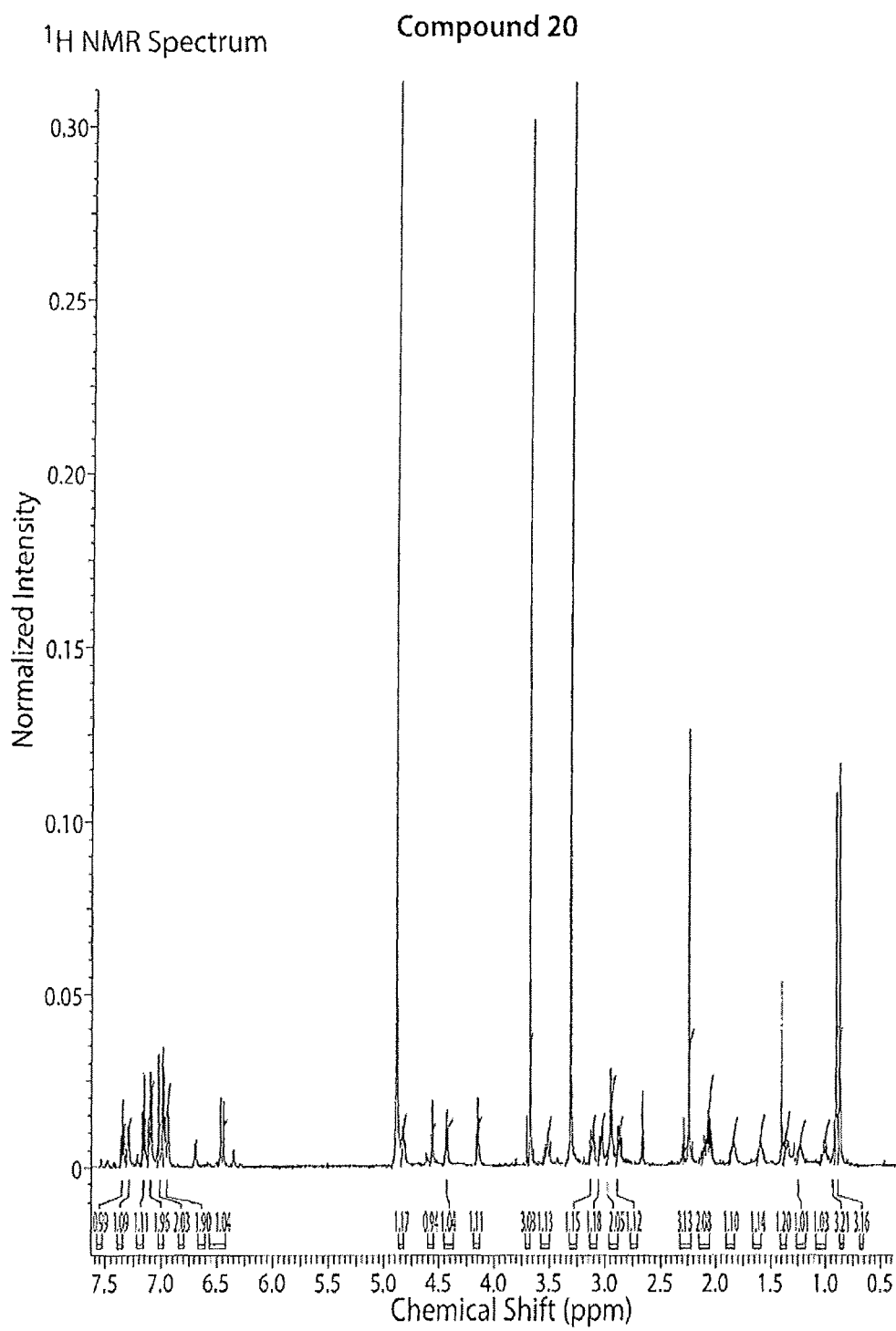
FIGS. 15A-15B show the $^{1}$H NMR and $^{13}$C NMR, respectively, for compound 20.
Figure 15B:
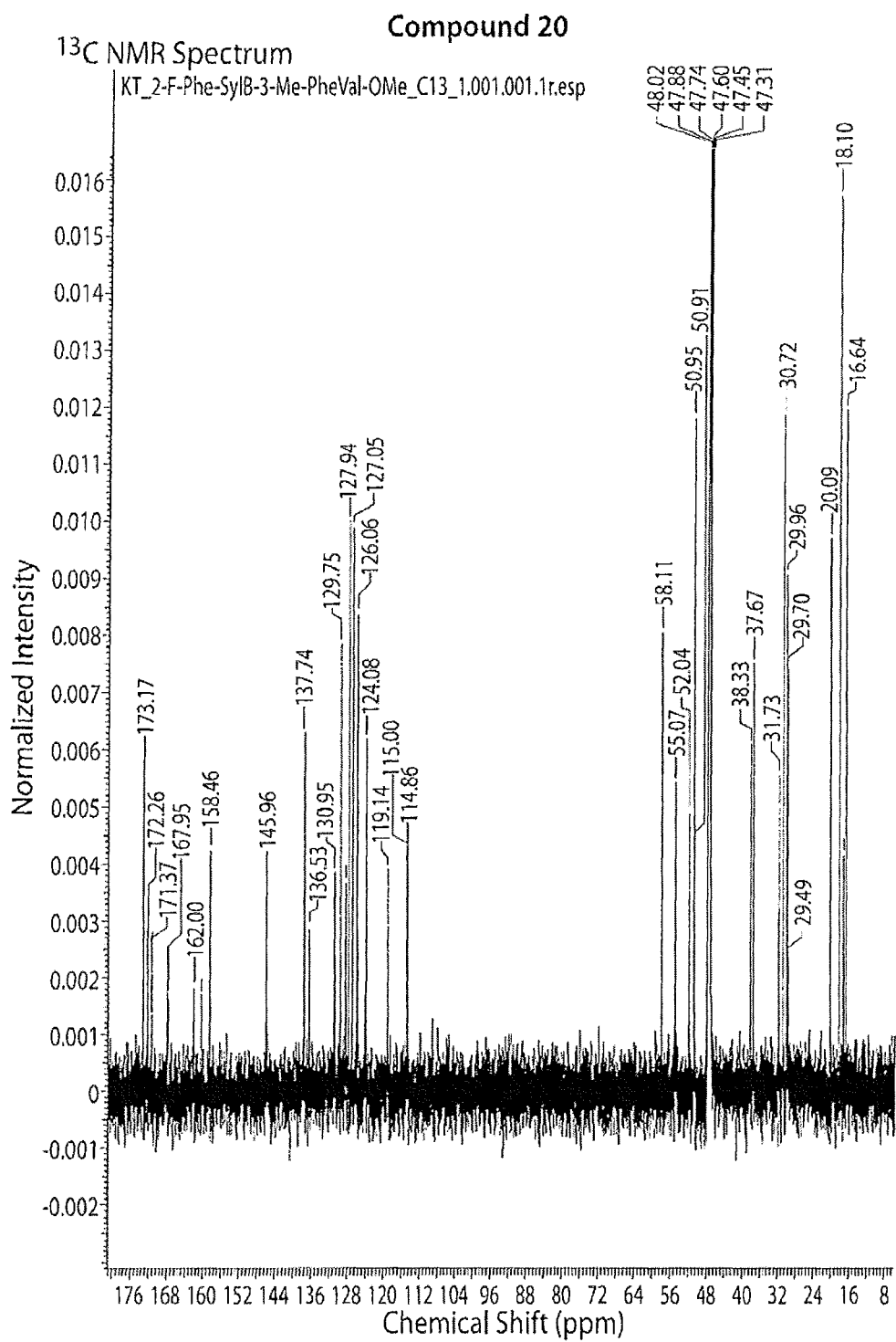

NMR $^1$H (600 MHz, MeOD-d$_4$) spectrum shown in FIG. 15A; NMR $^{13}$C (150 MHz, MeOD-d$_4$) spectrum shown in FIG. 15B.

(S)-methyl 2-(3-((S)-1-((5S,8S,E)-5-(2-fluorobenzyl)-2,7-dioxo-1,6-diazacyclododec-3-en-8-ylamino)-1-oxo-3-p-tolylpropan-2-yl) ureido)-3-methylbutanoate (21)

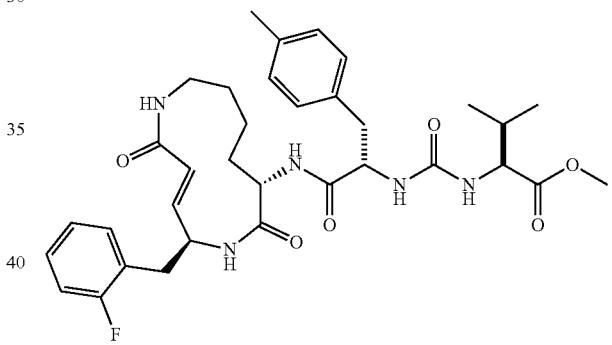

Figure 16:
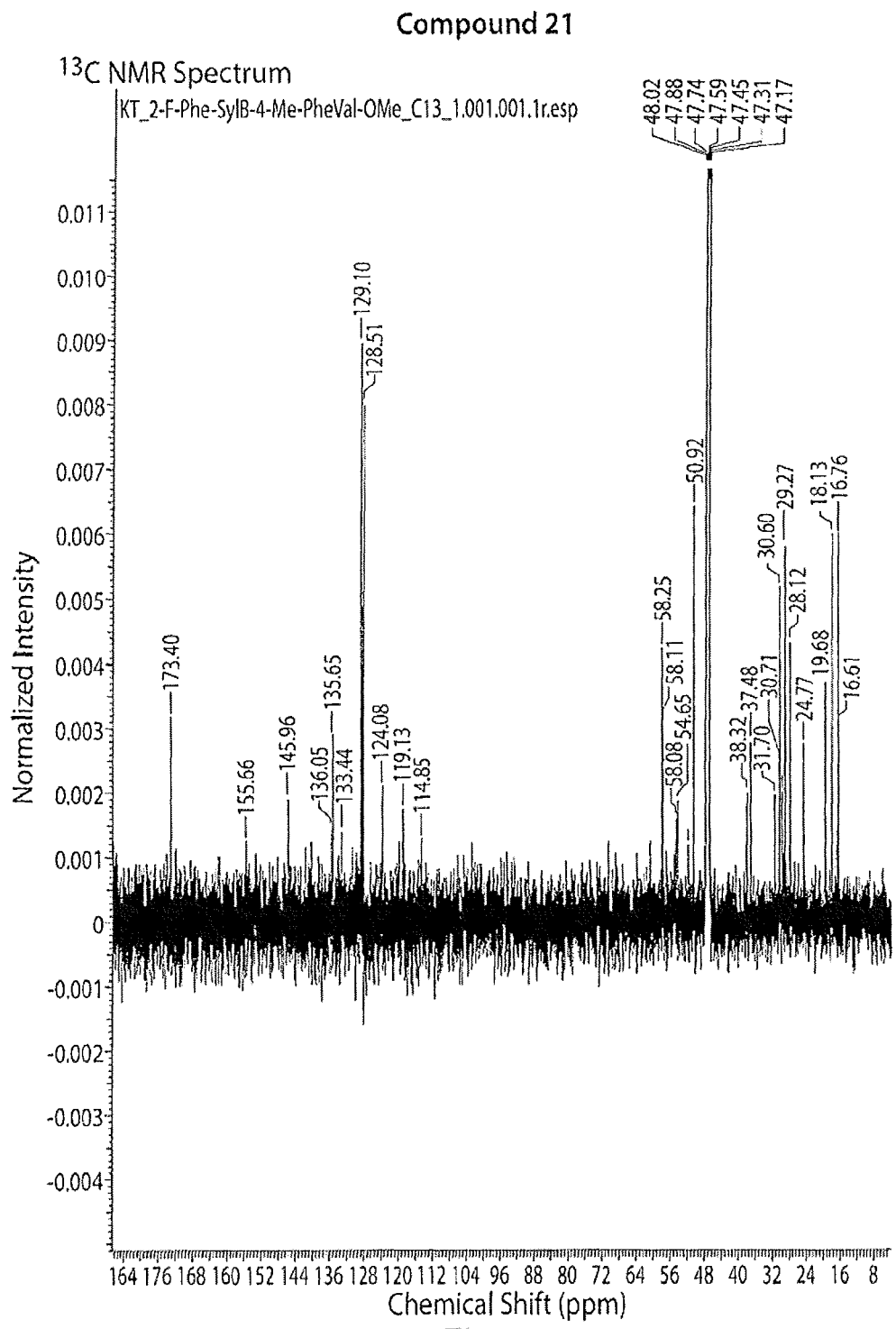
FIG. 16 shows the $^{13}$C NMR for compound 21.

NMR $^{13}$C (150 MHz, MeOD-d$_4$) spectrum shown in FIG. 16.

(S)-methyl 2-(3-((S)-1-((5S,8S,E)-5-(2-fluorobenzyl)-2,7-dioxo-1,6-diazacyclododec-3-en-8-ylamino)-3-(3-fluorophenyl)-1-oxopropan-2-yl) ureido)-3-methylbutanoate (22)

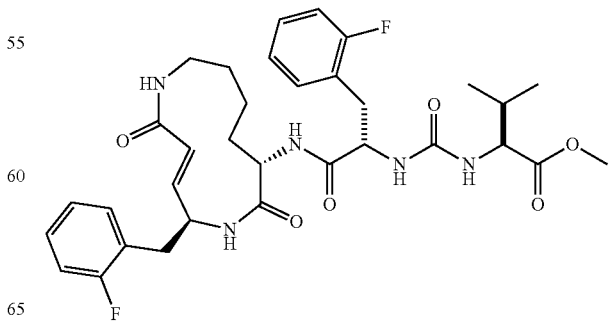

Figure 17A:
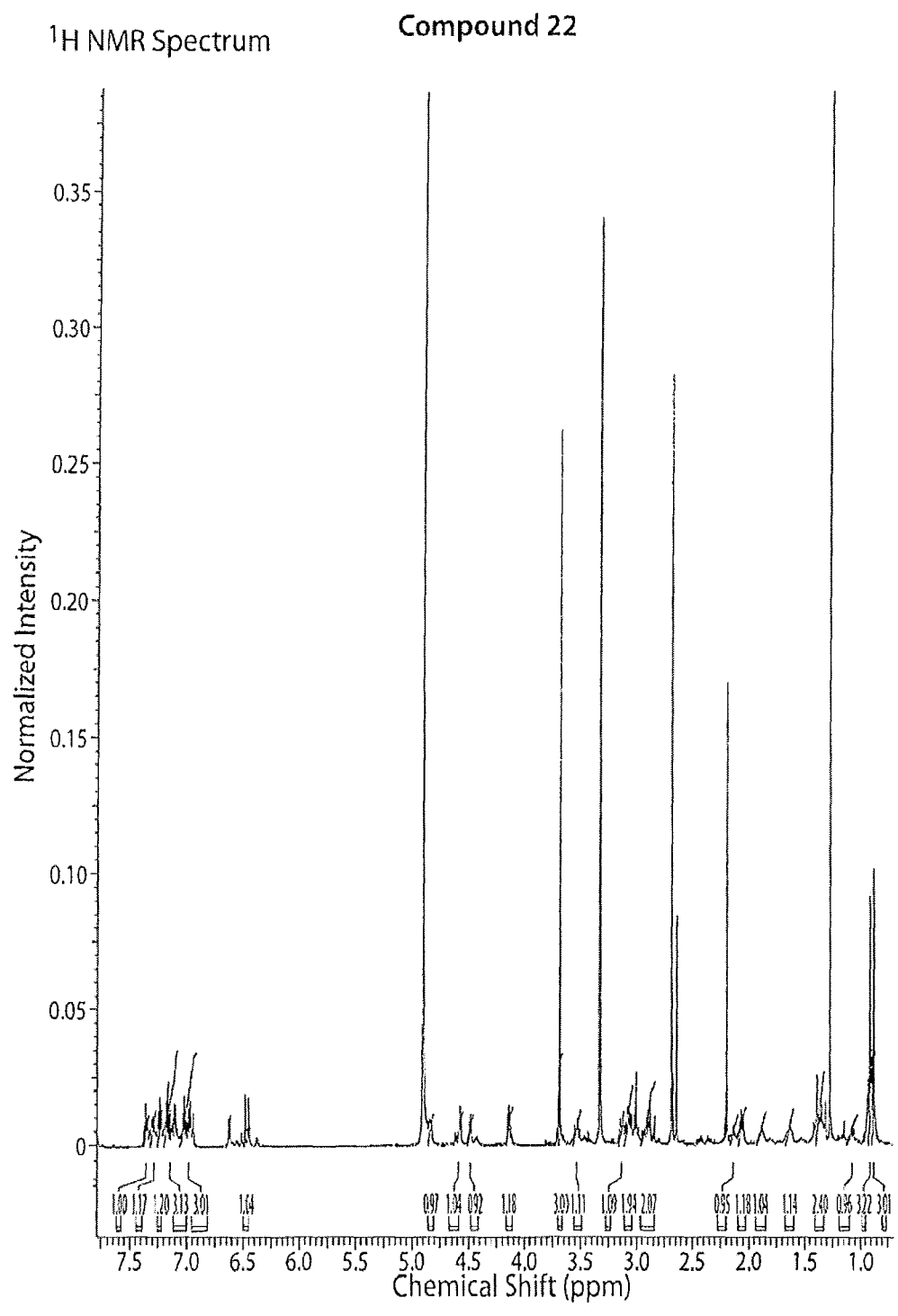
FIGS. 17A-17B show the $^{1}$H NMR and $^{13}$C NMR, respectively, for compound 22.
Figure 17B:
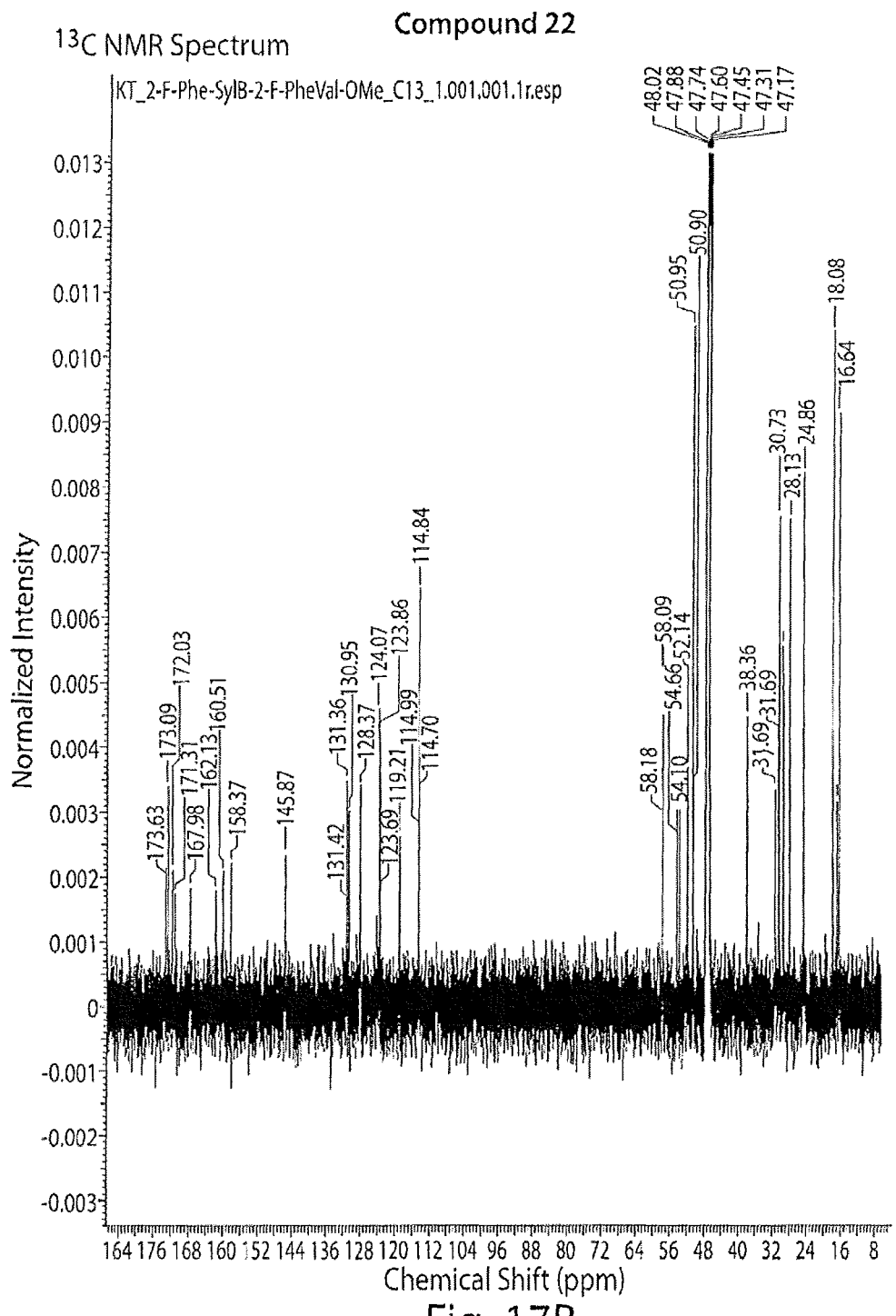

NMR ¹H (600 MHz, MeOD-d₄) spectrum shown in FIG. 17A; NMR ¹³C (150 MHz, MeOD-d₄) spectrum shown in FIG. 17B.

(S)-methyl 2-(3-((S)-1-((5S,8S,E)-5-(2-fluorobenzyl)-2,7-dioxo-1,6-diazacyclododec-3-en-8-ylamino)-3-(3-fluorophenyl)-1-oxopropan-2-yl)ureido)-3-methylbutanoate (23)

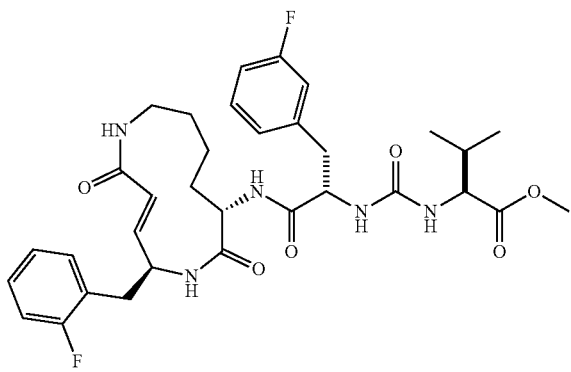 [SMILES: COC(=O)[C@@H](NC(=O)N[C@@H](Cc1cccc(F)c1)C(=O)N[C@H]1CCCCNC(=O)/C=C/[C@H](Cc2ccccc2F)NC1=O)C(C)C]

Figure 18A:
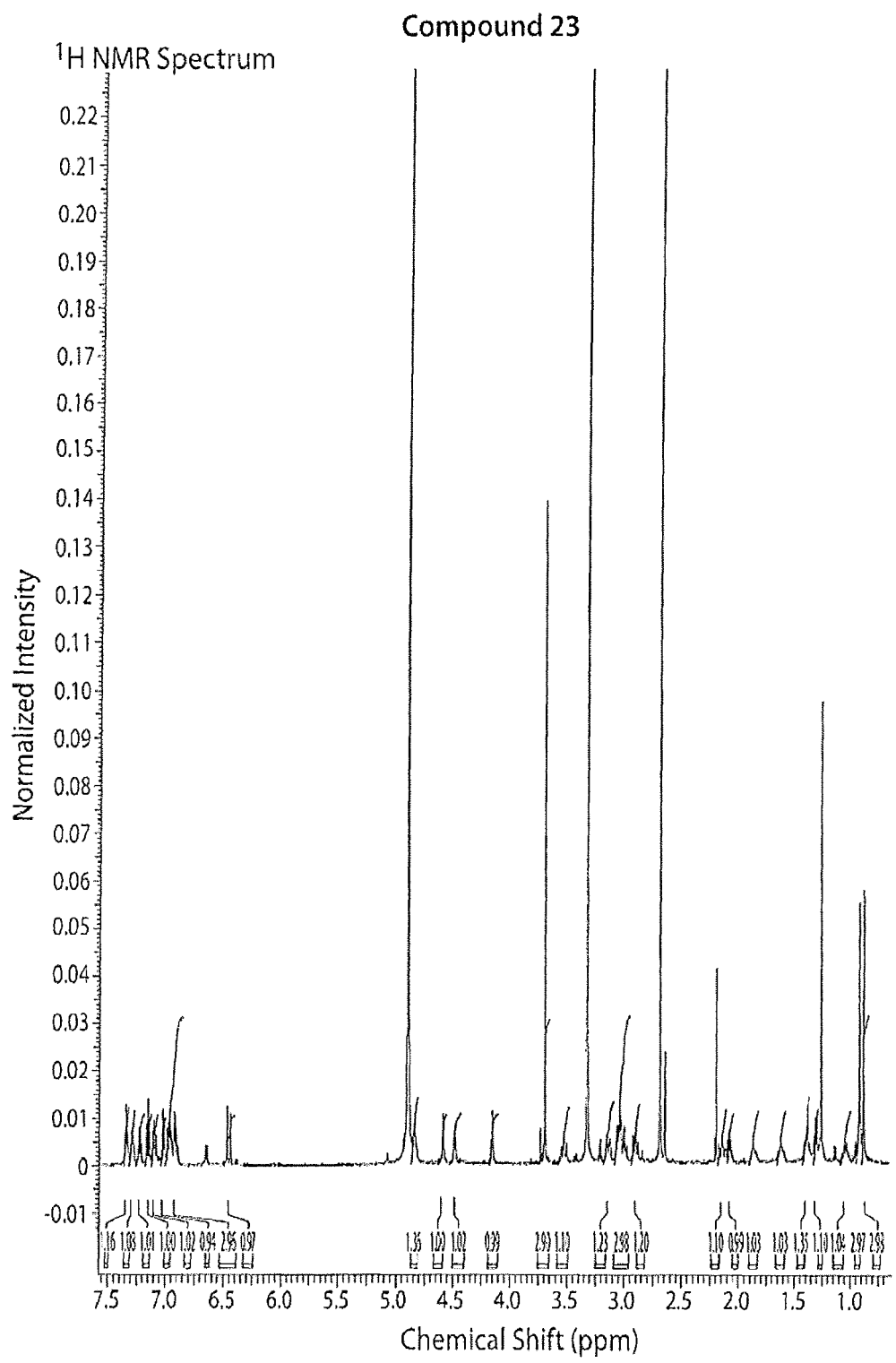
FIGS. 18A-18B show the $^{1}$H NMR and $^{13}$C NMR, respectively, for compound 23.
Figure 18B:
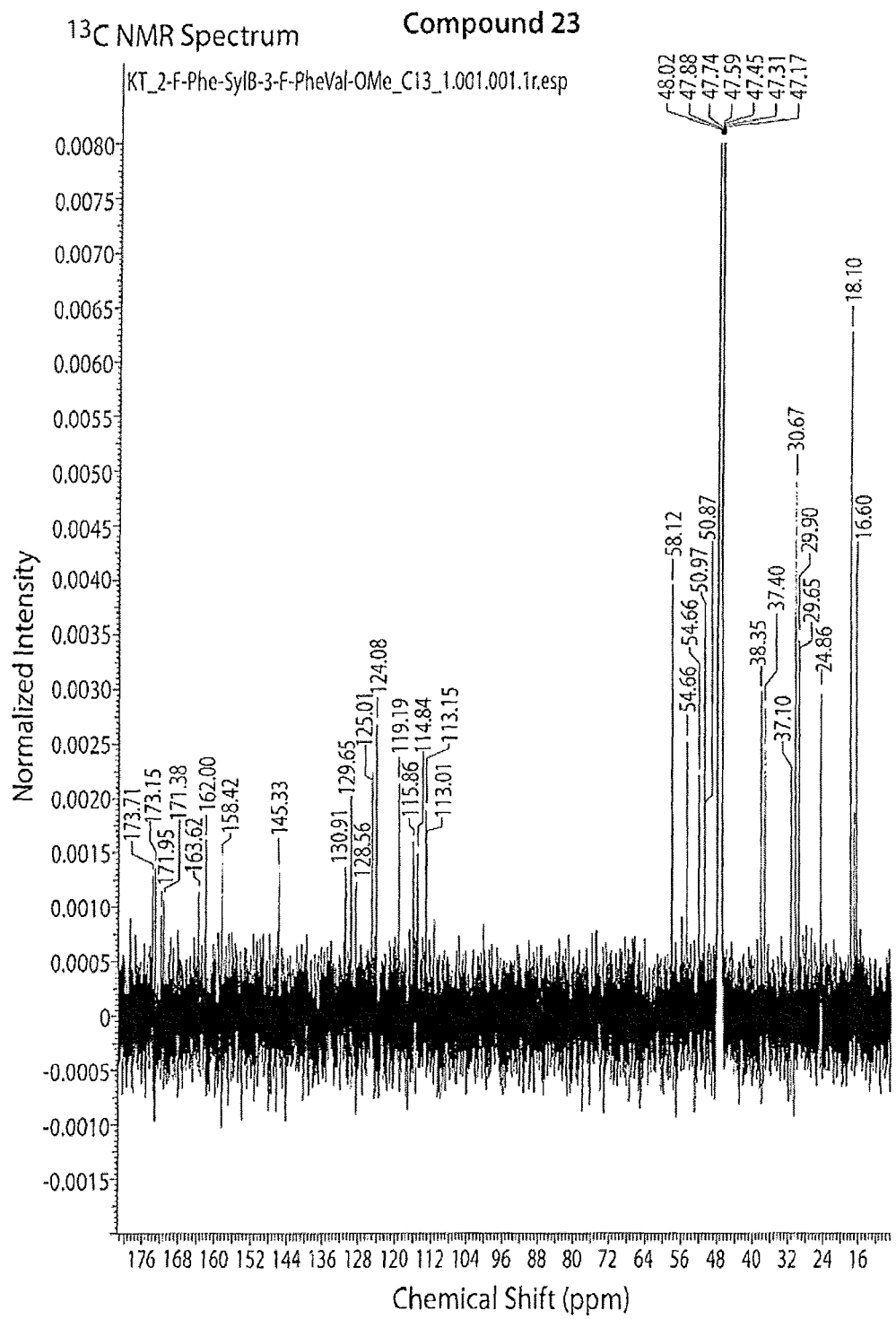

NMR ¹H (600 MHz, MeOD-d₄) spectrum shown in FIG. 18A; NMR ¹³C (150 MHz, MeOD-d₄) spectrum shown in FIG. 18B.

(S)-methyl 2-(3-((S)-3-(2-chlorophenyl)-1-((5S,8S,E)-5-(3-fluorobenzyl)-2,7-dioxo-1,6-diazacyclododec-3-en-8-ylamino)-1-oxopropan-2-yl)ureido)-3-methylbutanoate (24)

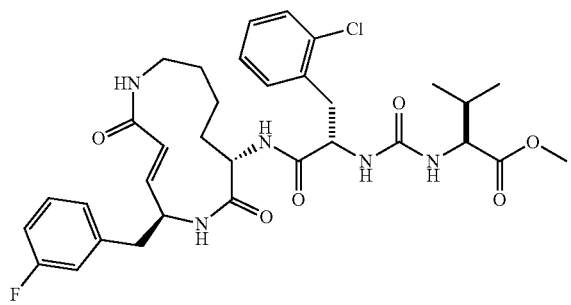

Figure 19A:
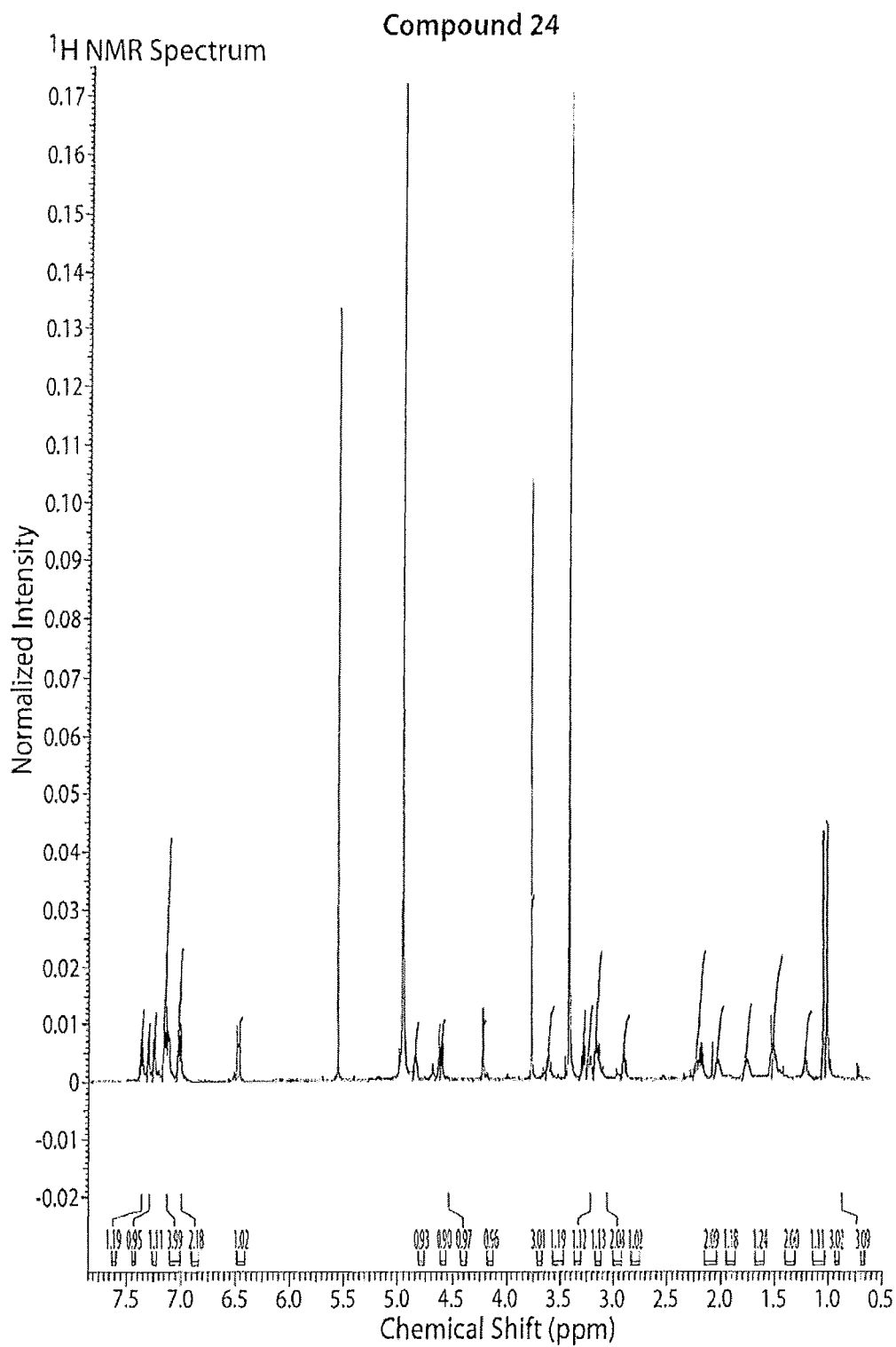
FIGS. 19A-19B show the $^{1}$H NMR and $^{13}$C NMR, respectively, for compound 24.
Figure 19B:
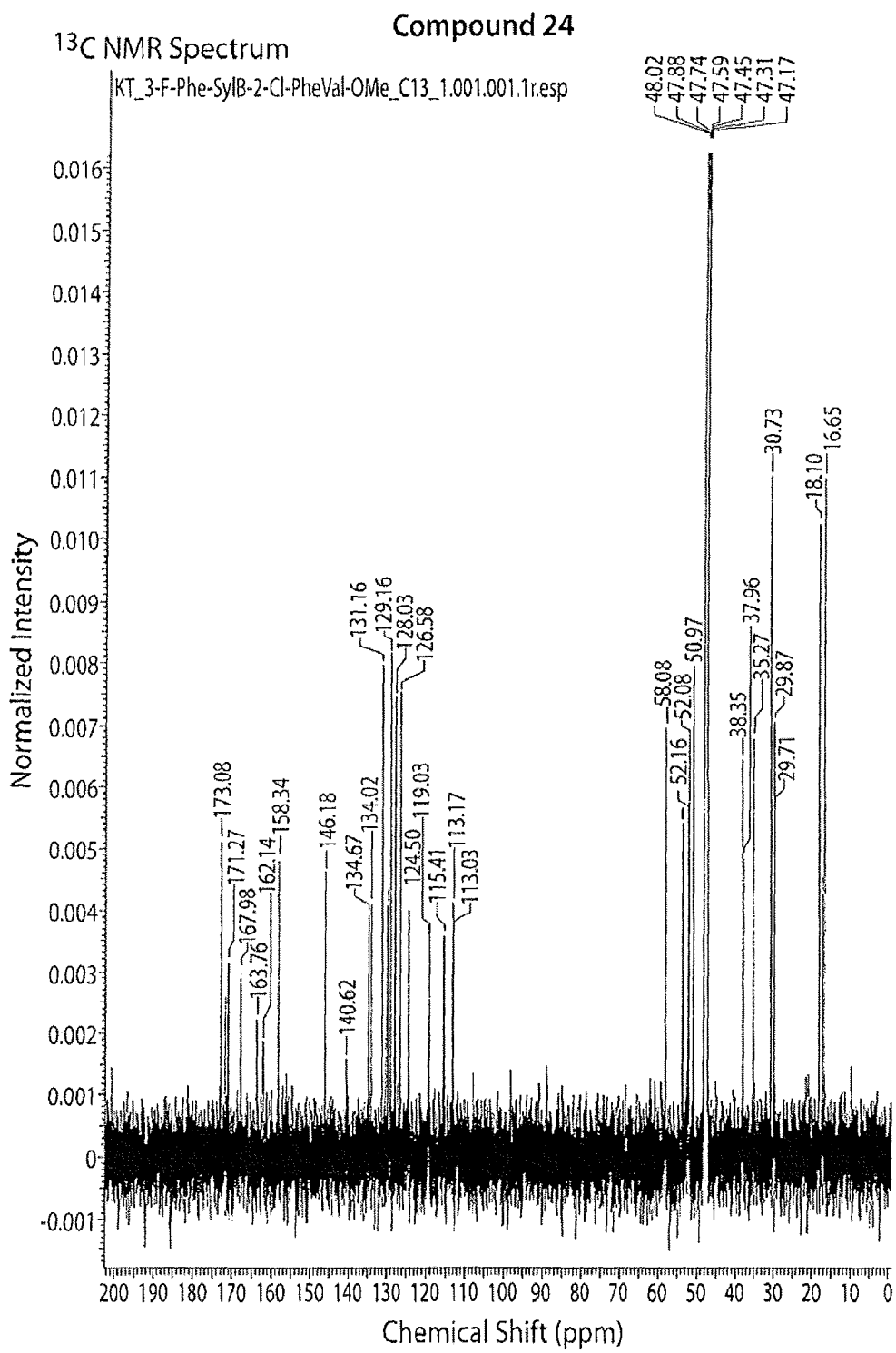

NMR ¹H (600 MHz, MeOD-d₄) spectrum shown in FIG. 19A; NMR ¹³C (150 MHz, MeOD-d₄) spectrum shown in FIG. 19B.

(S)-methyl 2-(3-((S)-3-(3-chlorophenyl)-1-((5S,8S,E)-5-(3-fluorobenzyl)-2,7-dioxo-1,6-diazacyclododec-3-en-8-ylamino)-1-oxopropan-2-yl)ureido)-3-methylbutanoate (25)

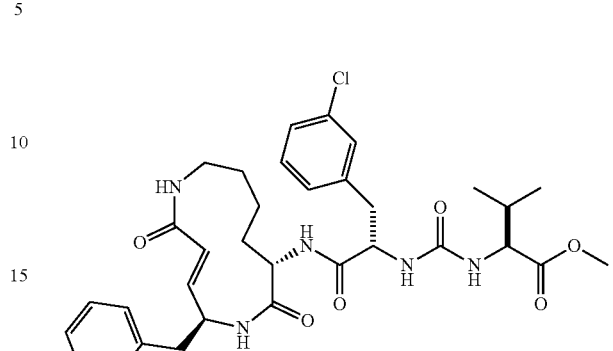

Figure 20A:
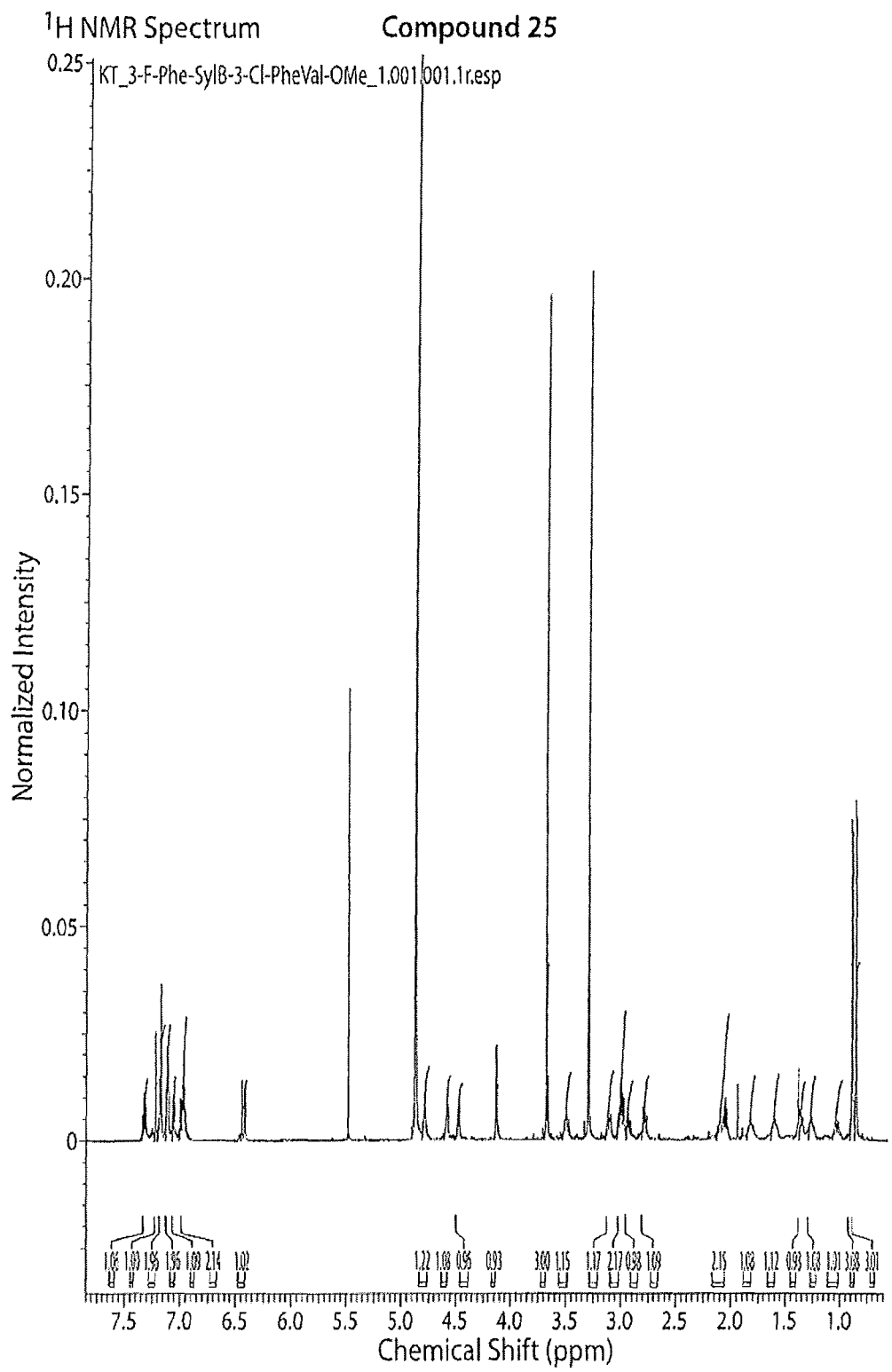
FIGS. 20A-20B show the $^{1}$H NMR and $^{13}$C NMR, respectively, for compound 25.
Figure 20B:
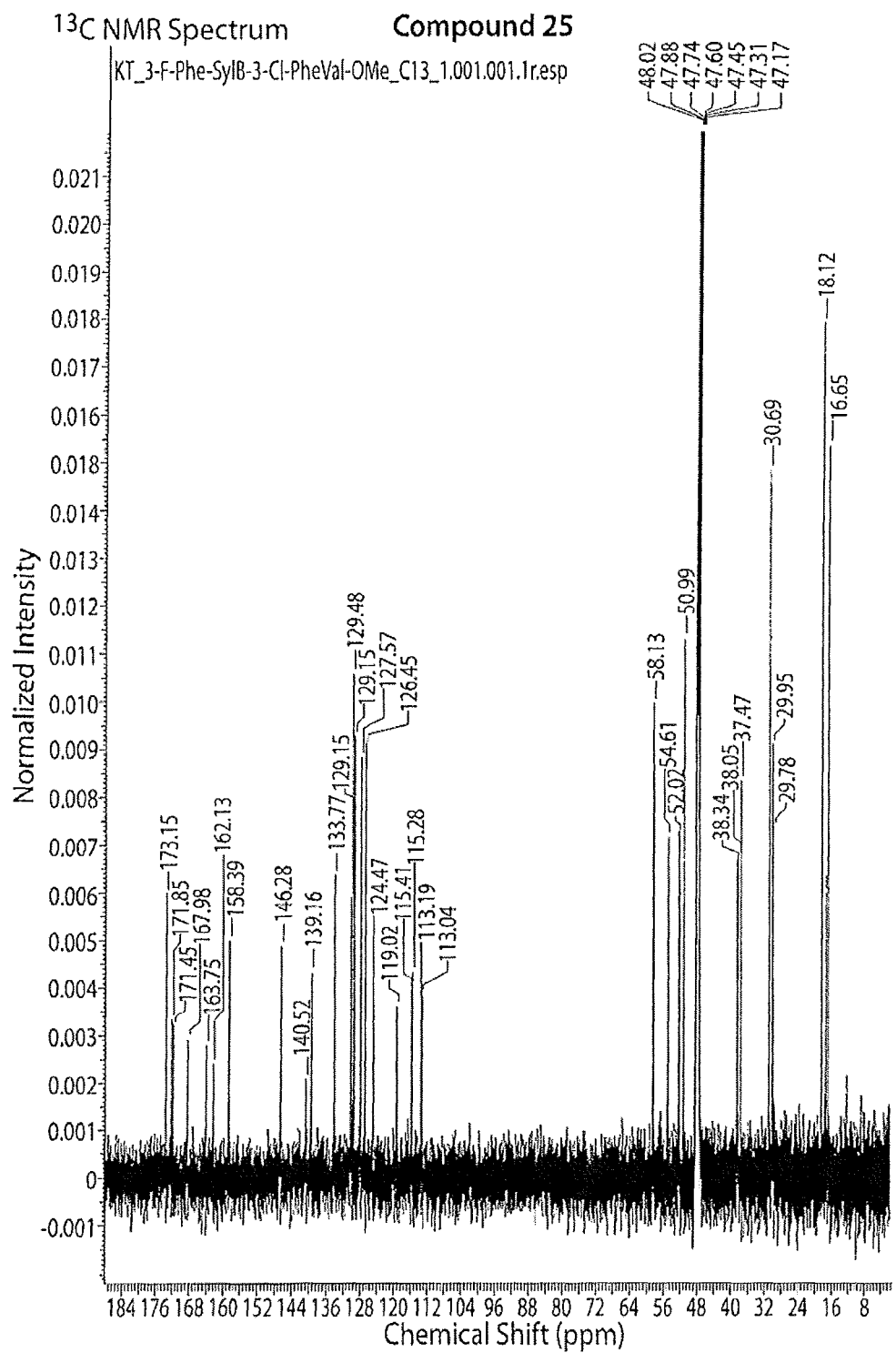

NMR ¹H (600 MHz, MeOD-d₄) spectrum shown in FIG. 20A; NMR ¹³C (150 MHz, MeOD-d₄) spectrum shown in FIG. 20B.

(S)-methyl 2-(3-((S)-3-(4-chlorophenyl)-1-((5S,8S,E)-5-(3-fluorobenzyl)-2,7-dioxo-1,6-diazacyclododec-3-en-8-ylamino)-1-oxopropan-2-yl)ureido)-3-methylbutanoate (26)

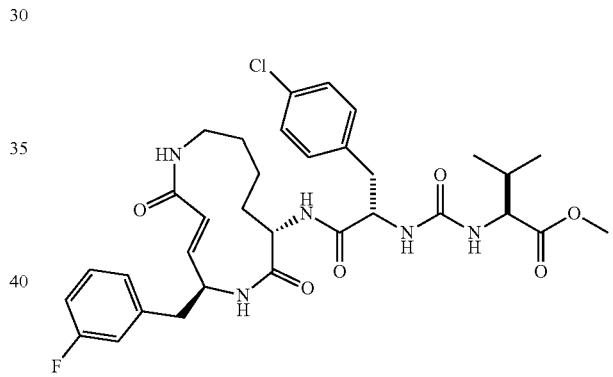

Figure 21A:
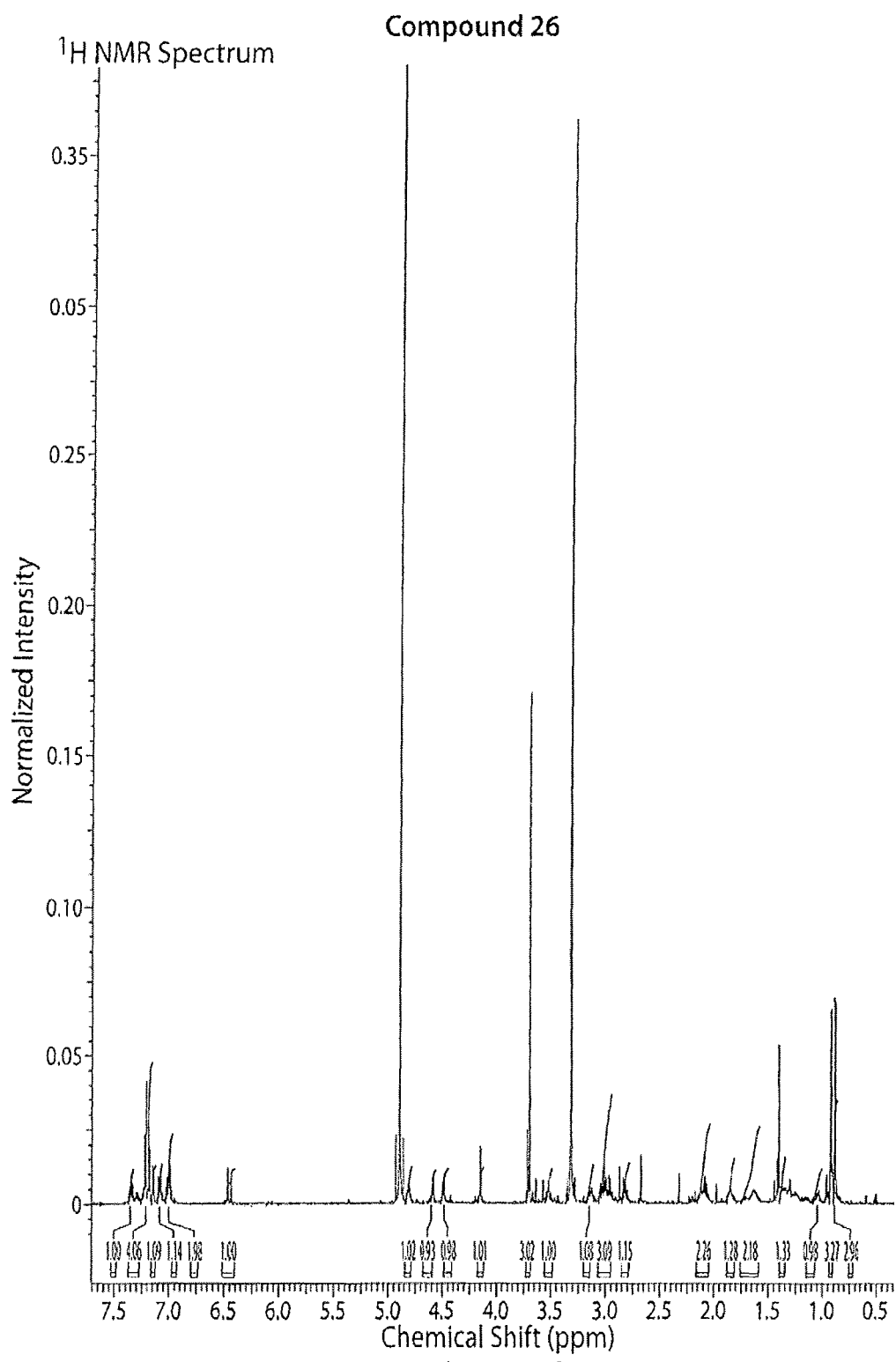
FIGS. 21A-21B show the $^{1}$H NMR and $^{13}$C NMR, respectively, for compound 26.
Figure 21B:
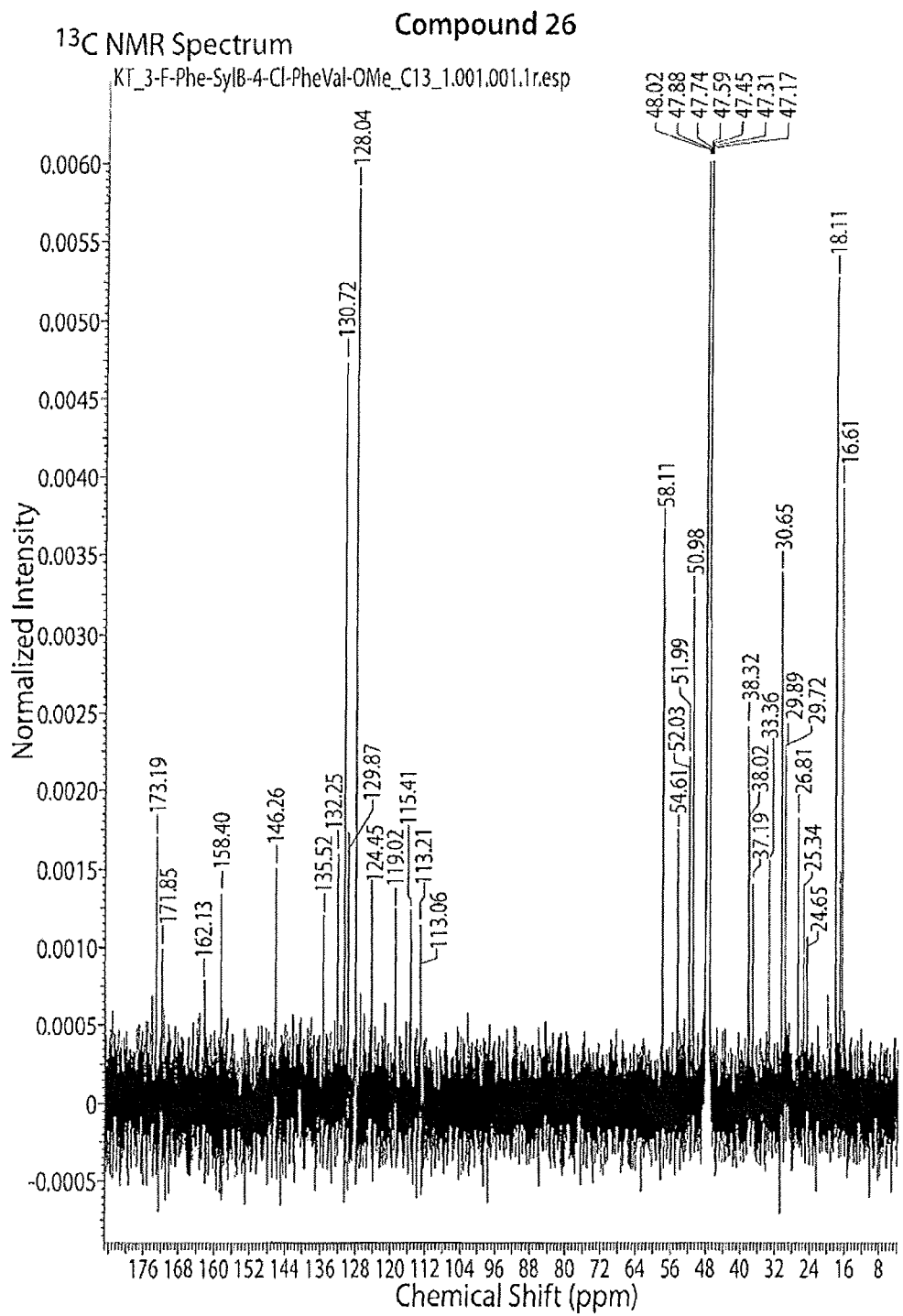

NMR ¹H (600 MHz, MeOD-d₄) spectrum shown in FIG. 21A; NMR ¹³C (150 MHz, MeOD-d₄) spectrum shown in FIG. 21B.

(S)-methyl 2-(3-((S)-1-(5S,8S,E)-S-(3-fluorobenzyl)-2,7-dioxo-1,6-diazacyclododec-3-en-8-ylamino)-1-oxo-3-phenylpropan-2-yl) ureido)-3-methylbutanoate (27)

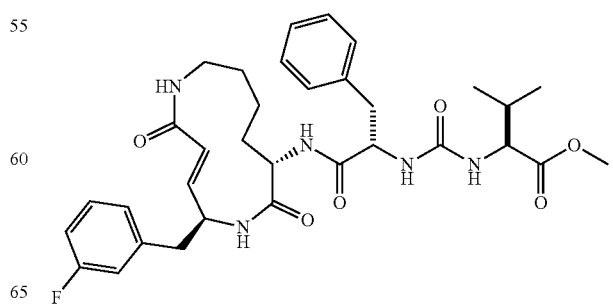

Figure 22A:
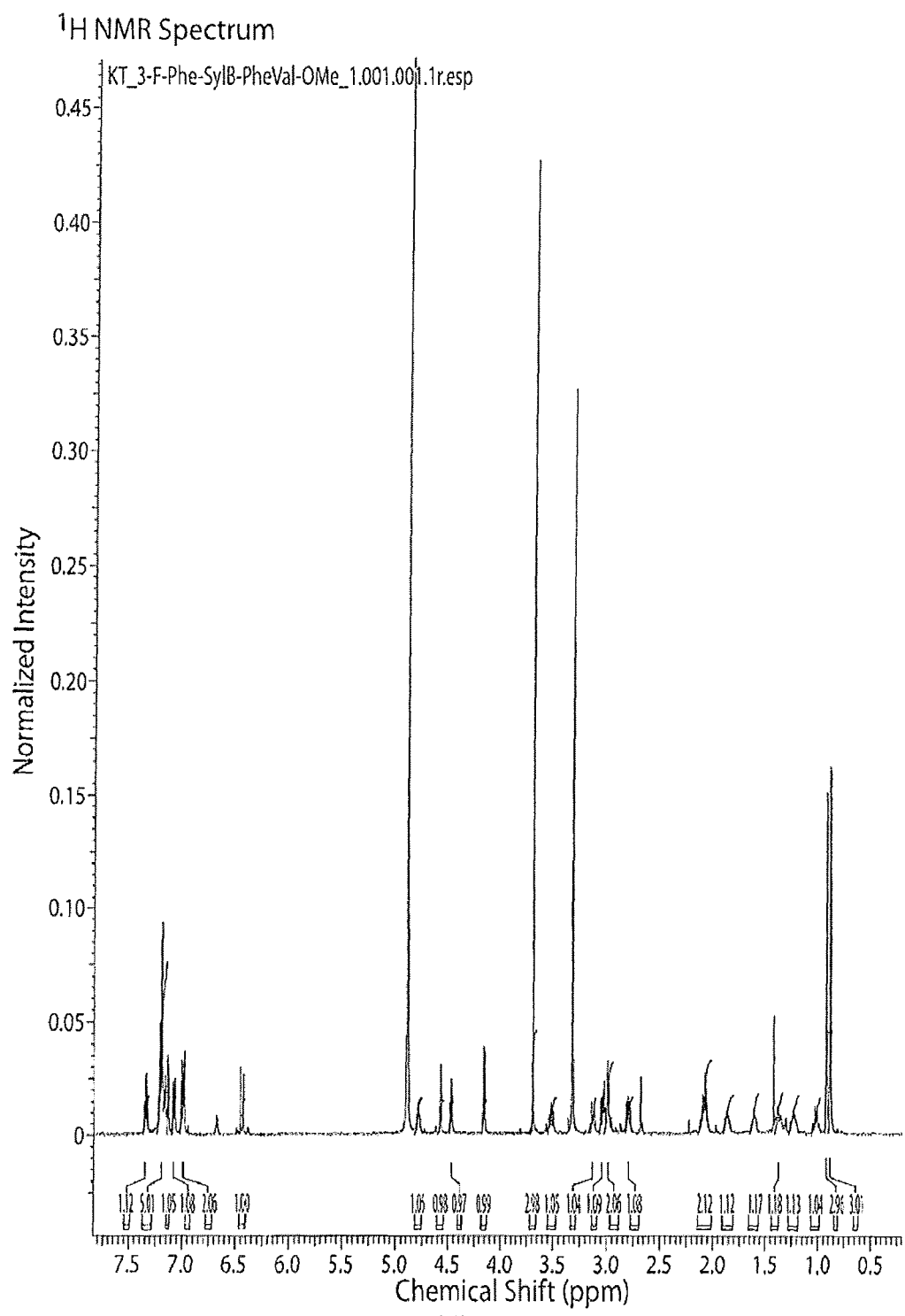
FIGS. 22A-22B show the $^{1}$H NMR and $^{13}$C NMR, respectively, for compound 27.
Figure 22B:
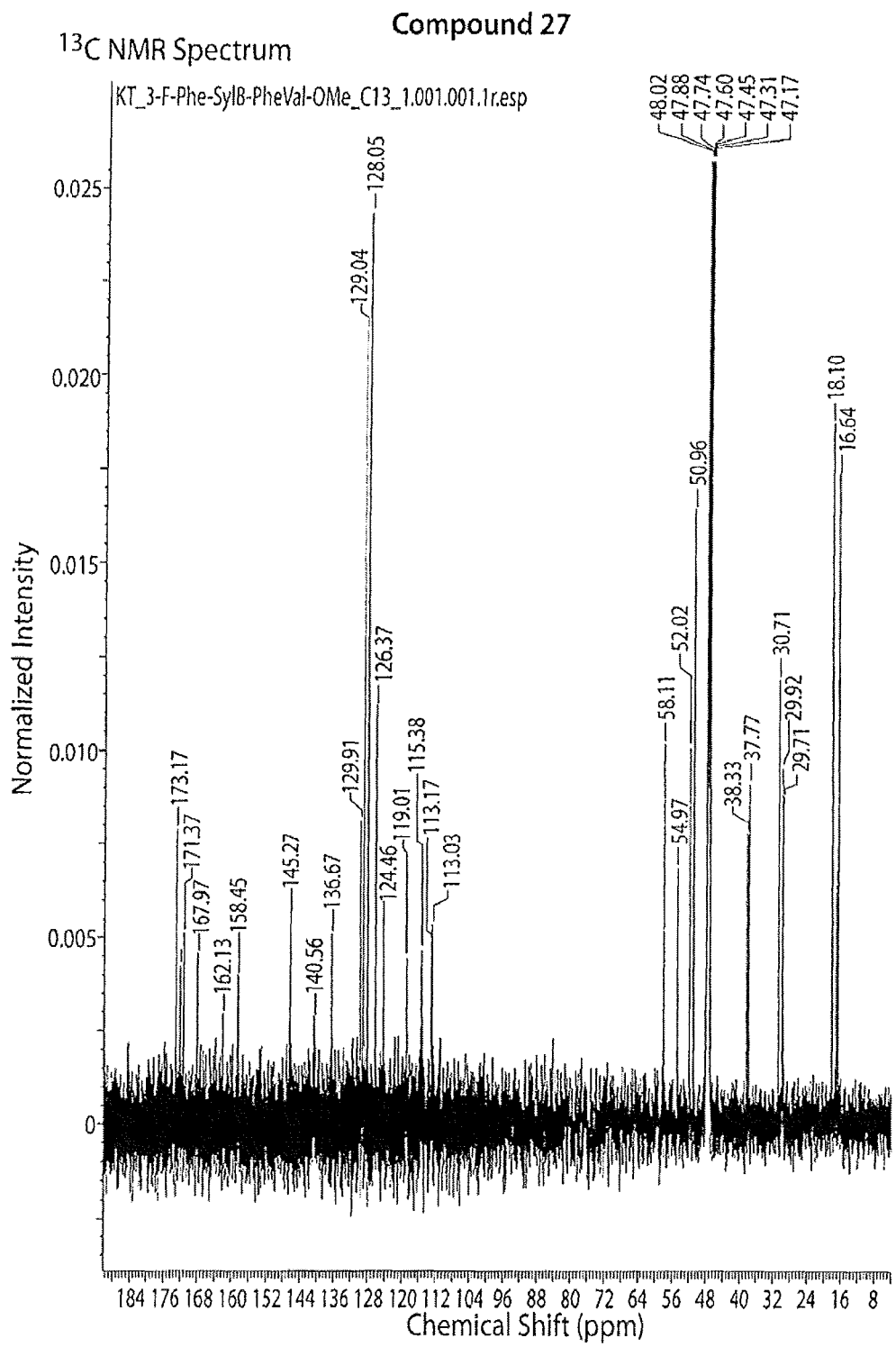

NMR ¹H (600 MHz, MeOD-d₄) spectrum shown in FIG. 22A; NMR ¹³C (150 MHz, MeOD.d₄) spectrum shown in FIG. 22B.

(S)-methyl 2-(3-((S)-1-((5S,8S,E)-S-(3 fluorobenzyl)-2,7-dioxo-1,6-diazacyclododec-3-en-8-ylamino)-1-oxo-3-m-tolylpropan-2-yl)ureido)-3-methylbutanoate (28)

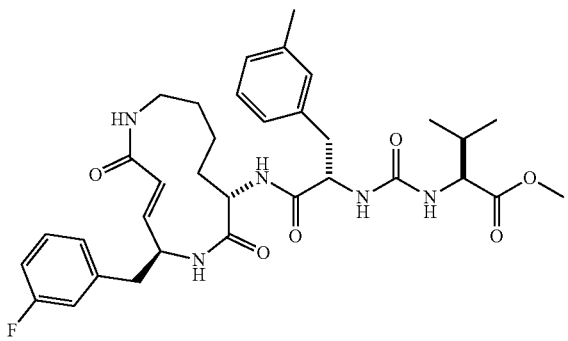 [SMILES: COC(=O)[C@@H](NC(=O)N[C@@H](Cc1cccc(C)c1)C(=O)N[C@H]1CCCCNC(=O)/C=C/[C@H](Cc2cccc(F)c2)NC1=O)C(C)C]

Figure 23A:
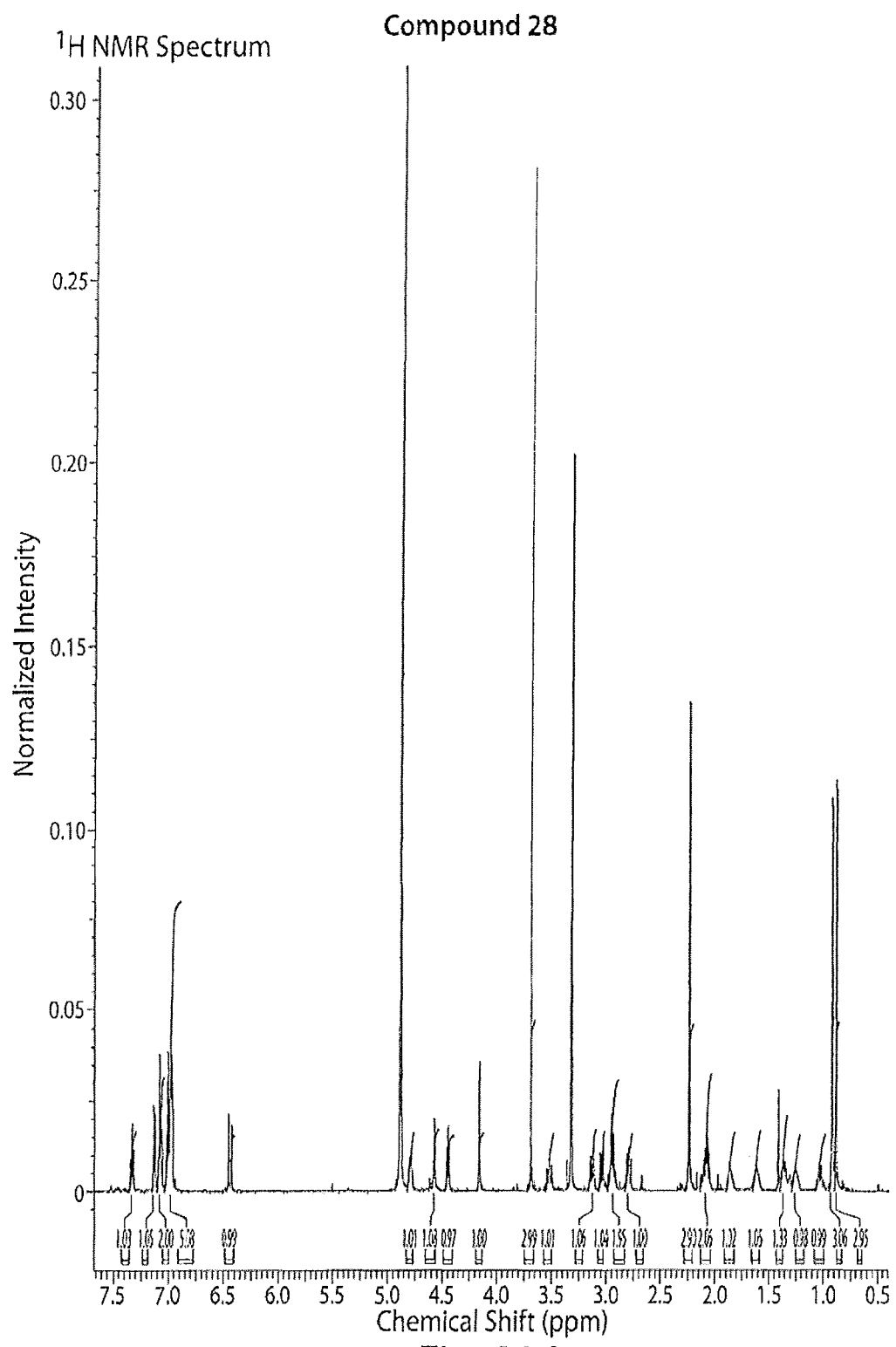
FIGS. 23A-23B show the $^{1}$H NMR and $^{13}$C NMR, respectively, for compound 28.
Figure 23B:
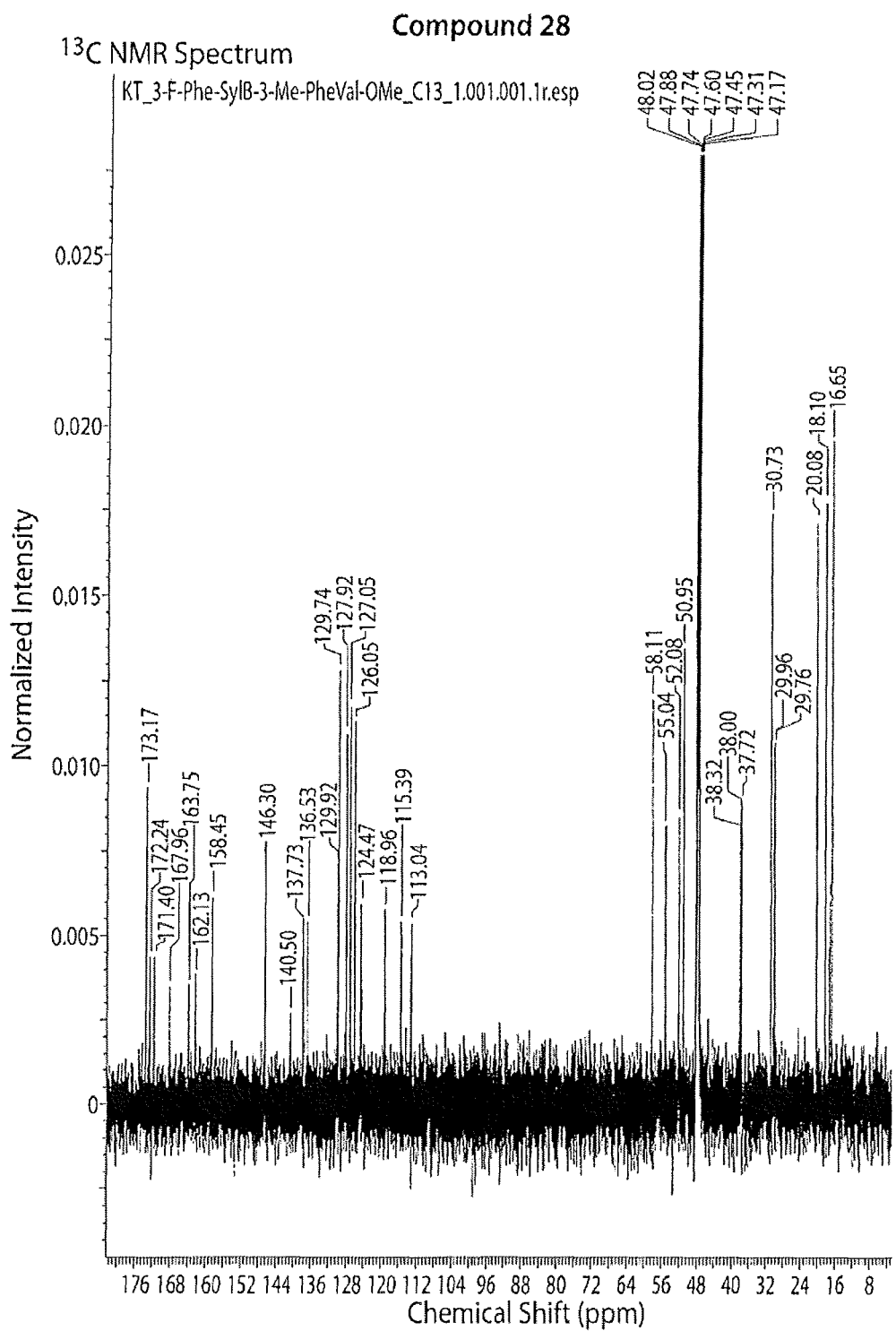

NMR ¹H (600 MHz, MeOD-d₄) spectrum shown in FIG. 23A; NMR ¹³C (150 MHz, MeOD-d₄) spectrum shown in FIG. 23B.

(S)-methyl 2-(3-((S)-1-((5S,8S,E)-S-(3-fluorobenzyl)-2,7-dioxo-1,6-diazacyclododec-3-en-8-ylamino)-1-oxo-3-p-tolylpropan-2 yl) ureido)-3-methylbutanoate (29)

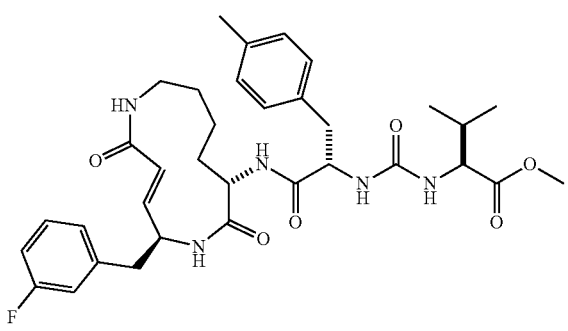 [SMILES: COC(=O)[C@@H](NC(=O)N[C@@H](Cc1ccc(C)cc1)C(=O)N[C@H]1CCCCNC(=O)/C=C/[C@H](Cc2cccc(F)c2)NC1=O)C(C)C]

Figure 24A:
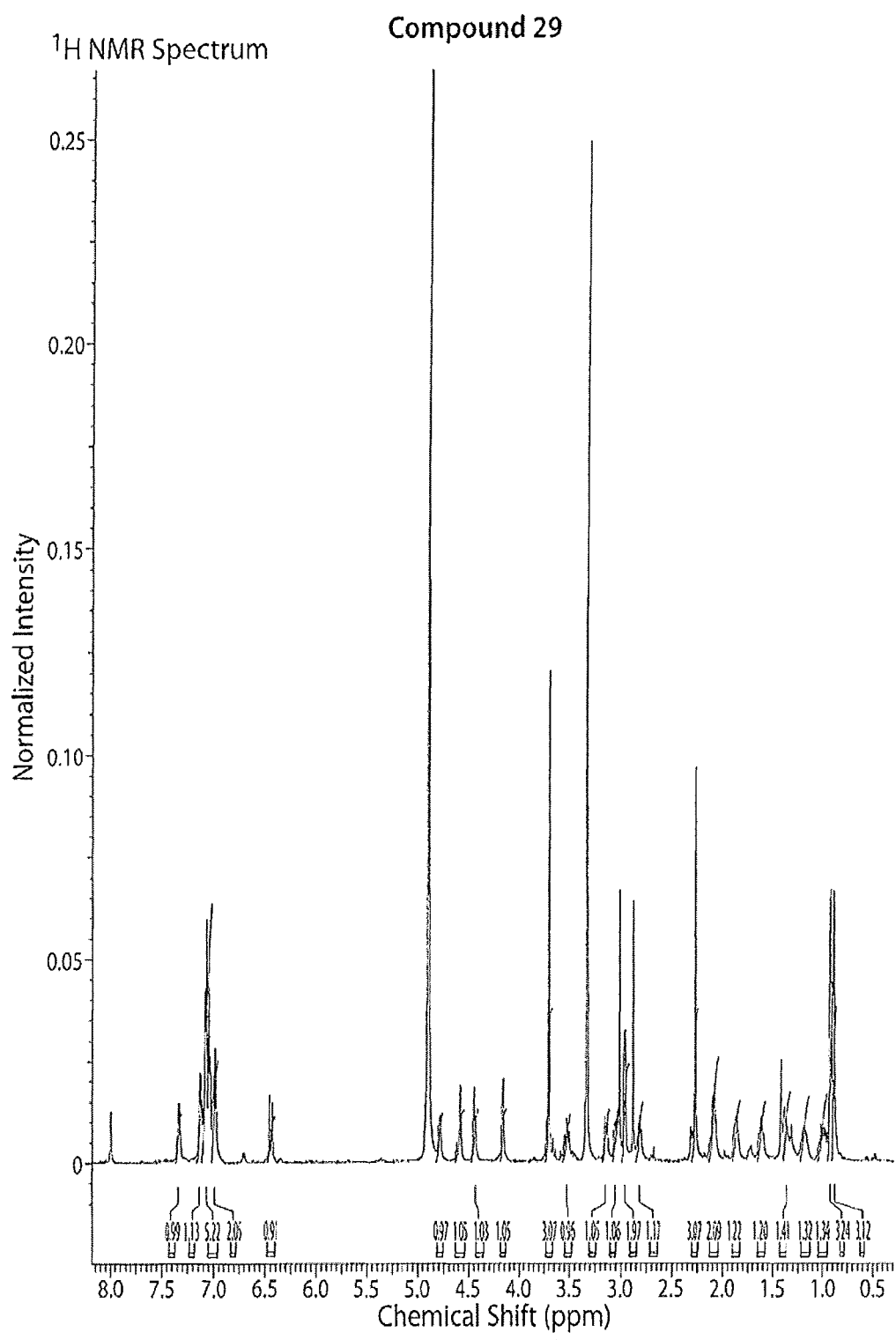
FIGS. 24A-24B show the $^{1}$H NMR and $^{13}$C NMR, respectively, for compound 29.
Figure 24B:
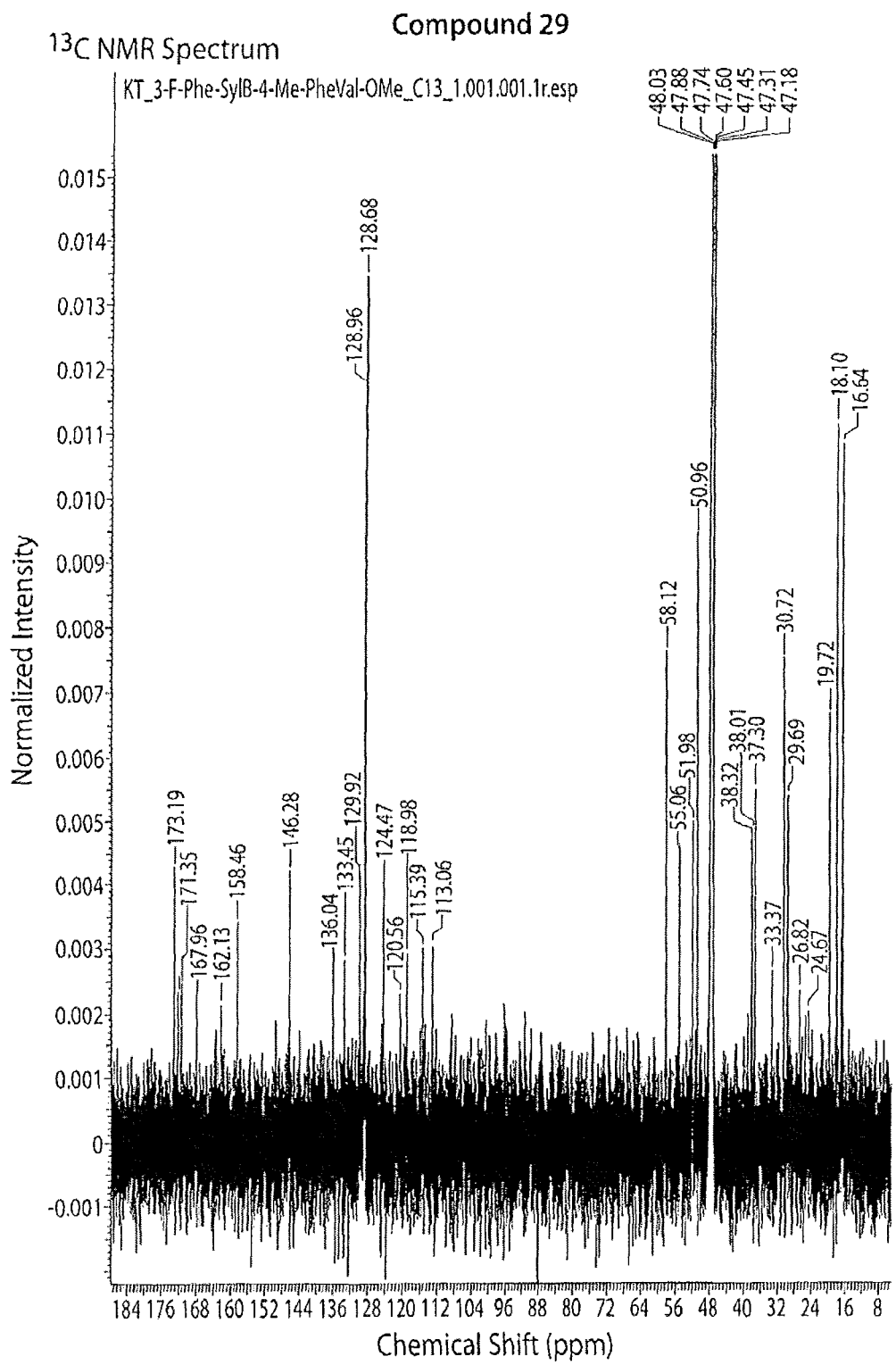

NMR ¹H (600 MHz, MeOD-d₄) spectrum shown in FIG. 24A; NMR ¹³C (150 MHz, MeOD-d₄) spectrum shown in FIG. 24B.

(S)-methyl 2-(3-((S)-1-((5S,8S,E)-S-(3-fluorobenzyl)-2,7-dioxo-1,6-diazacyclododec-3-en-8-ylamino)-3-(2-fluorophenyl)-1-oxopropan-2 yl) ureido)-3-methylbutanoate (30)

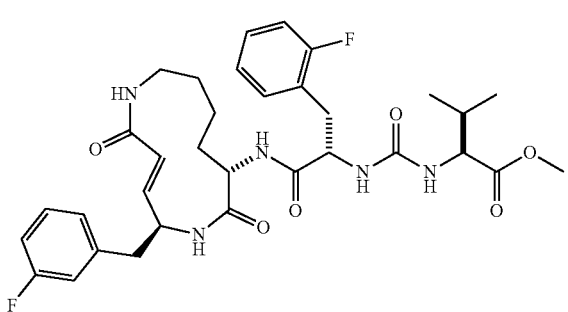

Figure 25A:
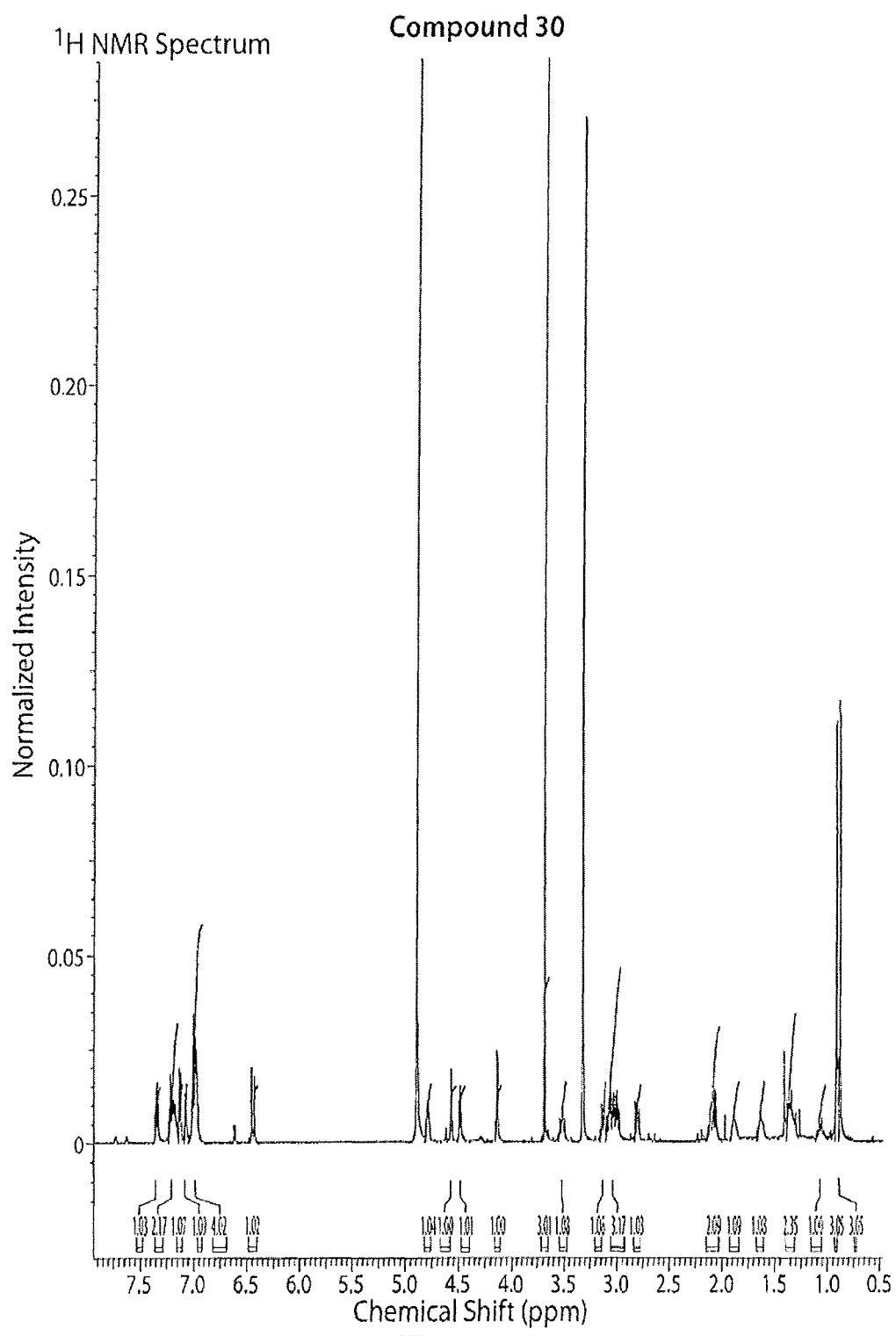
FIGS. 25A-25B show the $^{1}$H NMR and $^{13}$C NMR, respectively, for compound 30.
Figure 25B:
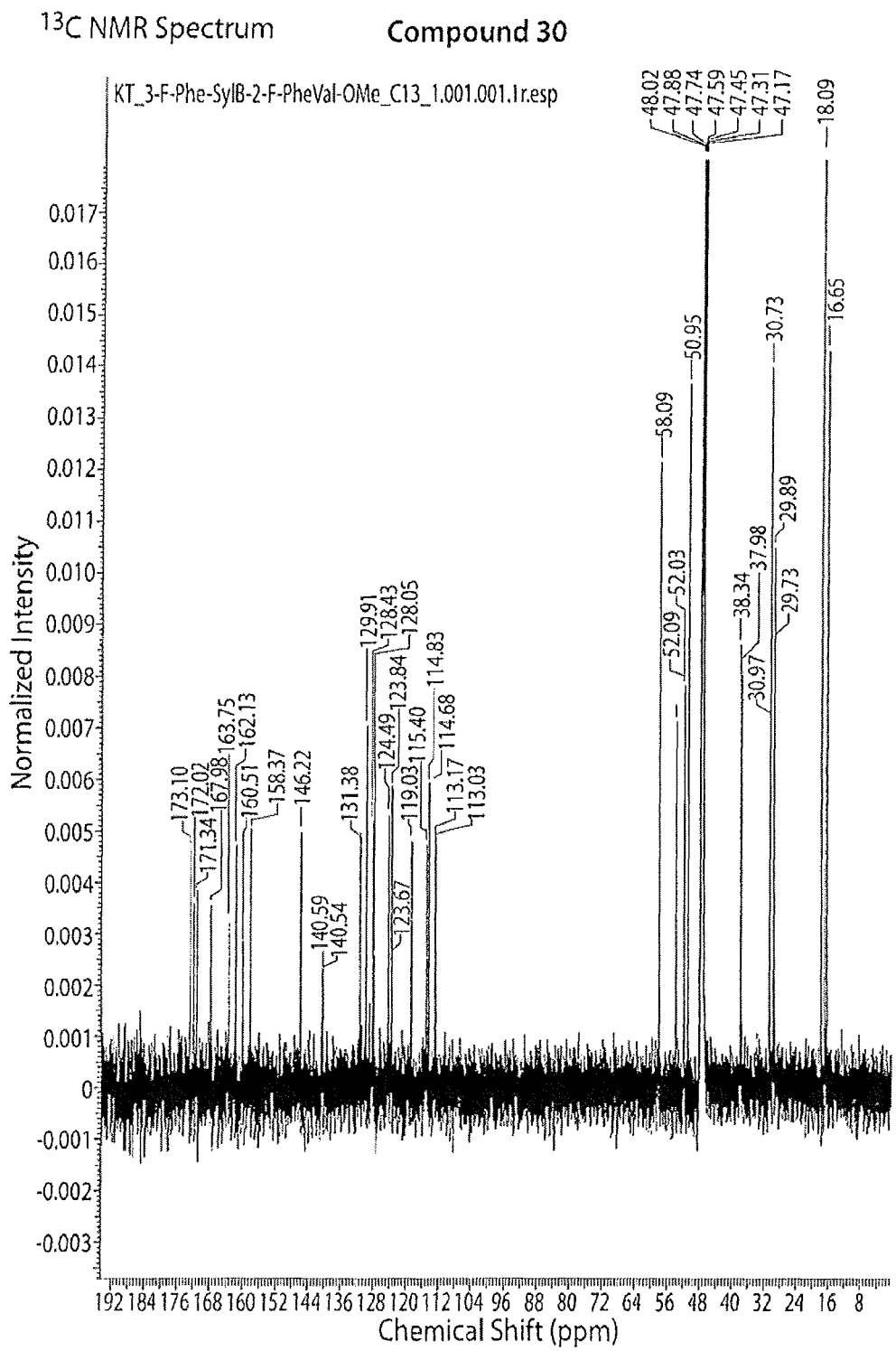

NMR ¹H (600 MHz, MeOD-d₄) spectrum shown in FIG. 25A; NMR ¹³C (150 MHz, MeOD-d₄) spectrum shown in FIG. 25B.

(S)-methyl 2-(3-((S)-1-((5S,8S,E)-5-(3-fluorobenzyl)-2,7-dioxo-1,6-diazacyclododec-3-en-8-ylamino)-3-(3-fluorophenyl)-1-oxopropan-2-yl)ureido)-3-methylbutanoate (31)

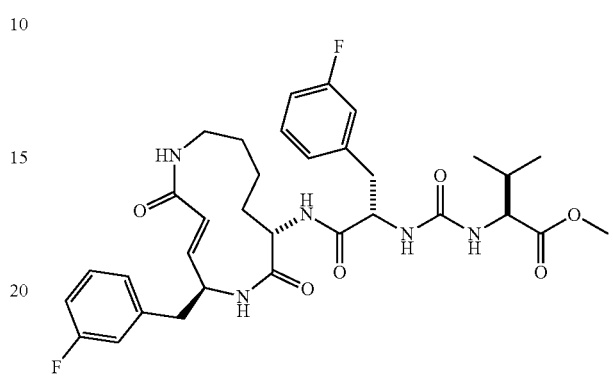

Figure 26A:
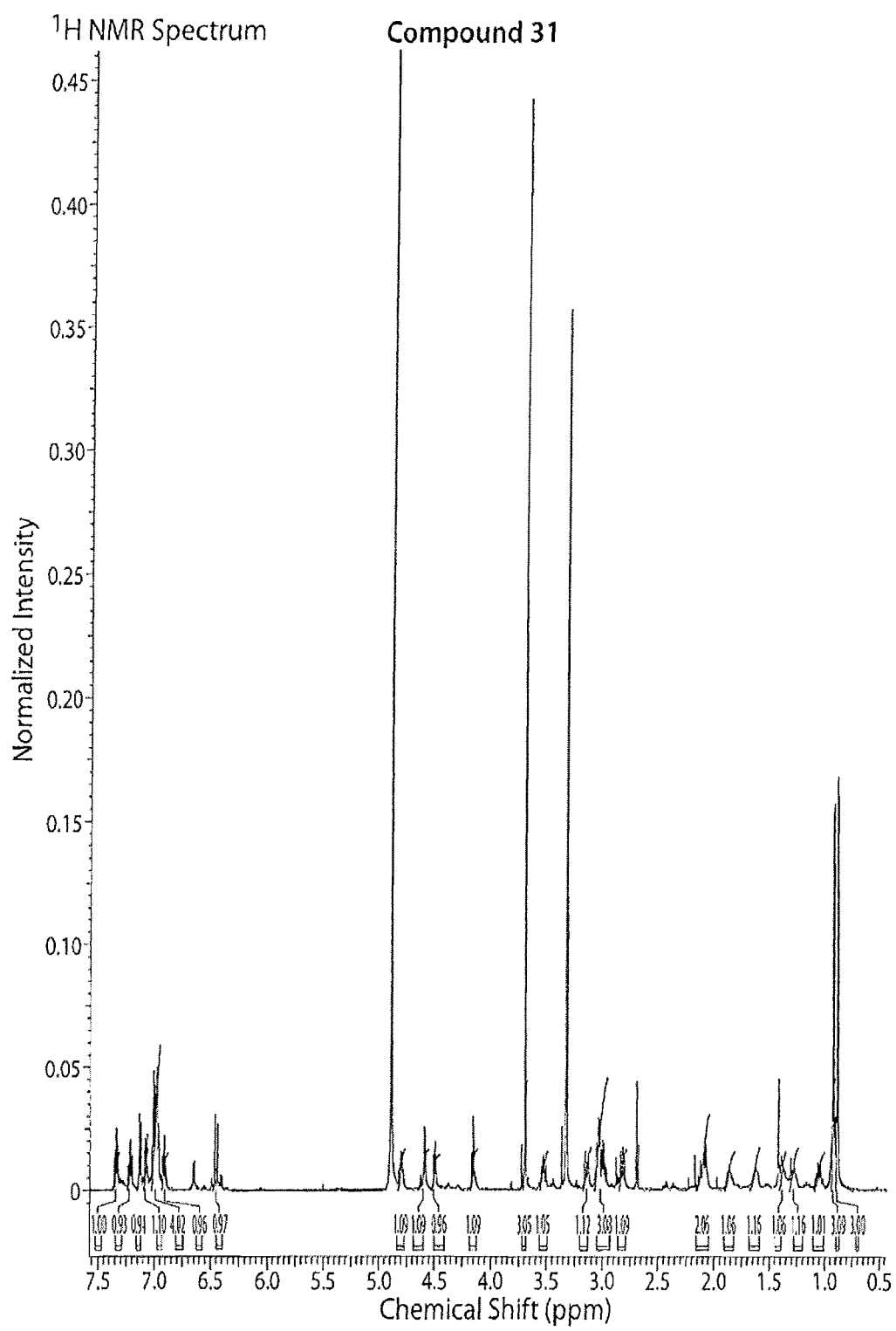
FIGS. 26A-26B show the $^{1}$H NMR and $^{13}$C NMR, respectively, for compound 31.
Figure 26B:
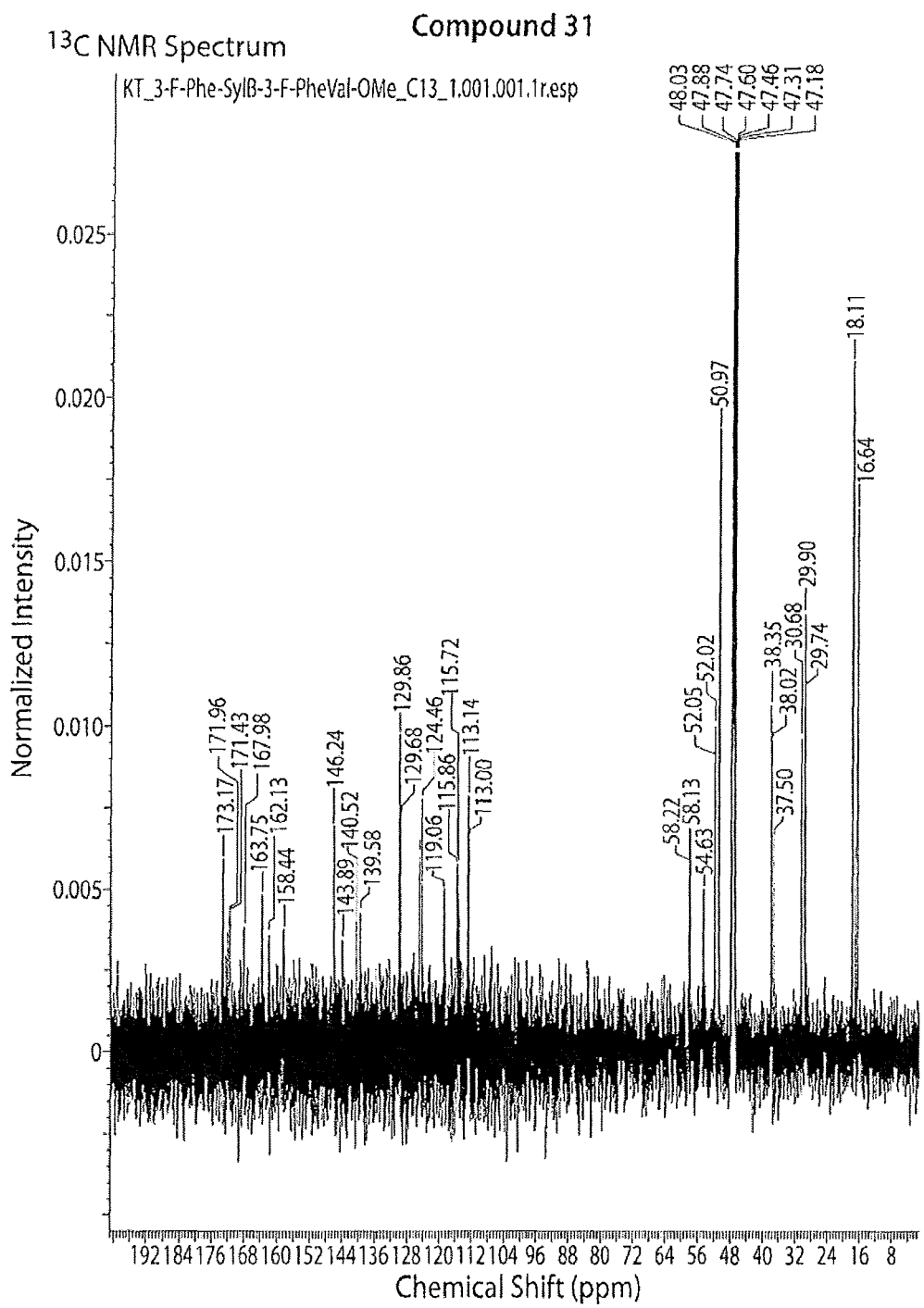

NMR ¹H (600 MHz, MeOD-d₄) spectrum shown in FIG. 26A; NMR ¹³C (150 MHz, MeOD-d₄) spectrum shown in FIG. 26B.

(S)-methyl 2-(3-((S)-1-((5S,8S,E)-5-(3-fluorobenzyl)-2,7-dioxo-1,6-diazacyclododec-3-en-8-ylamino)-1-oxo-3-(3-(trifluoromethyl)phenyl)propan-2-yl)ureido)-3-methylbutanoate (32)

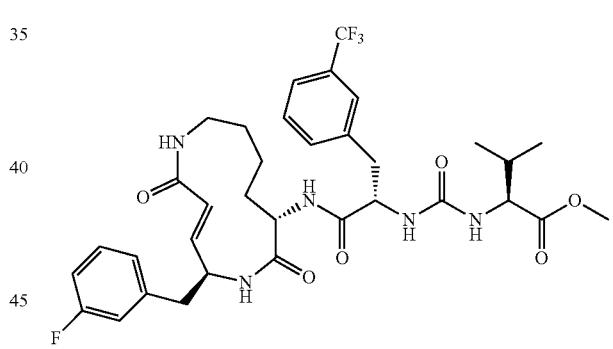

NMR 1H (600 MHz, CD3OD) δ 7.53 (s, 1H), 7.50-7.45 (m, 2H), 7.43-7.38 (m, 1H), 7.34 (td, J=7.9, 6.1 Hz, 1H), 7.14 (dt, J=7.7, 1.2 Hz, 1H), 7.08 (dt, J=9.9, 1.9 Hz, 1H), 7.03-6.97 (m, 2H), 6.46 (dd, J=0.8, 15.5 Hz, 1H), 4.81 (dt, J=9.6, 5.0 Hz, 1H), 4.62 (t, J=3.7, 1H), 4.55 (dd, 3=7.9, 5.3 Hz, 1H), 4.18-4.13 (m, 1H), 3.70 (s, 3H), 3.54 (t, J=13.4 Hz, 1H), 3.14 (dd, J=13.9, 5.1 Hz, 2H), 3.03 (td, J=5.9, 14.3 Hz, 2H), 2.83 (dd, J=14.1, 9.5 Hz, 1H), 2.15 (t, J=13.8 Hz, 1H), 2.08 (dq, J=12.2, 6.9 Hz, 1H), 1.91-1.81 (m, 1H), 1.69-1.60 (m, 1H), 1.41-1.32 (m, 3H), 1.09 (q, J=12.9 Hz, 1H), 0.93 (d, J=7.0, 3 H), 0.89 (d, J=6.8 Hz, 3H). 13C (150 MHz, CD3OD) δ 173.1, 171.4, 168.0, 162.1, 158.9, 158.4, 146.3, 140.4, 138.3, 132.9, 129.9, 128.7, 125.8, 124.4, 123.1, 119.0, 115.3, 113.0, 58.1, 54.6, 52.1, 51.0, 48.4, 48.2, 38.3, 38.1, 37.6, 30.7, 29.9, 29.7, 19.4, 18.1, 17.1, 16.6.

Example 7: Design and Synthesis

Figure 2:
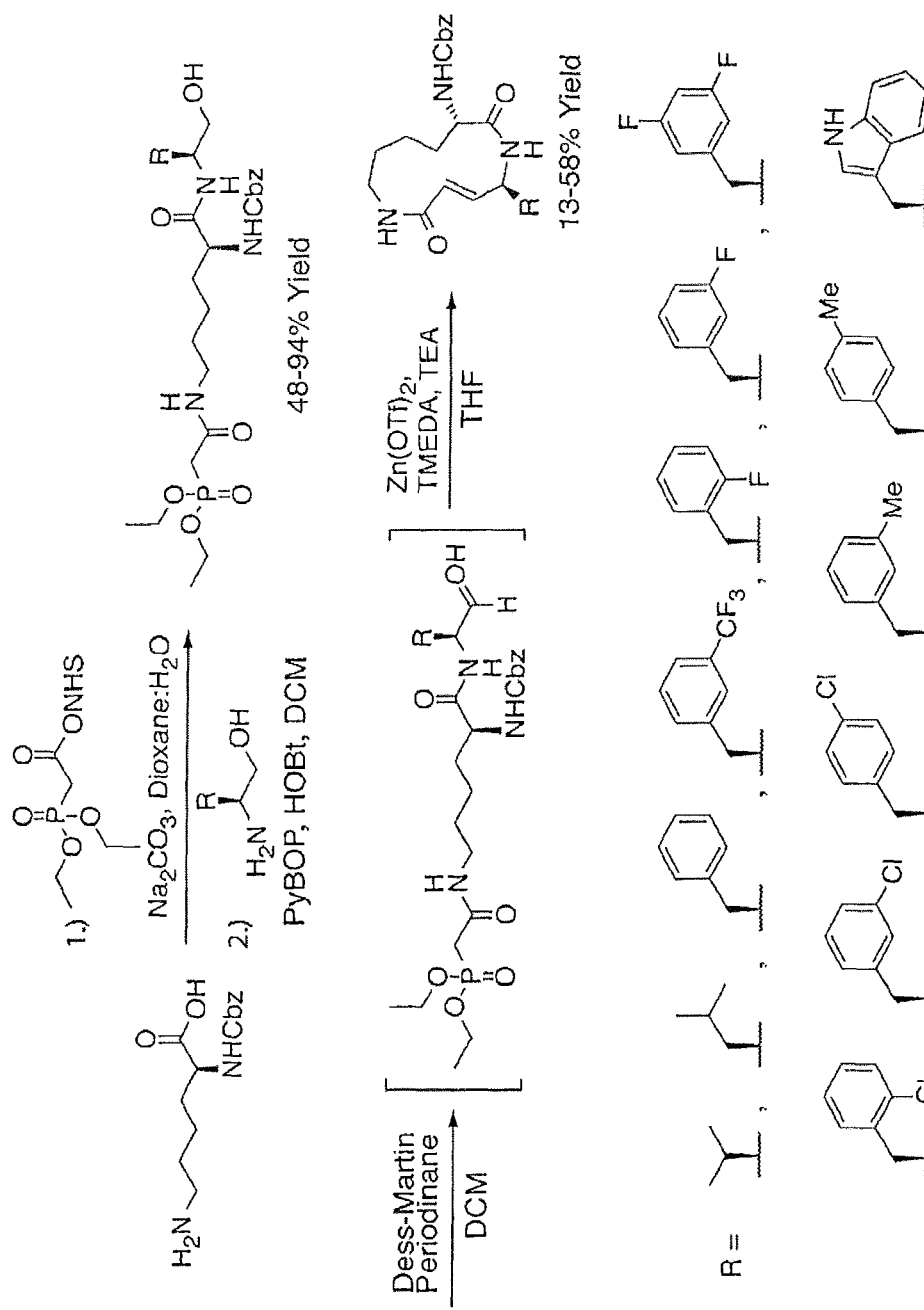
FIG. 2 is a non-limiting illustration of a synthetic route to analogues of the syringolin macrolactam.
Figure 3:
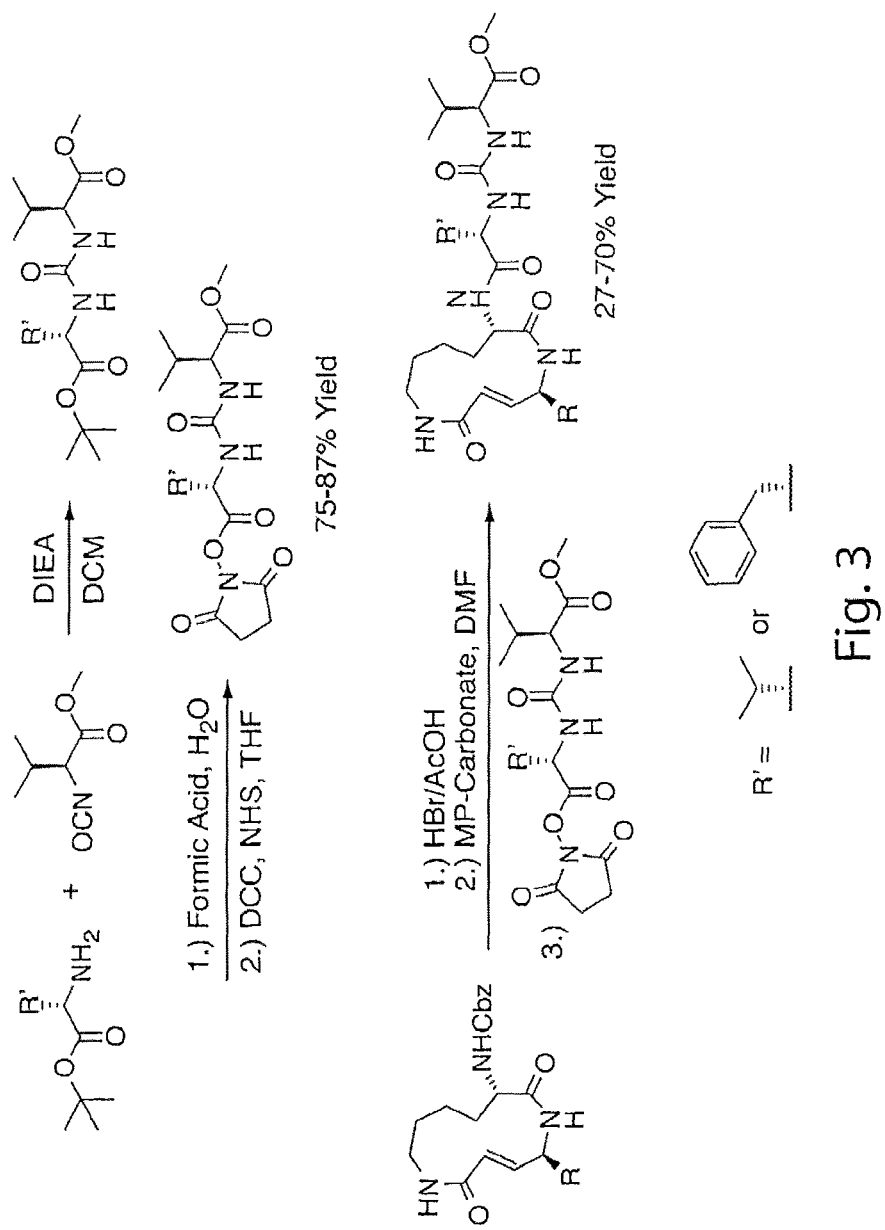
FIG. 3 is a non-limiting illustration of a synthetic route to analogues of the syringolin dipeptide urea and their coupling to macrolactams.

Syringolin analogues, which displayed modifications in the vinylogous amino acid of the macrolactam (mimic of P1 residue) and the amino acid appended to the macrocycle (mimic of P3 residue), were prepared and characterized. A convergent synthetic approach for the syntheses of syringolin B and analogues thereof was employed (FIGS. 2-3). The synthetic scheme was modular and thus amenable to diversity-oriented synthesis. For example, the linear precursor of the macrolactam is prepared from a Cbz-protected lysine residue having an acetyl phosphonate moiety on the ε-amino group and commercially available or easily synthesized 1,2-amino alcohols (FIG. 2).

The present design strategy used a phenylalaninol, tryptophanol, or close analogues of these 1,2-amino alcohols as building blocks, because their substituents mimic the aromatic side chains of the P1 residues of the preferred substrates of chymotrypsin substrates (see R groups in FIG. 2, Table 1). For the purposes of comparing analogues with aromatic substituents to those having aliphatic substituents at R, valinol and leucinol were used to prepare linear precursors of syringolin B macrolactam and the closely related compound having an isobutyl group at R, respectively (Table 1, compounds 1 and 2).

After coupling of the amino alcohols to the protected lysine and oxidation of products' primary alcohols, the reactive functionality mimicking the P1 residue of proteasome substrates was formed via an intramolecular Horner-Wadsworth-Emmons reaction. A modular route was also used for syntheses of the dipeptide urea side chain fragments which constituents mimic the P3 residue of a proteasome substrate. In total, 16 syringolin analogues having esterified side chains and varying degrees of similarity to the substrates preferred by the β5-subunit of the human proteasome were synthesized (Table 1).

Example 8: SAR Studies

Using purified human 20S proteasome (hs20S) and a fluorogenic substrate (Suc-LLVY-AMC), in vitro assays were performed to systematically assess proteasome inhibition by the syringolin analogues. The choice of substrate was based on the fact that it is preferentially acted upon by the chymotrypsin-like β5-subunits of the proteasome due to the aromatic tyrosine residue at the scissile bond (i.e., P1 position).

From measurements of the rates of hydrolysis of the fluorogenic substrate by the proteasome in the presence of increasing concentrations of each inhibitor, second-order rate constants $k_{in}/K_i$ (M$^{-1}$ s$^{-1}$) were determined (Table 1), which reflect both the affinity of the non-covalent binding ($K_i$) and the rate of the chemical reaction with the enzyme ($k_{in}$). All of the syringolin analogues were capable in inhibiting the chymotrypsin-like activity of hs20S. Without wishing to be limited by any theory, consistent with the design predictions, the most significant contributor to the apparent second-order rate constants of the compounds was their binding affinity ($K_i$) rather than the rates of inhibition.

In vitro 20S peptidase inhibition assays were recorded in a 384-well plate at a SpectraMax M5 (Molecular Devices) plate-reader. Therefore, 5 nM human 20S (R&D) was incubated in buffer R (50 mM HEPEs-KOH, pH 7.5, 0.5 mM EDTA) with 100 μM of the fluorogenic peptide substrate Suc-LLVY-AMC. Reactions were started by adding various amounts of inhibitors 5 nM to 500 μM) to a final volume of 30 μL and peptide hydrolysis was continuously monitored for 90 minutes by changes in fluorescence (excitation 380 nm; emission 440 nm) at 37 degrees Celsius. The $k_{obs}$ values were determined by fitting the raw data to equation 1. The slopes of the plots of $k_{obs}$ versus I gave an apparent value of kob/I, also referred to as $k_{inact}/K_i$ for an irreversible inhibitor, which was then corrected by equation 2 to compensate for the effect of substrate competition, where app is the apparent value at different inhibitor concentrations.

$$P = v_s t + \frac{(v_0 - v_s)}{k_{obs}}[1 - e^{(-k_{obs}t)}] \quad \text{Equation 1}$$

$$k_{obs}/I = (k_{obs}/I)^{app}(1 + S/K_m) \quad \text{Equation 2}$$

Consistently, an analog of syringolin B with an isobutyl substituent at R, rather than the isopropyl substituent of the parent, exhibited a diminished capacity to inhibit the proteasome. In contrast, compounds with aromatic substituents (Table 1, compounds 3-13) at the same position were markedly more potent. Of these macrocyclic analogues, compounds 5 and 6, both containing fluorine-substituted benzyl groups, were the most effective in inhibiting the hs20S proteasome. A syringolin analogue with a methylindole substituent was only slightly more active than syringolin B. The enhanced inhibitory activities of syringolin B analogues having aromatic substituents at the R position on the macrolactam are consistent with the substrate preference of the β5 subunits of the proteasome and with the model for substrate mimicry.

A variety of aromatic groups, such as substituted benzyl rings, at variable R were evaluated, such as those substituted with fluoro groups. Compounds having a 3-fluorobenzyl substituent on the macrolactam (R$^1$) were more potent than those with a 2-fluorobenzyl substituent. (See, e.g., Compound 18 vs. Compound 26) Moreover, compound 33 with 3-fluorobenzyl substituent on the macrolactam (R$^1$) and a 3-trifluoromethyl benzyl substituent at R$^2$ demonstrated significant potency. This compound had a second-rate constant that was nearly four-times higher ($k_i/K_{in}$=15.862 M$^{-1}$s$^{-1}$) than the most potent compound described in Totaro, et al. Bioorg. Med. Chem, 2015 23:6218-6222 ($k_i/K_{in}$=4,305 M$^{-1}$s$^{-1}$).

TABLE 1

In Vitro Evaluation of Human Proteasome Inhibition by Syringolin Analogues

| Compound | R | R' | hs20S $k_{in}/K_i$ (M$^{-1}$s$^{-1}$) |
|---|---|---|---|
| 1 | | | 781 |
| 2 | | | 571 |

TABLE 1-continued
In Vitro Evaluation of Human Proteasome Inhibition by Syringolin Analogues
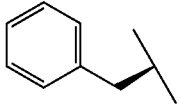
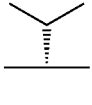
| Compound | R | R' | hs20S $k_{in}/K_i$ (M$^{-1}$s$^{-1}$) |
|---|---|---|---|
| 3 | 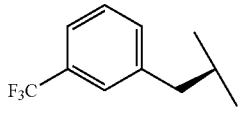 | 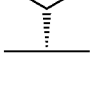 | 1,912 |
| 4 | 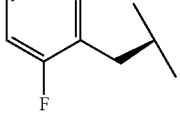 (3-F$_3$C) | 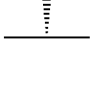 | 187 |
| 5 | 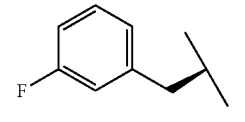 (2-F) | 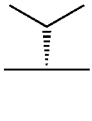 | 1,591 |
| 6 | 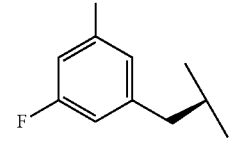 (3-F) | 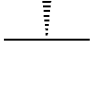 | 2,471 |
| 7 | 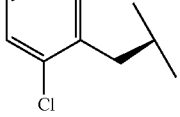 (3,5-F) | 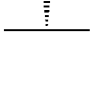 | 1,579 |
| 8 | 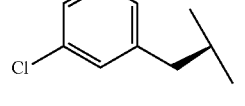 (2-Cl) | 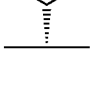 | 735 |
| 9 | 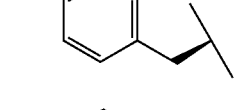 (3-Cl) | 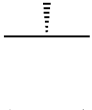 | 1,527 |
| 10 | 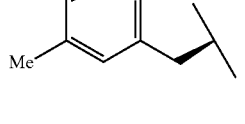 (4-Cl) |  | 1,214 |
| 11 | 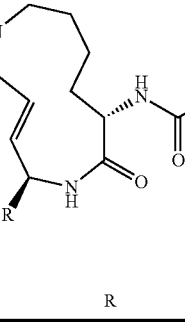 (3-Me) |  | 635 |
| 12 | 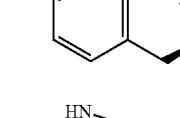 (4-Me) | 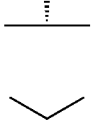 | 1,321 |
| 13 | 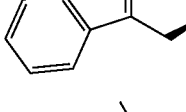 |  | 904 |
| 14 |  | 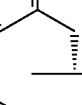 | 1,897 |
| 15 | 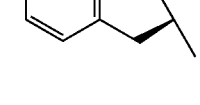 | 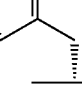 | 4,199 |
| 16 | 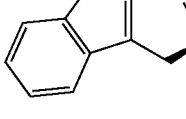 | 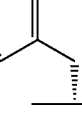 | 4,305 |
| 17 | | | 7271 |
| 18 | | | 4656 |
| 19 | | | 5877 |
| 20 | |  | 3797 |
| 21 | | | 7332 |
| 22 | | | 4444 |
| 23 | | | 2199 |
| 24 | | | 2749 |
| 25 | | | 8532 |
| 26 | | | 12605 |
| 27 | | | 14336 |
| 28 | | 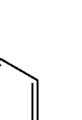 | 12866 |

TABLE 1-continued

In Vitro Evaluation of Human Proteasome Inhibition by Syringolin Analogues

| Compound | R | R' | hs20S $k_{in}/K_i$ $(M^{-1}s^{-1})$ |
|---|---|---|---|
| 29 | | | 11670 |
| 30 | | | 12202 |
| 31 | | | 5016 |
| 32 | | | 4531 |
| 33 | | | 15,862 |
| 34 | | benzyl | 4305 |

Figure 4:
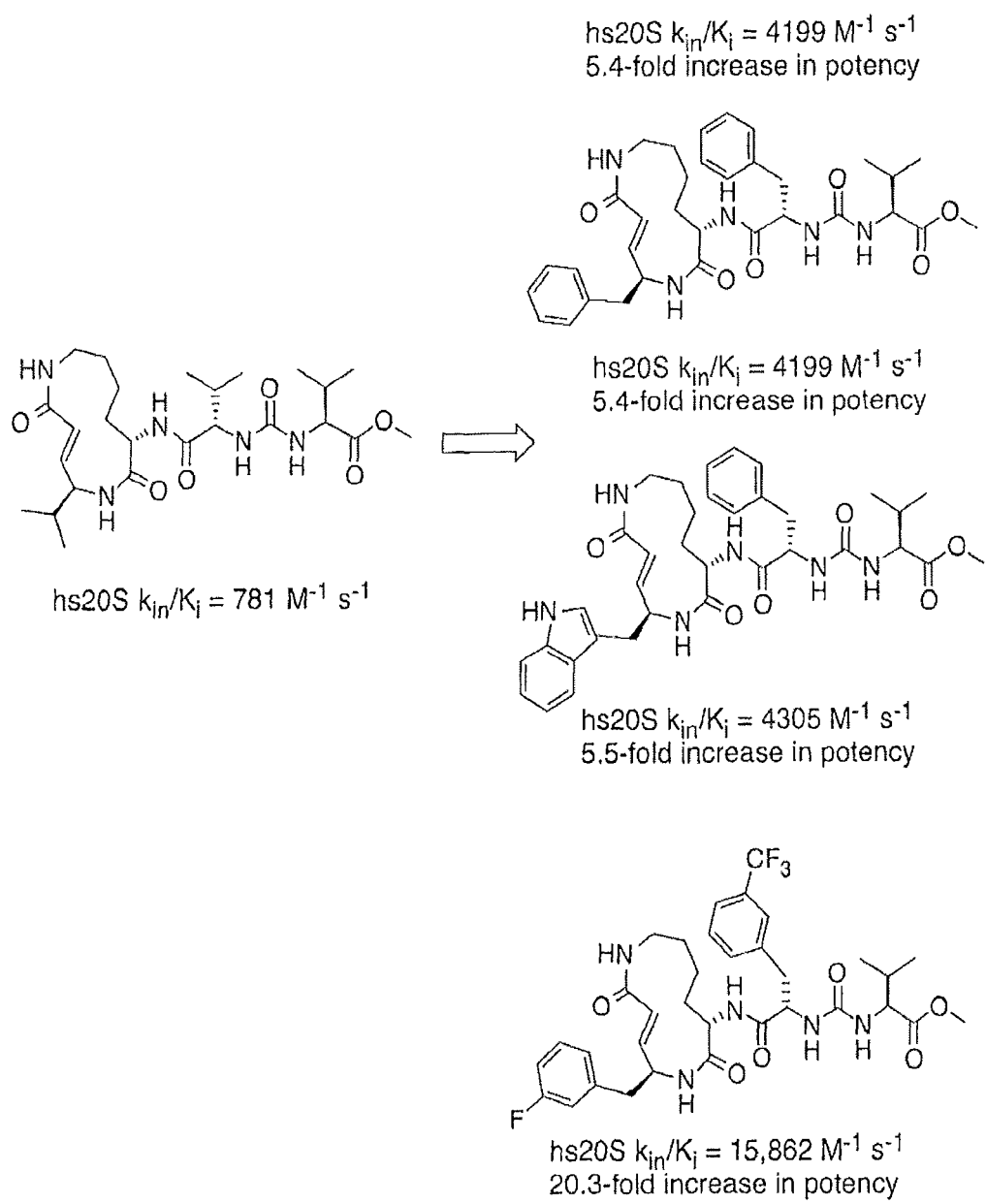
FIG. 4 is a non-limiting illustration of inhibitory activity of compound 1 in comparison to compound 15 (top right), compound 16 (middle right), and compound 34 (bottom right).

In a further structure-activity relationship study, the moiety of the syringolins that may correspond to the P3 residue of proteasome substrates was evaluated. FIG. 5 provides the initial data used to calculate the hs20S $k_{in}/K_i(M^{-1}s^{-1})$ rate constant. A molecule with the syringolin B macrolactam and a phenylalanine in the dipeptide urea had a second-order rate constant for inhibition 2.4-fold greater than the methyl ester of syringolin B (Table 1, compounds 1 and 14). The same compound reacted with hs20S at only 45% the rate of a molecule with syringolin analog with a benzyl group at the R position on the macrolactam and a phenylalanine in the dipeptide urea (Table 1, compounds 14 and 15). The most potent inhibitor had a methylindole substituent on the macrolactam and a phenylalanine residue in the dipeptide urea side chain (Table 1, FIG. 4, compound 16) because syringolins which macrolactam substituents were reminiscent of phenylalanine side chain were more potent (Table 1, compounds 3-12) than one with having the tryptophan side chain (13).

TABLE 2

Evaluation of Subunit-Specific Inhibition of Syringolin B Methyl Ester and Analogues Thereof

| Compound | Chymotrypsin-Like Activity $k_{in}/K_i$ $(M^{-1} s^{-1})$ | Trypsin-Like Activity $k_{in}/K_i$ $(M^{-1} s^{-1})$ |
|---|---|---|
| 1 | 781 | 326 |
| 16 | 4,305 | 1,701 |

The data in Table 1 illustrate inhibition of the β5-subunits of the proteasome, which have substrate specificities like chymotrypsin. Experiments were performed to assess whether the improvements in potency also translated to greater selectivity. Specifically, experiments were carried out to assess the capacities of syringolin B methyl ester (1) and the most potent inhibitor of the chymotrypsin-like activity (16) to inhibit the trypsin-like activity of the hs20S that is mediated by the β2 subunit. Using a fluorogenic peptide substrate (Boc-LRR-AMC), the second-order rate constants of proteasome inhibition by both compounds was measured. Compound 1 preferentially inhibited the chymotrypsin-like activity of the proteasome by 2.4-fold (Table 2). The degree of selectivity of compound 16 (2.5-fold greater in favor of the chymotrypsin-like activity) was similar to that of compound 1, which is a 5.5-fold greater inhibitor than the latter in assays of chymotrypsin-like activity (Table 1, FIG. 4).

Example 9: Biological Activity

Figure 6:
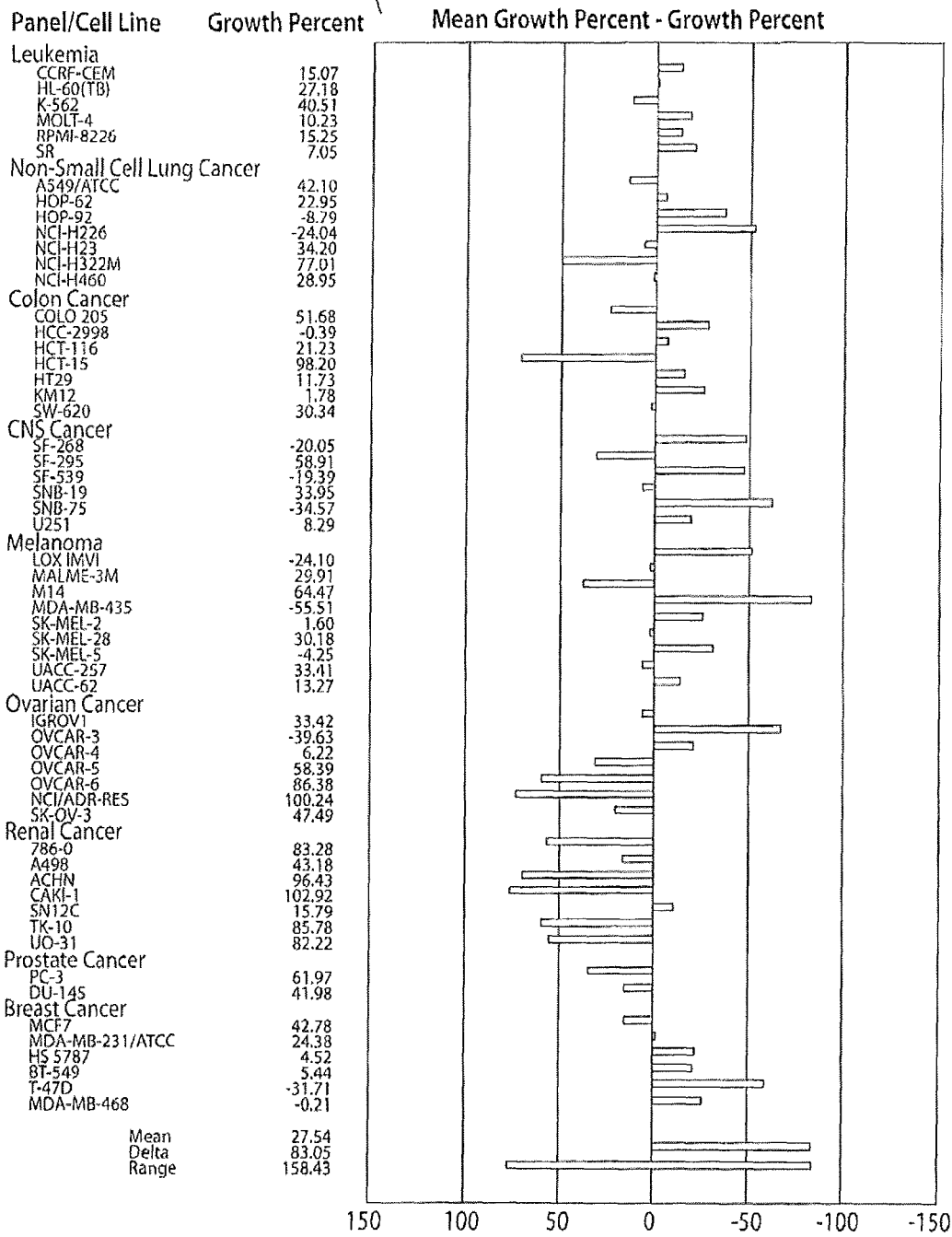
FIG. 6 is a graph illustrating in vitro inhibition results for 60 cancer cell lines from the National Cancer Institute (NCI) using compound 1.
Figure 7:
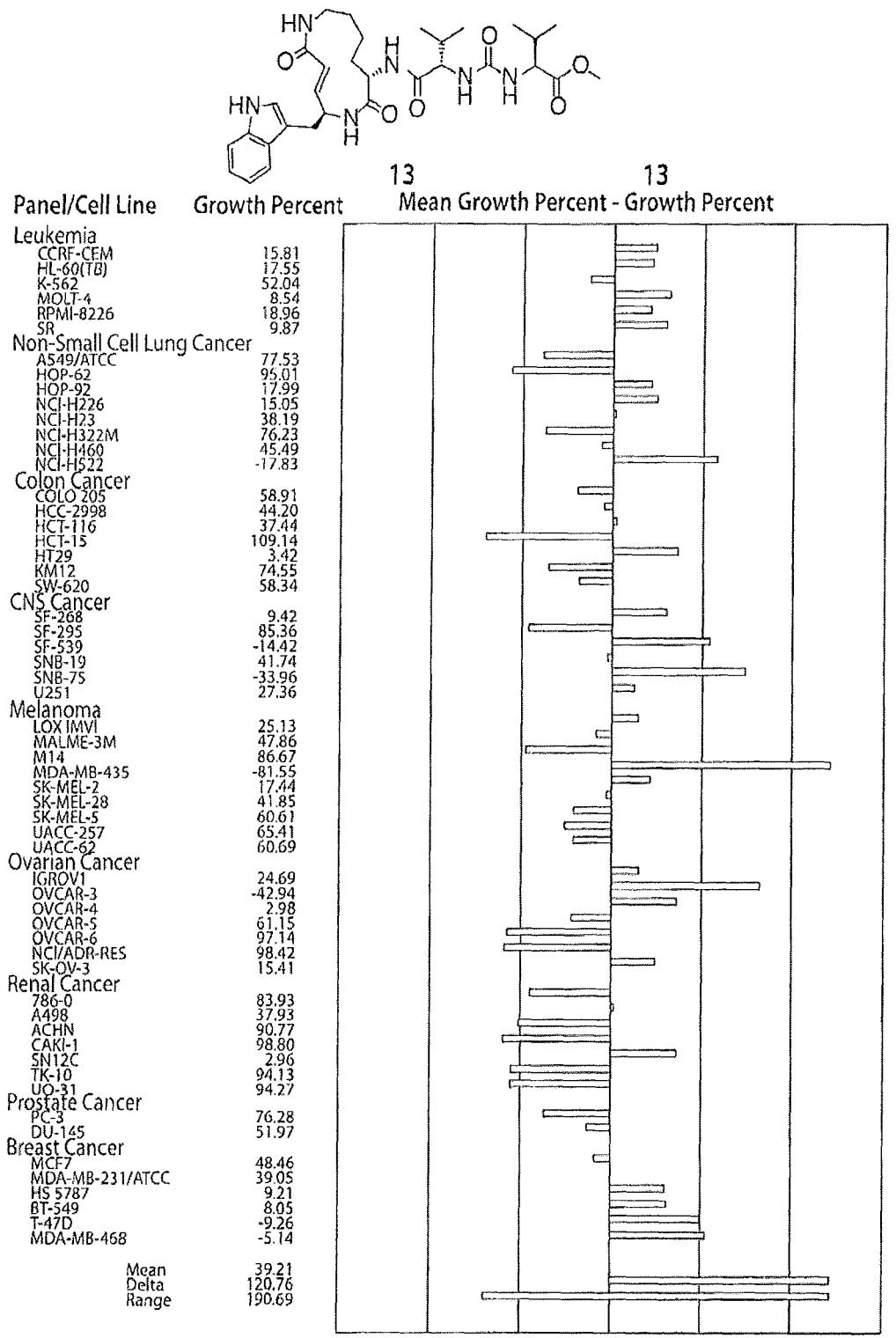
FIG. 7 is a graph illustrating in vitro inhibition results for 60 cancer cell lines from the NCI using compound 13.
Figure 8:
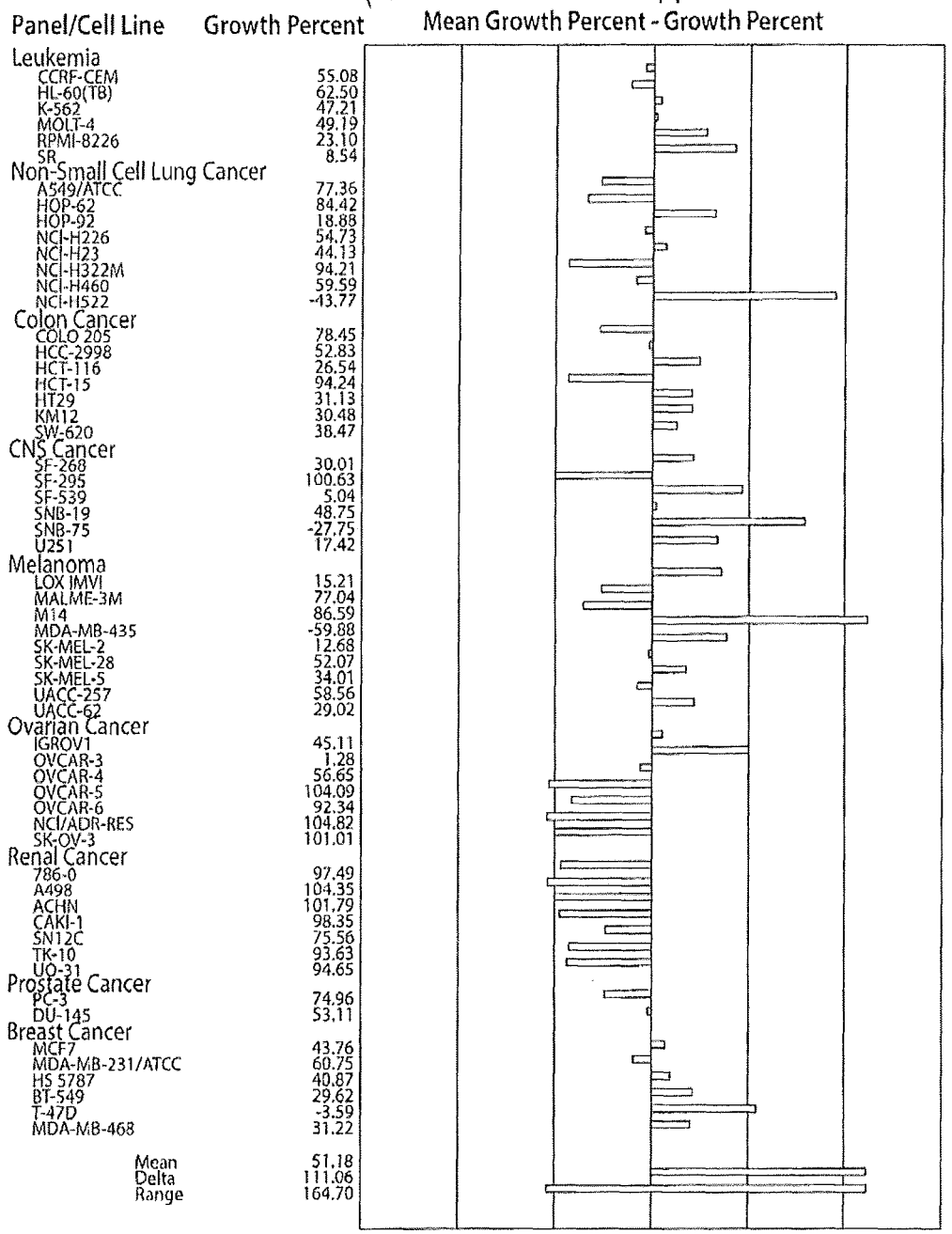
FIG. 8 is a graph illustrating in vitro inhibition results for 60 cancer cell lines from the NCI using compound 14.
Figure 9:
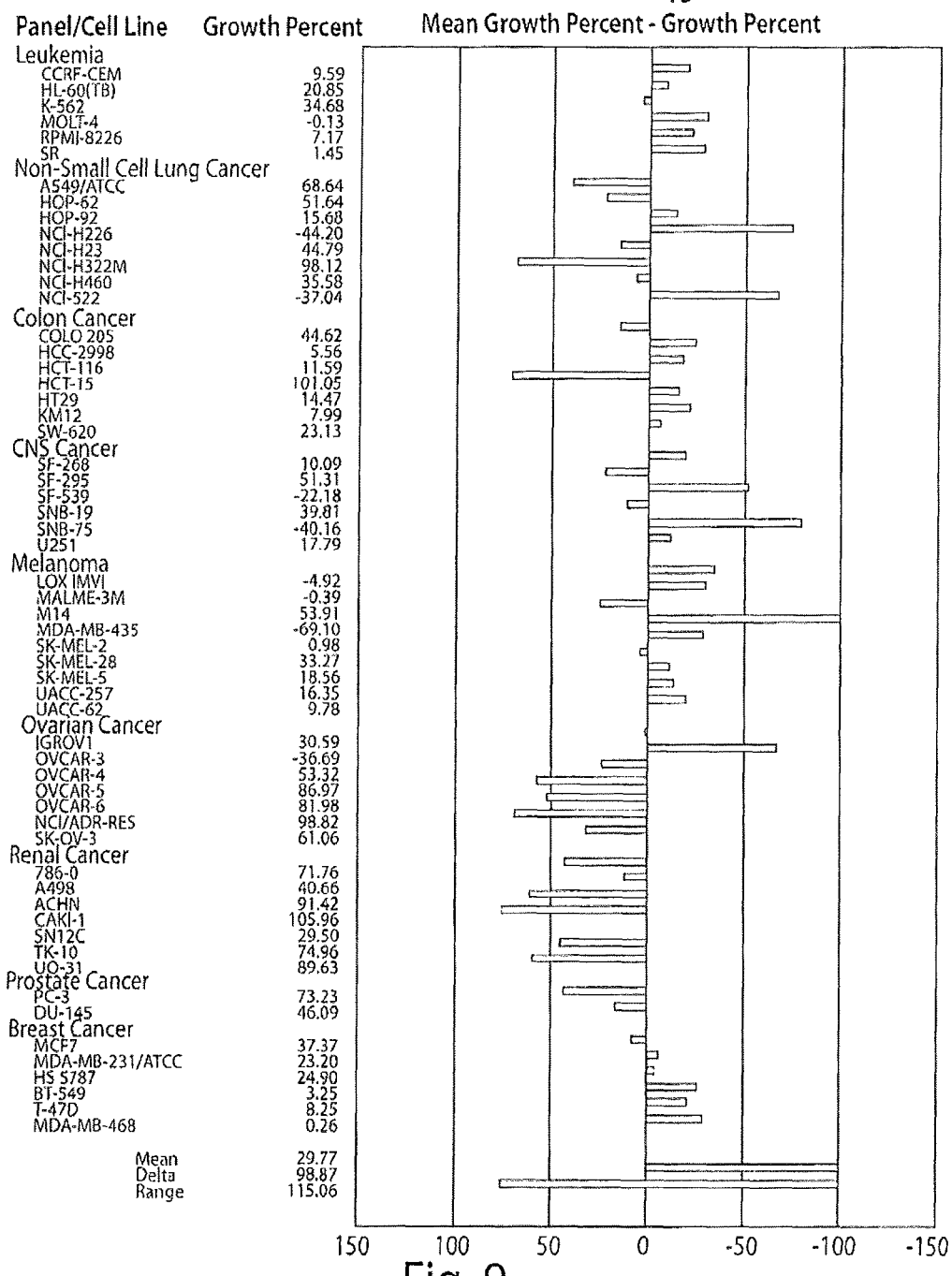
FIG. 9 is a graph illustrating in vitro inhibition results for 60 cancer cell lines from the NCI using compound 15.
Figure 10:
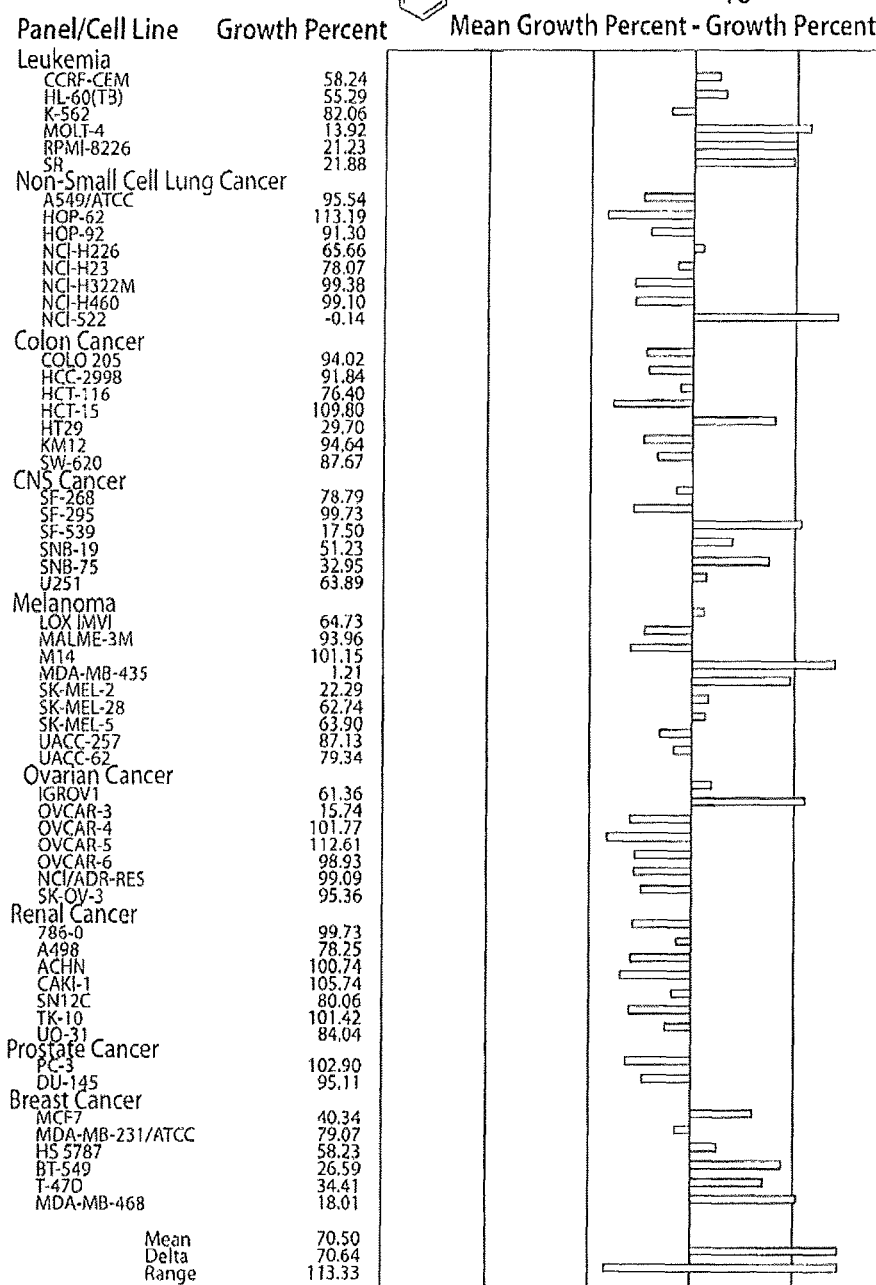
FIG. 10 is a graph illustrating in vitro inhibition results for 60 cancer cell lines from the NCI using compound 16.

To assess the growth inhibitory activities of the compounds of the invention against cancer cells, syringolin B methyl ester (1) and compounds 13, 14, 15, and 16 were submitted to the National Cancer Institute (NCI), where they were initially evaluated in single-dose assays at 10 μM with 60 different cancer cell lines. FIG. 6 illustrates the in vitro inhibition results for compound 1, while FIG. 7 illustrates the in vitro inhibition results for compound 13. FIG. 8 illustrates the in vitro inhibition results for compound 14, while FIG. 9 illustrates the in vitro inhibition results for compound 15. FIG. 10 illustrates the in vitro inhibition results for compound 16.

Compound 15 exhibited the broadest spectrum of growth inhibitory activity against the panel of cell lines. Specifically, cell lines incubated in media with 10 μM of compound 15 grew at an average of 30% of those incubated in media without compound. The mean growth of the cell lines in media with the same concentration of compound 16 was approximately 71% of those in negative control experiments.

Figure 11A:
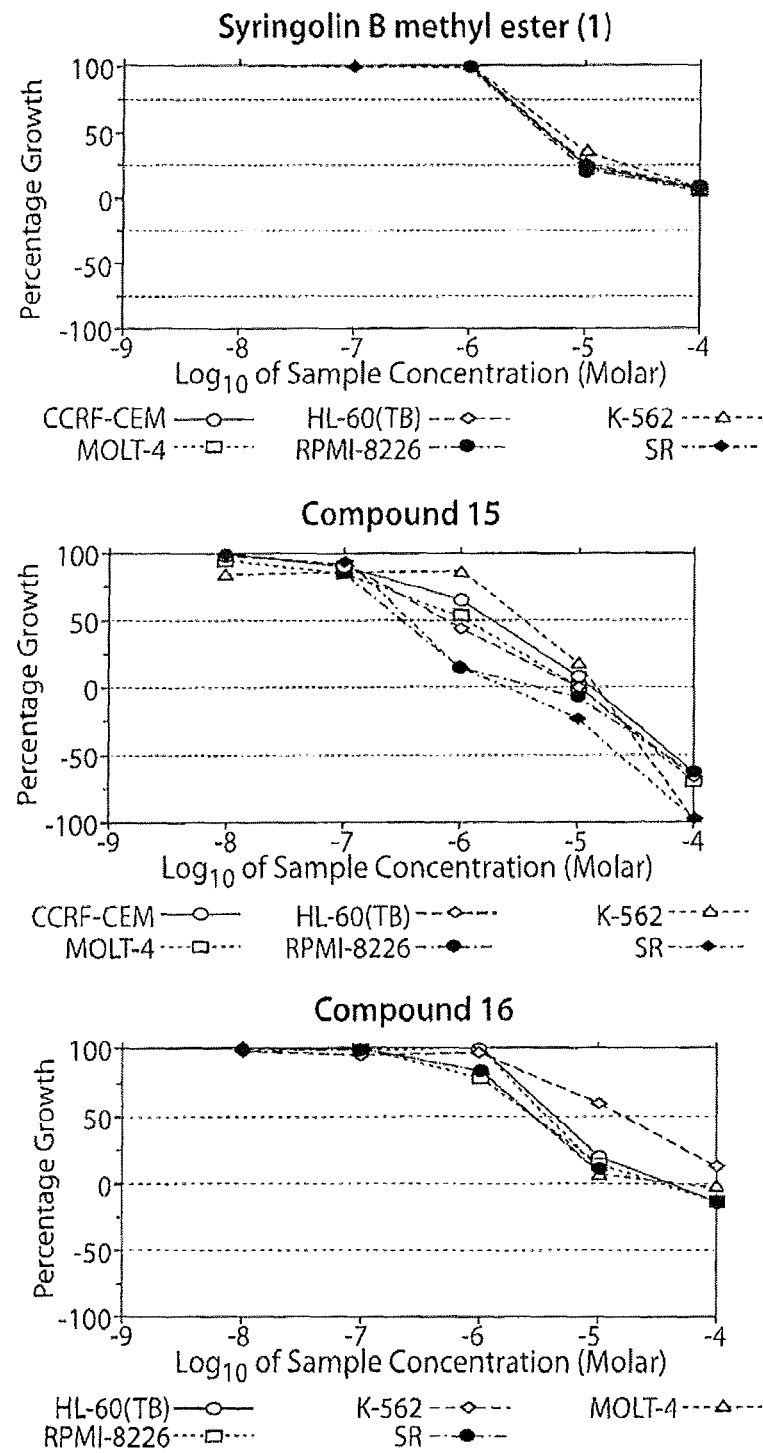
Figure 11B:
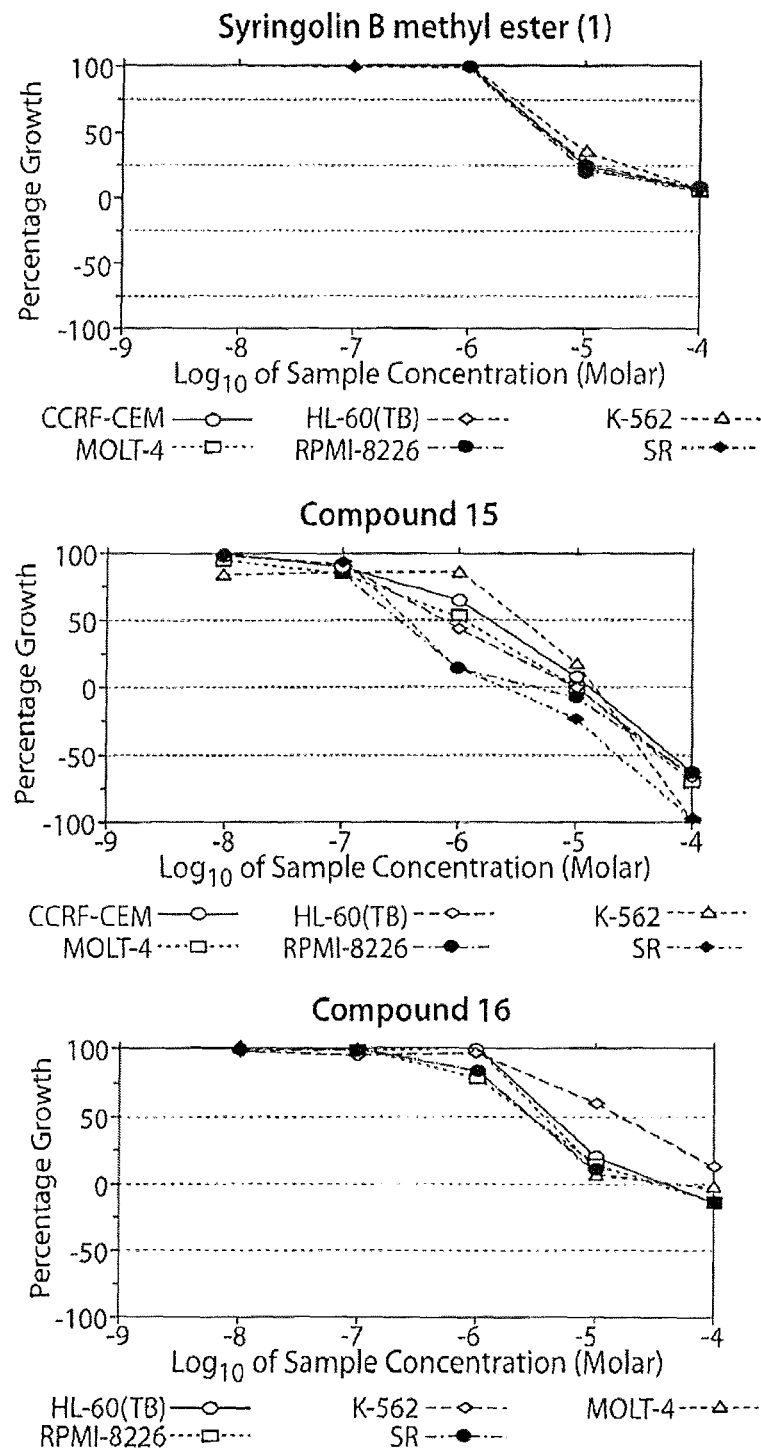

As a follow up to the single-dose experiments, the dose-dependent growth inhibition by syringolin B methyl ester (1) (FIG. 11A) and the most potent inhibitors (15 and 16) (FIG. 1B) was assessed at the NCI. The three compounds were particularly active against leukemia cell lines. Compound 16 is slightly more potent than compound 15 as a proteasome inhibitor (Table 3), and is more potent in cell culture. Without wishing to be limited by any theory, such differences in biochemical and biological patterns may be explained by differences in the cell permeabilities or stabilities of the two compounds. Compound 16 was as much as 11.5-fold more potent than syringolin B methyl ester (1) against the leukemia cell lines.

TABLE 3

Growth Inhibitory Activities of Syringolin B Methyl Ester and Analogs Thereof Against Various Leukemia Cell Lines

| | GI$_{50}$ (μM) | | |
|---|---|---|---|
| Cell Line | Compound 1 | Compound 15 | Compound 16 |
| HL-60 | 5.41 | 4.34 | 1.29 |
| K-562 | 6.12 | 14.6 | 2.94 |
| MOLT-4 | 4.73 | 3.32 | 0.599 |
| RPMI-8226 | 3.97 | 2.72 | 0.343 |
| SR | 5.13 | 2.78 | 0.453 |

Data provided by the National Cancer Institute (NCI): GI$_{50}$ is the concentration of test drug where 100×(T−T0)/(C−T0)=50. The optical density of the test well after a 48-h period of exposure to test drug is T, the optical density at time zero is T0, and the control optical density is C. The "50" is called the GI50PRCNT, a T/C-like parameter that can have values from +100 to −100.

The experiments reported herein shed light on the structure-activity relationships of the syringolins and show that proteasome inhibitors can be rationally optimized based on knowledge of the substrate preferences of the proteolytic subunits of the proteasome. As demonstrated herein, syringolin analogues that are reminiscent of chymotrypsin substrates are more potent inhibitors of the β5-subunits of the proteasome than the parent compound, with comparable subunit inhibition selectivities. Without wishing to be limited by any theory, improvement in potency, and not selectivity, can be beneficial in view of the fact that inhibition of multiple proteolytic subunits by a compound is highly correlated with significant suppression of protein degradation. As demonstrated herein, syringolin analogues are potent suppressors of the growth of cancer lines in vitro, especially those derived from leukemias. The present studies demonstrate that syringolin analogues are potent antiproliferation agents, and in certain embodiments are potent anti-leukemic drugs.

The disclosures of each and every patent, patent application, and publication cited herein are hereby incorporated herein by reference in their entireties.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I), or a salt, racemic mixture, enantiomer, pro-drug, or diastereoisomer thereof:

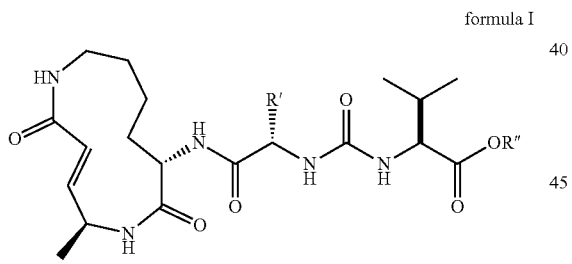

formula I wherein:
R is arylalkyl, or heteroarylalkyl, wherein each one of the arylalkyl or heteroarylalkyl groups is independently optionally substituted with one or more of $C_1$-$C_6$ alkyl, haloalkyl, F, Cl, Br, I, $C_1$-$C_6$ alkoxy, or hydroxy;
R' is $C_1$-$C_6$ alkyl or arylalkyl, wherein each one of the alkyl or arylakyl groups is independently optionally substituted with one or more of $C_1$-$C_6$ alkyl, haloalkyl, F, Cl, Br, I, $C_1$-$C_6$ alkoxy, or hydroxy; and
R" is H or $C_1$-$C_{16}$ alkyl, wherein each one of the alkyl groups is independently optionally substituted with one or more of $C_1$-$C_6$ alkyl, F, Cl, Br, I, $C_1$-$C_6$ alkoxy, or hydroxy.

2. The compound of claim 1, wherein R is aryl($CH_2$)—, or heteroaryl($CH_2$)—, wherein each one of the aryl($CH_2$)— or heteroaryl($CH_2$)— groups is independently optionally substituted with one or more of $C_1$-$C_6$ alkyl, haloalkyl, F, Cl, Br, I, $C_1$-$C_6$ alkoxy, or hydroxy.

3. The compound of claim 1, wherein R is benzyl or 3-indolmethyl, wherein each one of the benzyl or 3-indolmethyl groups is independently optionally substituted with one or more of $C_1$-$C_6$ alkyl, haloalkyl, F, Cl, Br, I, $C_1$-$C_6$ alkoxy, or hydroxy.

4. The compound of claim 3, wherein the substituted benzyl is 2-trifluoromethylbenzyl, 3-trifluoromethylbenzyl, 4-trifluoromethylbenzyl, 2-fluorobenzyl, 3-fluorobenzyl, 4-fluorobenzyl, 2-chlorobenzyl, 3-chlorobenzyl, 4-chlorobenzyl, 2-methylbenzyl, 3-methylbenzyl, 4-methylbenzyl, 2,4-difluorobenzyl, 3,5-difluorobenzyl, 2,4-dichlorobenzyl, or 2,4-dimethylbenzyl.

5. The compound of claim 1, wherein R' is isopropyl and R is:

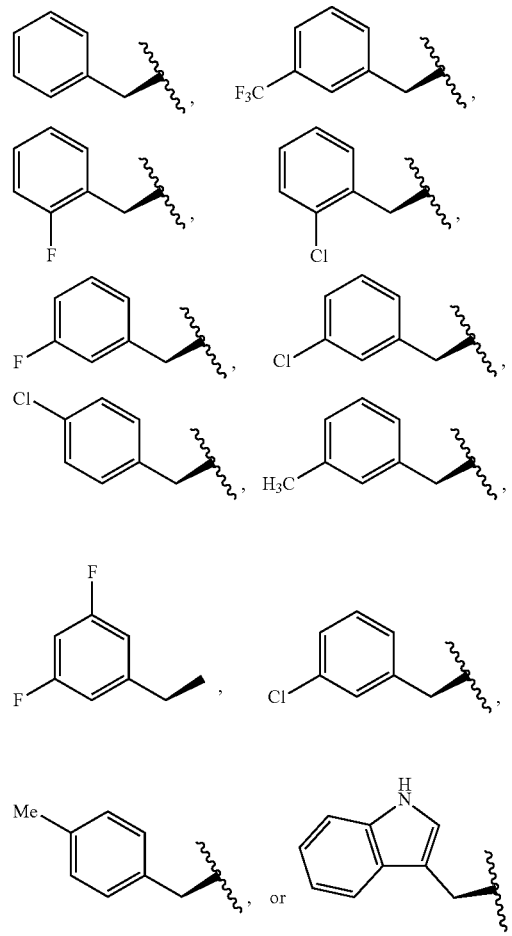

6. The compound of claim 1, wherein R' is benzyl or substituted benzyl and wherein R is:

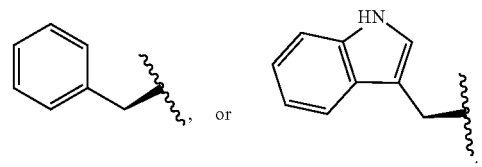

7. The compound of claim 1, wherein R is:

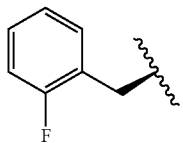

and R' is selected from

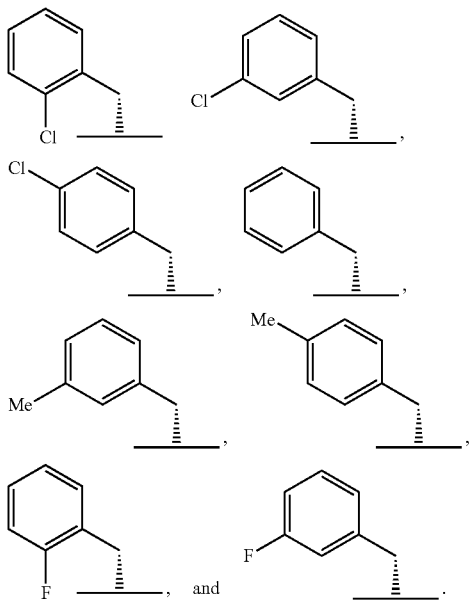

8. The compound of claim 1, wherein R is

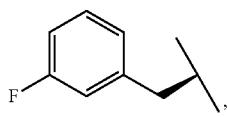

and R' is selected from

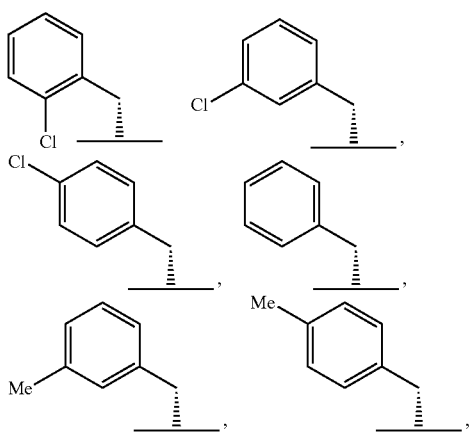

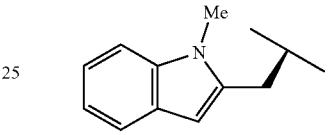

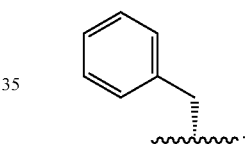

9. The compound of claim 1, wherein R is and R' is

10. The compound of claim 1, wherein R″ is H, methyl, ethyl, propyl, isopropyl or dodecyl.

11. The compound of claim 1, wherein the salt is an acid addition salt selected from the group consisting of sulfate, hydrogen sulfate, hydrochloric, hydrobromic, hydriodic, nitric, carbonic, sulfuric, phosphoric, formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid, or combinations thereof.

12. The compound of claim 1, wherein the salt is a base addition salt selected from the group consisting of calcium, magnesium, potassium, sodium, ammonium, zinc, a basic amine salt, and any combinations thereof, wherein the basic amine is selected from the group consisting of triethylamine, diisopropylethylamine, trimethylamine, N,N'-dibenzylethylene-diamine, chloroprocaine, choline, diethanolamine, ethylenediamine, meglumine and procaine, or combinations thereof.

13. The compound of claim 1, wherein the compound is (S)-methyl 2-(3-((S)-1-(((5S,8S,E)-5-benzyl-2,7-dioxo-1,6-diazacyclododec-3-en-8-yl)amino)-3-methyl-1-oxobutan-2-yl)ureido)-3-methylbutanoate (3):

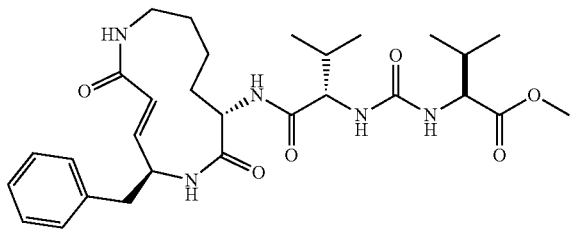 [SMILES: COC(=O)[C@@H](NC(=O)N[C@H](C(=O)N[C@H]1CCCCNC(=O)/C=C/[C@H](Cc2ccccc2)NC1=O)C(C)C)C(C)C]

(S)-methyl 2-(3-((S)-1-(((5S,8S,E)-2,7-dioxo-5-(3-(trifluoromethyl)benzyl)-1,6-diaza cyclododec-3-en-yl)amino)-3-methyl-1-oxobutan-2-yl)ureido)-3-methylbutanoate (4):

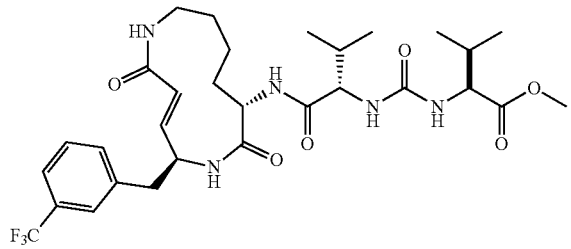 [SMILES: COC(=O)[C@@H](NC(=O)N[C@H](C(=O)N[C@H]1CCCCNC(=O)/C=C/[C@H](Cc2cccc(C(F)(F)F)c2)NC1=O)C(C)C)C(C)C]

(S)-methyl 2-(3-((S)-1-(((5S,8S,E)-5-(2-fluorobenzyl)-2,7-dioxo-1,6-diazacyclododec-3-en-8-yl)amino)-3-methyl-1-oxobutan-2-yl)ureido)-3-methylbutanoate (5):

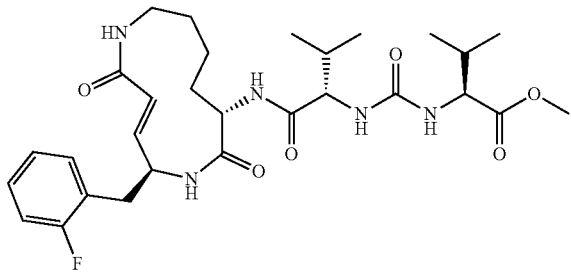 [SMILES: COC(=O)[C@@H](NC(=O)N[C@H](C(=O)N[C@H]1CCCCNC(=O)/C=C/[C@H](Cc2ccccc2F)NC1=O)C(C)C)C(C)C]

(S)-methyl 2-(3-((S)-1-(((5S,8S, E)-5-(3-fluorobenzyl)-2,7-dioxo-1,6-diazacyclododec-3-en-8-yl)amino)-3-methyl-1-oxobutan-2-yl)ureido)-3-methylbutanoate (6):

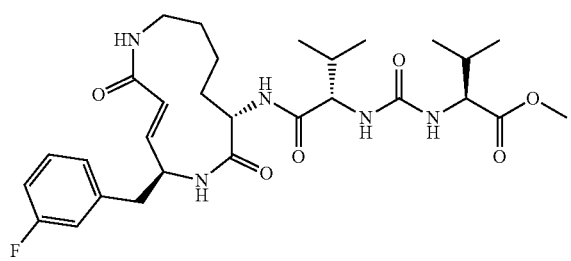 [SMILES: COC(=O)[C@@H](NC(=O)N[C@H](C(=O)N[C@H]1CCCCNC(=O)/C=C/[C@H](Cc2cccc(F)c2)NC1=O)C(C)C)C(C)C]

(S)-methyl 2-(3-((S)-1-(((5S,8S, E)-5-(3,5-difluorobenzyl)-2,7-dioxo-1,6-diazacyclododec-3-en-8-yl)amino)-3-methyl-1-oxobutan-2-yl)ureido)-3-methylbutanoate (7):

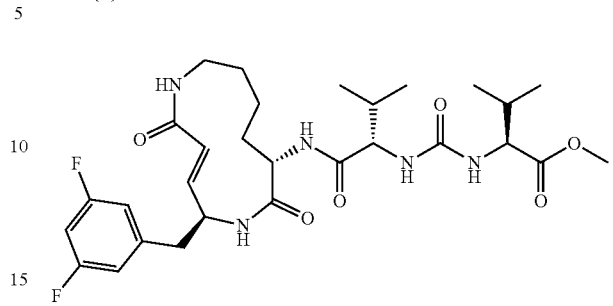

(S)-methyl 2-(3-((S)-1-(((5S,8S,E)-5-(2-chlorobenzyl)-2,7-dioxo-1,6-diazacyclododec-3-en-8-yl)amino)-3-methyl-1-oxobutan-2-yl)ureido)-3-methylbutanoate (8):

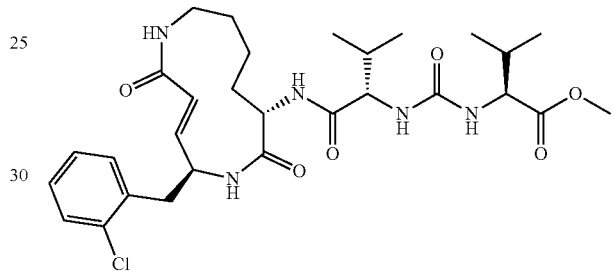

(S)-methyl 2-(3-((S)-1-(((5S,8S, E)-5-(2-chlorobenzyl)-2,7-dioxo-1,6-diazacyclododec-3-en-8-yl)amino)-3-methyl-1-oxobutan-2-yl)ureido)-3-methylbutanoate (9):

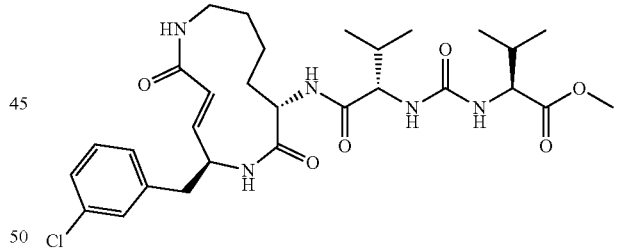

(S)-methyl 2-(3-((S)-1-(((5S,8S,E)-5-(4-chlorobenzyl)-2,7-dioxo-1,6-diazacyclododec-3-en-8-yl)amino)-3-methyl-1-oxobutan-2-yl)ureido)-3-methylbutanoate (10):

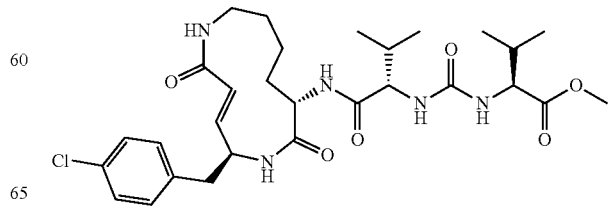

(S)-methyl 3-methyl-2-(3-((S)-3-methyl-1-(((5S,8S,E)-5-(3-methylbenzyl)-2,7-dioxo-1,6-diazacyclododec-3-en-8-yl)amino)-1-oxobutan-2-yl)ureido)butanoate (11):

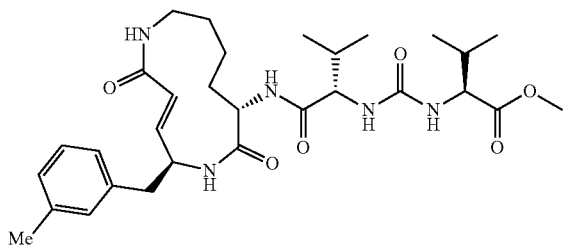 [SMILES: COC(=O)[C@@H](NC(=O)N[C@H](C(=O)N[C@H]1CCCCNC(=O)/C=C/[C@H](Cc2cccc(C)c2)NC1=O)C(C)C)C(C)C]

(S)-methyl 3-methyl-2-(3-((S)-3-methyl-1-(((5S,8S,E)-5-(4-methylbenzyl)-2,7-dioxo-1,6-diazacyclododec-3-en-8-yl)amino)-1-oxobutan-2-yl)ureido)butanoate (12):

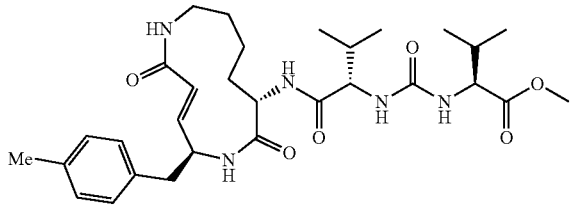 [SMILES: COC(=O)[C@@H](NC(=O)N[C@H](C(=O)N[C@H]1CCCCNC(=O)/C=C/[C@H](Cc2ccc(C)cc2)NC1=O)C(C)C)C(C)C]

(S)-methyl 2-(3-((S)-1-(((5S,8S,E)-5-(1H-indol-3-yl)methyl)-2,7-dioxo-1,6-diazacyclododec-3-en-8-yl)amino)-3-methyl-1-oxobutan-2-yl)ureido)-3-methylbutanoate (13):

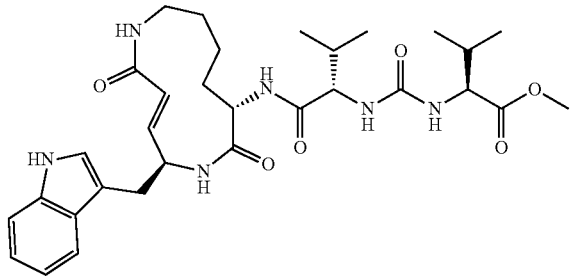 [SMILES: COC(=O)[C@@H](NC(=O)N[C@H](C(=O)N[C@H]1CCCCNC(=O)/C=C/[C@H](Cc2c[nH]c3ccccc23)NC1=O)C(C)C)C(C)C]

(S)-methyl 2-(3-((S)-1-(((5S,8S,E)-5-benzyl-2,7-dioxo-1,6-diazacyclododec-3-en-8-yl)amino)-1-oxo-3-phenylpropan-2-yl)ureido)-3-methylbutanoate (15):

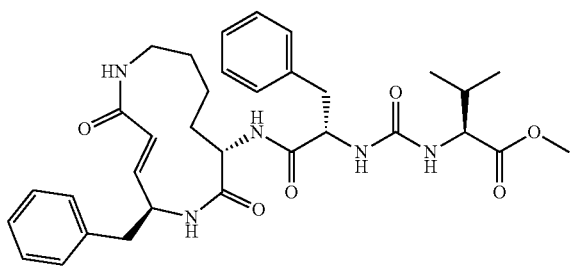 [SMILES: COC(=O)[C@@H](NC(=O)N[C@@H](Cc1ccccc1)C(=O)N[C@H]1CCCCNC(=O)/C=C/[C@H](Cc2ccccc2)NC1=O)C(C)C]

(S)-methyl 2-(3-(2-(((5S,8S,E)-5-((1H-indol-3-yl)methyl)-2,7-dioxo-1,6-diazacyclododec-3-en-8-yl)amino)-2-oxoethyl)ureido)-3-methylbutanoate (16):

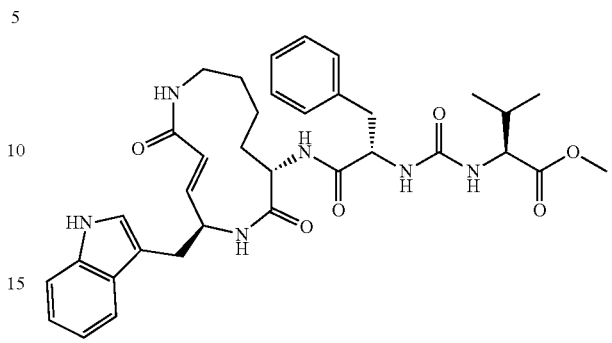

(S)-methyl 2-(3-((S)-3-(2-chlorophenyl)-1-(((5S,8S, E)-5-(2-fluorobenzyl)-2,7-dioxo-1,6-diazacyclododec-3-en-8-ylamino)-1-oxopropan-2-yl)ureido)-3-methylbutanoate (17)

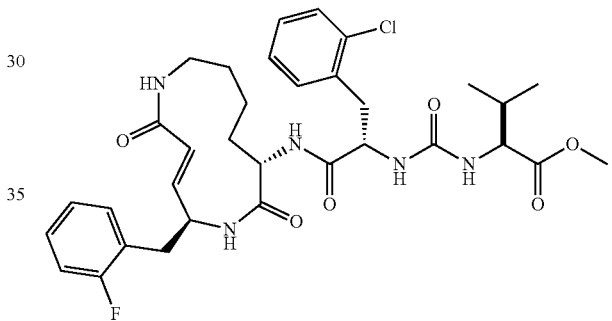

(S)-methyl 2-(3-((S)-3-(3-chlorophenyl)-1-((5S,8S,E)-5-(2-fluorobenzyl)-2,7-dioxo-1,6-diazacyclododec-3-en-8-ylamino)-1-oxopropan-2-yl)ureido)-3-methylbutanoate (18)

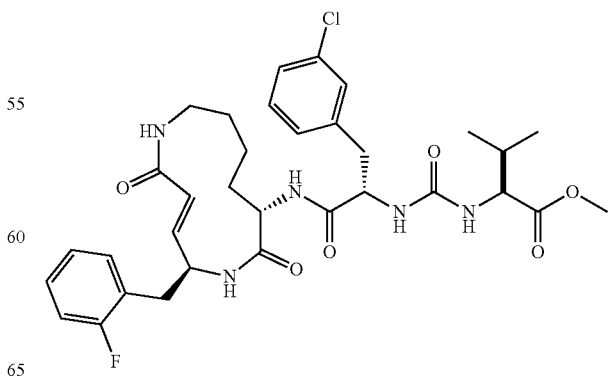

(S)-methyl 2-(3-((S)-1-((5S,8S,E)-5-(2-fluorobenzyl)-2,
7-dioxo-1,6-diazacyclododec-3-en-8-ylamino)-1-oxo-
3-phenylpropan-2-yl)ureido)-3-methylbutanoate (19)

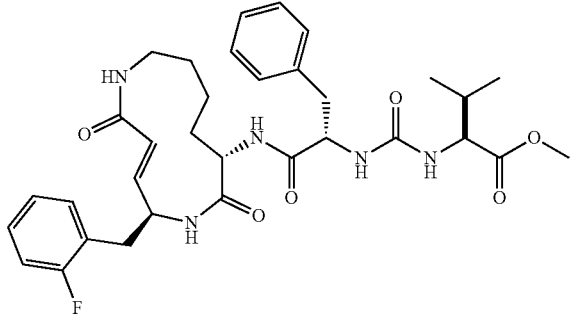 [SMILES: COC(=O)[C@@H](NC(=O)N[C@@H](Cc1ccccc1)C(=O)N[C@H]1CCCCNC(=O)/C=C/[C@H](Cc2ccccc2F)NC1=O)C(C)C]

(S)-methyl 2-(3-((S)-1-((5S,8S,E)-5-(2-fluorobenzyl)-2,
7-dioxo-1,6-diazacyclododec-3-en-8-ylamino)-1-oxo-
3-m-tolylpropan-2-yl)ureido)-3-methylbutanoate (20)

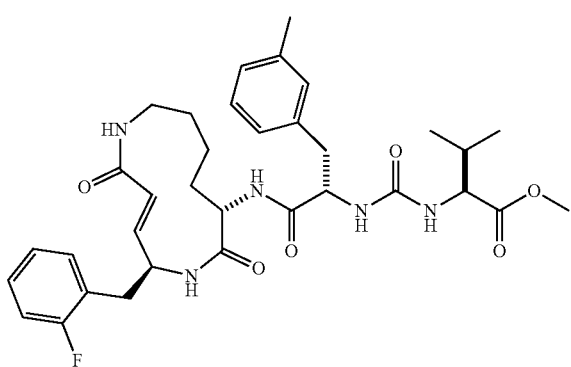 [SMILES: COC(=O)[C@@H](NC(=O)N[C@@H](Cc1cccc(C)c1)C(=O)N[C@H]1CCCCNC(=O)/C=C/[C@H](Cc2ccccc2F)NC1=O)C(C)C]

(S)-methyl 2-(3-((S)-1-((5S,8S,E)-5-(2-fluorobenzyl)-2,
7-dioxo-1,6-diazacyclododec-3-en-8-ylamino)-1-oxo-
3-p-tolylpropan-2-yl)ureido)-3-methylbutanoate (21)

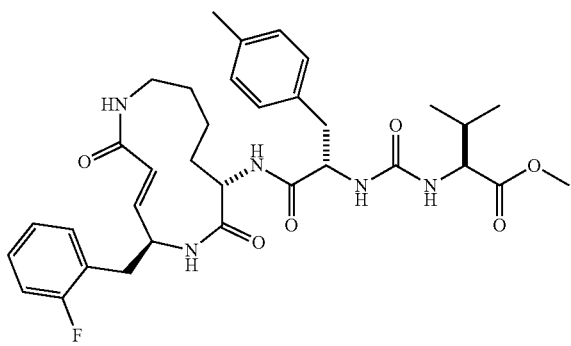 [SMILES: COC(=O)[C@@H](NC(=O)N[C@@H](Cc1ccc(C)cc1)C(=O)N[C@H]1CCCCNC(=O)/C=C/[C@H](Cc2ccccc2F)NC1=O)C(C)C]

(S)-methyl 2-(3-((S)-1-((5S,8S,E)-5-(2-fluorobenzyl)-2,
7-dioxo-1,6-diazacyclododec-3-en-8-ylamino)-1-oxo-3-(2-
fluorophenyl)-1-oxopropan-2-yl)ureido)-3-methylbu-
tanoate (22)

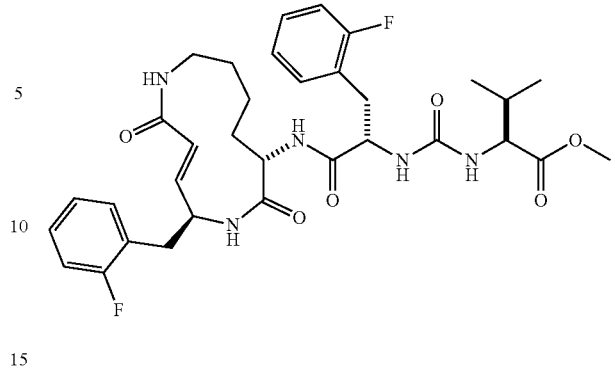

(S)-methyl 2-(3-((S)-1-((5S,8S, E)-5-(2-fluorobenzyl)-2,
7-dioxo-1,6-diazacyclododec-3-en-8-ylamino)-3-(3-
fluorophenyl)-1-oxopropan-2-yl)ureido)-3-methylbu-
tanoate (23)

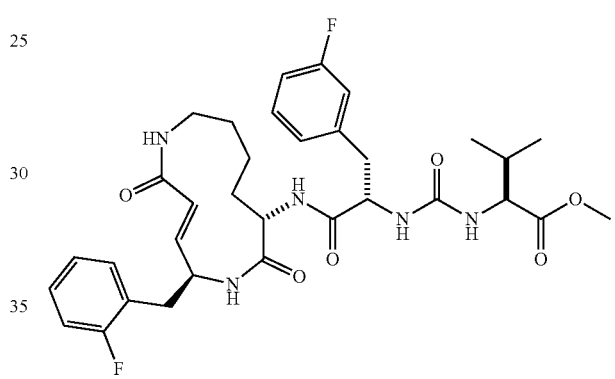

(S)-methyl 2-(3-((S)-3-(2-chlorophenyl)-1-((5S,8S, E)-5-
(3-fluorobenzyl)-2,7-dioxo-1,6-diazacyclododec-3-en-
8-ylamino)-1-oxopropan-2-yl)ureido)-3-methylbu-
tanoate (24)

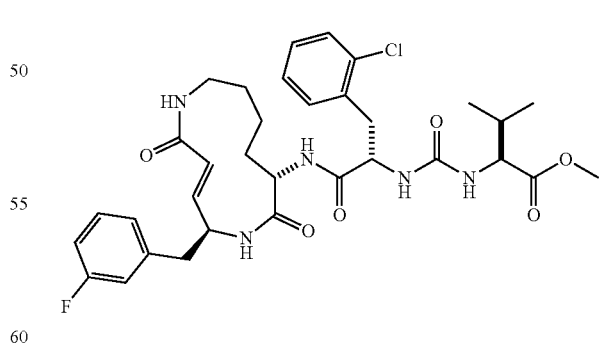

(S)-methyl 2-(3-((S)-3-(3-chlorophenyl)-1-((5S,8S,E)-5-
(3-fluorobenzyl)-2,7-dioxo-1,6-diazacyclododec-3-en-
8-ylamino)-1-oxopropan-2-yl)ureido)-3-methylbu-
tanoate (25)

81

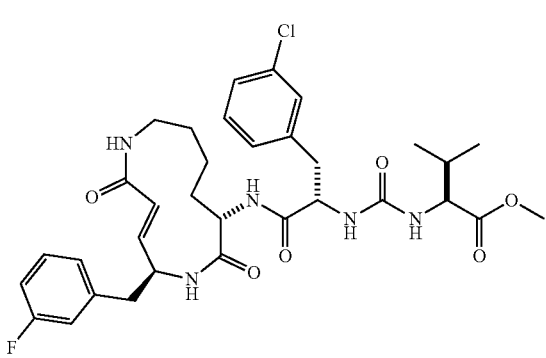 [SMILES: COC(=O)[C@@H](NC(=O)N[C@@H](Cc1cccc(Cl)c1)C(=O)N[C@H]1CCCCNC(=O)/C=C/[C@H](Cc2cccc(F)c2)NC1=O)C(C)C]

(S)-methyl 2-(3-((S)-3-(4-chlorophenyl)-1-((5S,8S,E)-5-(3-fluorobenzyl)-2,7-dioxo-1,6-diazacyclododec-3-en-8-ylamino)-1-oxopropan-2-yl)ureido)-3-methylbutanoate (26)

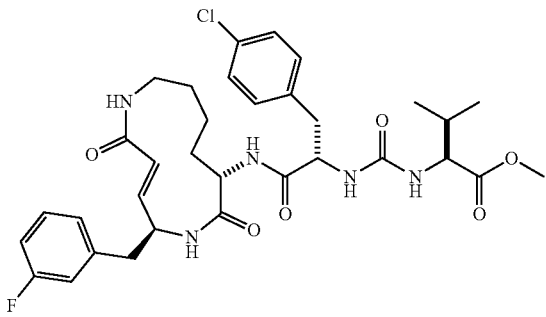 [SMILES: COC(=O)[C@@H](NC(=O)N[C@@H](Cc1ccc(Cl)cc1)C(=O)N[C@H]1CCCCNC(=O)/C=C/[C@H](Cc2cccc(F)c2)NC1=O)C(C)C]

(S)-methyl 2-(3-((S)-1-((5S,8S,E)-5-(3-fluorobenzyl)-2,7-dioxo-1,6-diazacyclododec-3-en-8-ylamino)-1-oxo-3-phenylpropan-2-yl)ureido)-3-methylbutanoate (27)

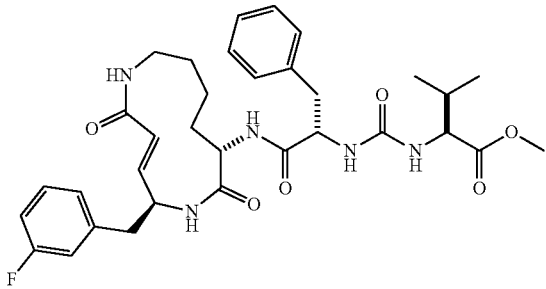

(S)-methyl 2-(3-((S)-1-((5S,8S,E)-5-(3-fluorobenzyl)-2,7-dioxo-1,6-diazacyclododec-3-en-8-ylamino)-1-oxo-3-m-tolylpropan-2-yl)ureido)-3-methylbutanoate (28)

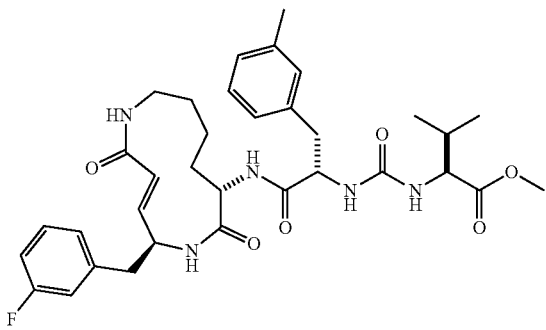 [SMILES: COC(=O)[C@@H](NC(=O)N[C@@H](Cc1cccc(C)c1)C(=O)N[C@H]1CCCCNC(=O)/C=C/[C@H](Cc2cccc(F)c2)NC1=O)C(C)C]

82

(S)-methyl 2-(3-((S)-1-((5S,8S,E)-5-(3-fluorobenzyl)-2,7-dioxo-1,6-diazacyclododec-3-en-8-ylamino)-1-oxo-3-p-tolylpropan-2-yl)ureido)-3-methylbutanoate (29)

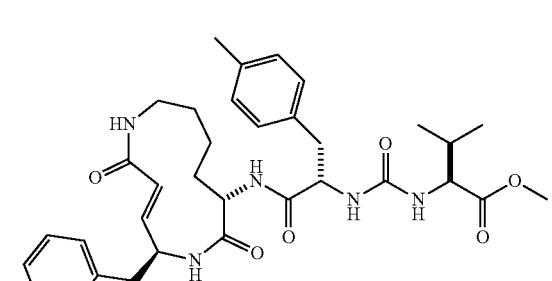

(S)-methyl 2-(3-((S)-1-((5S,8S,E)-5-(3-fluorobenzyl)-2,7-dioxo-1,6-diazacyclododec-3-en-8-ylamino)-3-(2-fluorophenyl)-1-oxopropan-2-yl)ureido)-3-methylbutanoate (30)

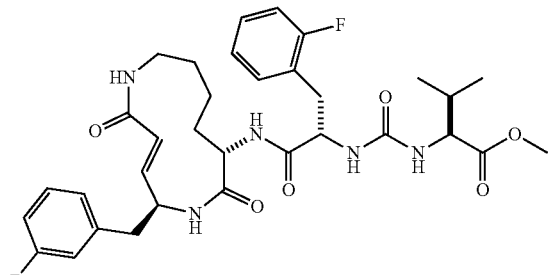

(S)-methyl 2-(3-((S)-1-((5S,8S,E)-5-(3-fluorobenzyl)-2,7-dioxo-1,6-diazacyclododec-3-en-8-ylamino)-3-(3-fluorophenyl)-1-oxopropan-2-yl)ureido)-3-methylbutanoate (31)

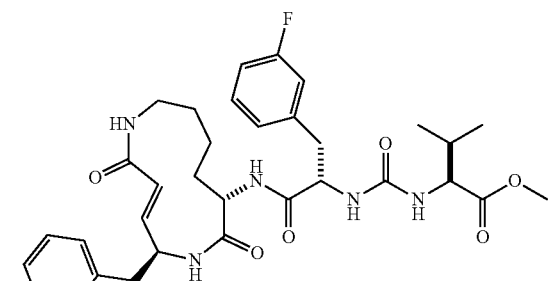

(S)-methyl 2-(3-((S)-1-((5S,8S,E)-5-(3-fluorobenzyl)-2,7-dioxo-1,6-diazacyclododec-3-en-8-ylamino)-1-oxo-3-(3-(trifluoromethyl)phenyl)propan-2-yl)ureido)-3-methylbutanoate (32)

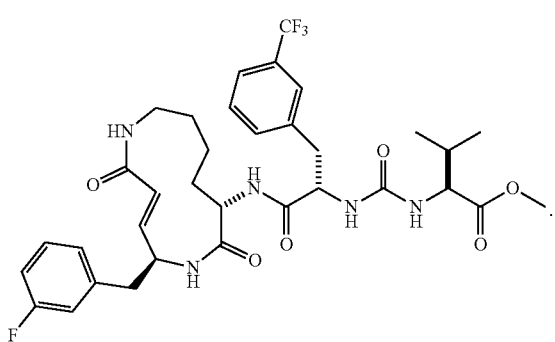 [SMILES: COC(=O)[C@@H](NC(=O)N[C@@H](Cc1cccc(C(F)(F)F)c1)C(=O)N[C@H]1CCCCNC(=O)/C=C/[C@H](Cc2cccc(F)c2)NC1=O)C(C)C]

14. The compound of claim 1, wherein the compound is (S)-methyl 2-(3-((S)-1-((5S,8S, E)-5-(3-fluorobenzyl)-2,7-dioxo-1,6-diazacyclododec-3-en-8-ylamino)-1-oxo-3-(3-(trifluoromethyl)phenyl)propan-2-yl)ureido)-3-methylbutanoate (32)

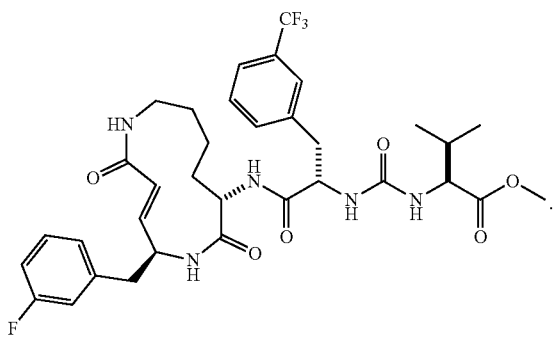 [SMILES: COC(=O)[C@@H](NC(=O)N[C@@H](Cc1cccc(C(F)(F)F)c1)C(=O)N[C@H]1CCCCNC(=O)/C=C/[C@H](Cc2cccc(F)c2)NC1=O)C(C)C]

15. A pharmaceutical composition comprising at least one compound of claim 1 and at least one pharmaceutically acceptable carrier.

16. The pharmaceutical composition of claim 15, further comprising at least one additional anticancer agent.

17. The pharmaceutical composition of claim 16, wherein the at least one compound and the at least one additional anticancer agent are co-formulated in the pharmaceutical composition.

18. A method of inhibiting or preventing protein degradation in a cell, the method comprising contacting the cell with an effective amount of at least one compound of claim 1.

19. A method of treating cancer in a subject in need thereof, the method comprising administering to the subject a therapeutically effective amount of at least one compound of claim 1; wherein the cancer is selected from the group consisting of multiple myeloma, mantle cell lymphoma, leukemia, non-small cell lung cancer, colon cancer, CNS cancer, melanoma, ovarian cancer, renal cancer, prostate cancer and breast cancer.

20. A prepackaged pharmaceutical composition comprising at least one compound of claim 1, or a salt, racemic mixture, enantiomer, pro-drug, or diastereoisomer thereof, an applicator, and an instructional material for use thereof, wherein the instructional material comprises instructions for treating cancer in a subject.

* * * * *